US010077268B2

(12) United States Patent
Evans et al.

(10) Patent No.: US 10,077,268 B2
(45) Date of Patent: Sep. 18, 2018

(54) FXR AGONISTS AND METHODS FOR MAKING AND USING

(71) Applicants: Salk Institute for Biological Studies, La Jolla, CA (US); The University of Sydney, Sydney (AU)

(72) Inventors: Ronald M. Evans, La Jolla, CA (US); Michael Downes, San Diego, CA (US); Thomas J. Baiga, Escondido, CA (US); John F.W. Keana, Eugene, OR (US); Christopher Liddle, Tura Beach (AU)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 15/263,048

(22) Filed: Sep. 12, 2016

(65) Prior Publication Data
US 2016/0376279 A1 Dec. 29, 2016

Related U.S. Application Data

(63) Continuation-in-part of application No. PCT/US2015/020582, filed on Mar. 13, 2015.

(60) Provisional application No. 61/952,754, filed on Mar. 13, 2014, provisional application No. 62/061,463, filed on Oct. 8, 2014, provisional application No. 62/252,059, filed on Nov. 6, 2015.

(51) Int. Cl.
| | |
|---|---|
| *A61K 31/55* | (2006.01) |
| *C07D 487/04* | (2006.01) |
| *C07B 59/00* | (2006.01) |
| *C07D 235/18* | (2006.01) |
| *C07D 209/18* | (2006.01) |
| *C07D 403/06* | (2006.01) |
| *C07D 401/06* | (2006.01) |

(52) U.S. Cl.
CPC .......... *C07D 487/04* (2013.01); *C07B 59/002* (2013.01); *C07D 209/18* (2013.01); *C07D 235/18* (2013.01); *C07D 401/06* (2013.01); *C07D 403/06* (2013.01)

(58) Field of Classification Search
CPC .............................. A61K 31/55; C07D 487/04
USPC ...................................... 514/212.06; 540/580
See application file for complete search history.

(56) References Cited

U.S. PATENT DOCUMENTS

| | | | |
|---|---|---|---|
| 2005/0054634 | A1 | 3/2005 | Busch et al. |
| 2006/0128764 | A1 | 6/2006 | Downes et al. |
| 2008/0299118 | A1 | 12/2008 | Hartman et al. |
| 2008/0300235 | A1 | 12/2008 | Harnish et al. |
| 2009/0163474 | A1 | 6/2009 | Zhang et al. |
| 2009/0215748 | A1 | 8/2009 | Harnish et al. |
| 2011/0039824 | A1* | 2/2011 | Lundquist, IV ..... C07D 487/04 514/215 |
| 2011/0294767 | A1 | 12/2011 | Gedulin et al. |

FOREIGN PATENT DOCUMENTS

| | | |
|---|---|---|
| WO | WO 2002/076945 A1 | 10/2002 |
| WO | WO 2003/099821 A1 | 12/2003 |
| WO | WO 2004/045511 | 6/2004 |
| WO | WO 2007/070796 A1 | 6/2007 |
| WO | WO 2008/051942 A2 | 5/2008 |
| WO | WO 2008/073825 A1 | 6/2008 |
| WO | WO 2010/036362 A1 | 4/2010 |
| WO | WO 2011/150286 A2 | 12/2011 |
| WO | WO 2013/020108 A2 | 2/2013 |
| WO | WO 2013/040441 A1 | 3/2013 |
| WO | WO 2014/179734 A1 | 11/2014 |
| WO | WO 2014/184271 A1 | 11/2014 |
| WO | WO 2015/012400 A1 | 1/2015 |
| WO | WO 2015/138986 | 9/2015 |

OTHER PUBLICATIONS

CAS Registry No. 938197-65-0; STN Entry Date Jun. 21, 2007; 2-Propenoic acid, 3-[3- [[[4-(3-butoxy-3-oxo-1-propen-1-yl)phenyl]methyl](cyclohexylcarbonyl)amino]phenyl]-, methyl ester CAS Registry No. 938197-65-0.
CAS Registry No. 1348506-83-1; STN Entry Date Dec. 4, 2011; 2-Propenoic acid, 3-[3-[[[4-[(1E)-2-(2-fluorophenyl)ethenyl]phenyl]methyl](1-oxohexyl)amino]phenyl]-, methyl ester, (2E)-CAS Registry No. 1348506-83-1.
CAS Registry No. 1350073-50-5; STN Entry Date Dec. 7, 2011; 2-Propenoic acid, 3-[3-[[(3'-methoxy[1,1'-biphenyl]-4-yl)methyl](1-oxohexyl)amino]phenyl]-, methyl ester, (2E)-CAS Registry No. 1350073-50-5.
CAS Registry No. 1025915-35-8; STN Entry Date Jun. 6, 2008; Acetamide, N-[3-[(acetyloxy)methyl]phenyl]-N-[[3-chloro-4-(tetradecyloxy)phenyl]methyl]-XCAS Registry No. 1025915-35-8.

(Continued)

Primary Examiner — Brenda Libby Coleman
(74) Attorney, Agent, or Firm — Klarquist Sparkman, LLP

(57) ABSTRACT

Novel FXR agonists are disclosed, embodiments of a method of making the same, and of a composition comprising them are disclosed herein. Also disclosed are embodiments of a method of treating or preventing a metabolic disorder in a subject, comprising administering to a subject (e.g., via the gastrointestinal tract) a therapeutically effective amount of one or more of the disclosed compounds, thereby activating FXR receptors in the intestines, and treating or preventing a metabolic disorder in the subject. Additionally disclosed are embodiments of a method of treating or preventing inflammation in an intestinal region of a subject, comprising administering to the subject (e.g., via the gastrointestinal tract) a therapeutically effective amount of one or more of the disclosed compounds, thereby activating FXR receptors in the intestines, and thereby treating or preventing inflammation in the intestinal region of the subject.

2 Claims, 24 Drawing Sheets
(20 of 24 Drawing Sheet(s) Filed in Color)
Specification includes a Sequence Listing.

(56) References Cited

OTHER PUBLICATIONS

Fang et al., "Intestinal FXR agonism promotes adipose tissue browning and reduces obesity and insulin resistance," *Nature Medicine* 21(2):159-165, published online Jan. 5, 2015.
Ghorbani et al., "Appearance of brown adipocytes in white adipose tissue during CL 316,243-induced reversal of obesity and diabetes in Zucker fa/fa rats," *International Journal of Obesity* 21:465-475, 1997, Jun. 1997.
Hambruch et al., "Synthetic Farnesoid X Receptor Agonists Induce High-Density Lipoprotein-Mediated Transhepatic Cholesterol Efflux in Mice and Monkeys and Prevent Atherosclerosis in Cholesteryl Ester Transfer Protein Transgenic Low-Density Lipoprotein Receptor (-/-) Mice," *The Journal of Pharmacology and Experimental Therapeutics* 343:556-567, 2012, Dec. 1, 2012.
Hawa et al., "Adult-Onset Autoimmune Diabetes in Europe Is Prevalent With a Broad Clinical Phenotype," *Diabetes Care* 36:908-913, 2013, published online Dec. 17, 2012.
International Search Report dated Jun. 1, 2015 from International Application No. PCT/US2015/020582 (10 pages).
International Search Report dated Jun. 26, 2015 from International Application No. PCT/US2015/020552 (9 pages).
International Search Report dated May 2, 2016 from International Application No. PCT/US2016/022082 (5 pages).
Lundquist et al., "Improvement of Physiochemical Properties of the Tetrahydroazepinoindole Series of Farnesoid X Receptor (FXR) Agonists: Beneficial Modulation of Lipids in Primates," *Journal of Medical Chemistry* 53:1774-1787, 2010, Jan. 22, 2010.
Mudaliar et al., "Farnesoid-X Receptor Agonists—A New Therapeutic Class for Diabetes and NAFLD—First Clinical Data," *Diabetologia* 52:S78, 2009, Aug. 14, 2009.
Schuster et al., "Pharmacophore-Based Discovery of FXR Agonists. Part I: Model Development and Experimental Validation," *Bioorganic & Medicinal Chemistry* 19:7168-7180, 2011, published online Oct. 4, 2011.
Tang et al., "Conformation-Induced Remote Meta-C-H Activation of Amines," *Nature* 507:215-220, published online Mar. 12, 2014.
Written Opinion dated Jun. 1, 2015 from International Application No. PCT/US2015/020582 (9 pages).
Written Opinion dated Jun. 26, 2015 from International Application No. PCT/US2015/020552 (10 pages).
Written Opinion dated May 2, 2016 from International Application No. PCT/US2016/022082 (8 pages).
Foster, "Deuterium isotope effects in the metabolism of drugs and xenobiotics: Implications for drug design," *Advances in Drug Design* 14:1-40, 1985.
International Search Report from International Application No. PCT/US2016/057532 dated Jan. 16, 2017.
International Search Report from International Application No. PCT/US2016/057527 dated Feb. 6, 2017.
Written Opinion from International Application No. PCT/US2016/057532 dated Jan. 16, 2017.
Written Opinion from International Application No. PCT/US2016/057527 dated Feb. 6, 2017.
Crawley, "Farnesoid X receptor modulators: a patent review," *Expert Opinion on Therapeutic Patents* 20(8):1047-1057, 2010.
Downes et al., "A Chemical, Genetic, and Structural Analysis of the Nuclear Bile Acid Receptor FXR," *Molecular Cell* 11:1079-1092, Apr. 2003.
Partial European Search Report dated Sep. 22, 2017, from European Application No. 15761517.0.
Richter et al., "Optimization of a novel class of benzimidazole-based farnesoid X receptor (FXR) agonists to improve physicochemical and ADME properties," *Bioorganic & Medicinal Chemistry Letters* 21:1134-1140, 2011.
Stojancevic et al., "The impact of farnesoid X receptor activation on intestinal permeability in inflammatory bowel disease," *Canadian Journal of Gastroenterology* 26(9):631-637, Sep. 2012.

* cited by examiner

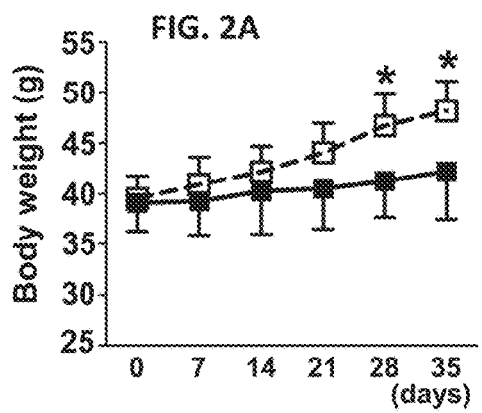
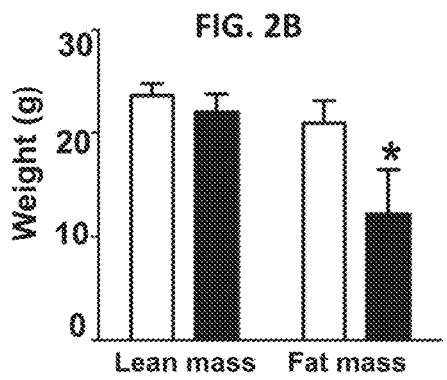
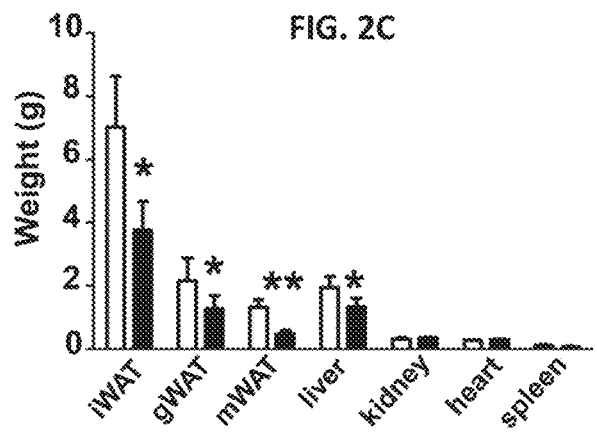
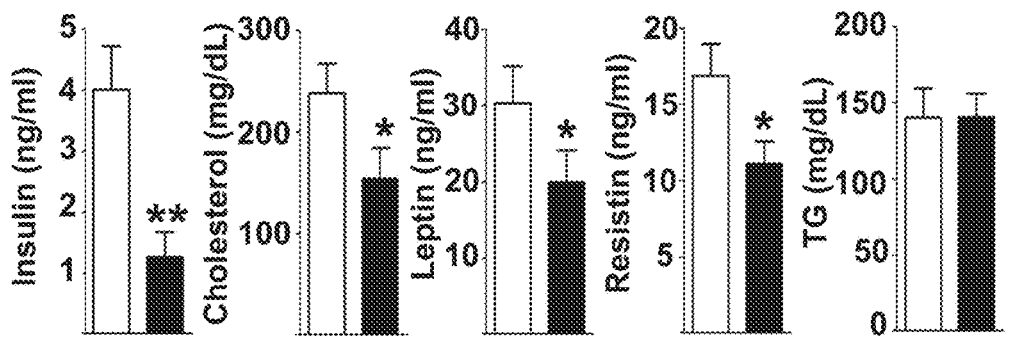

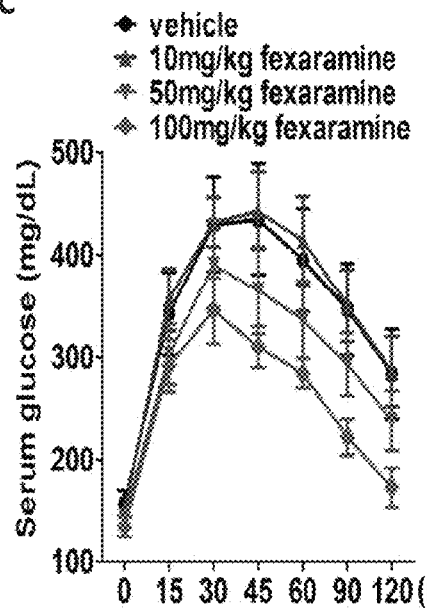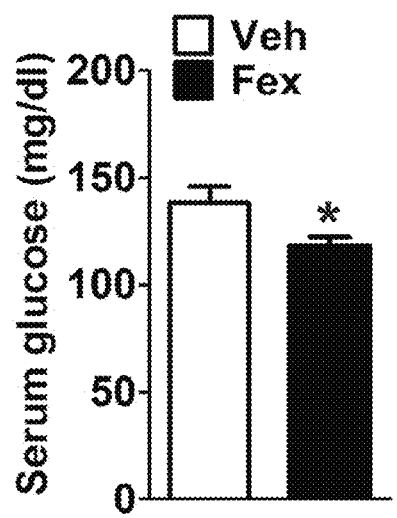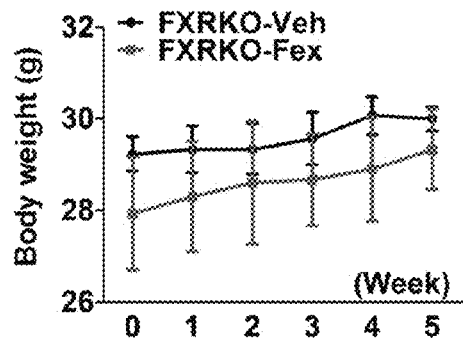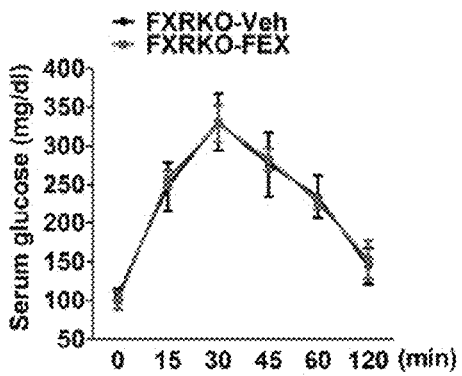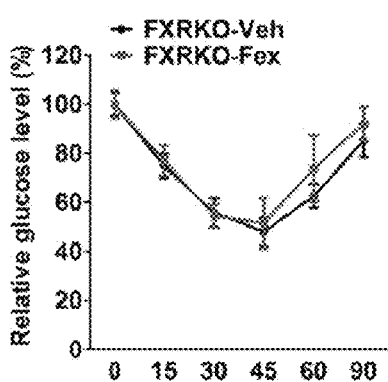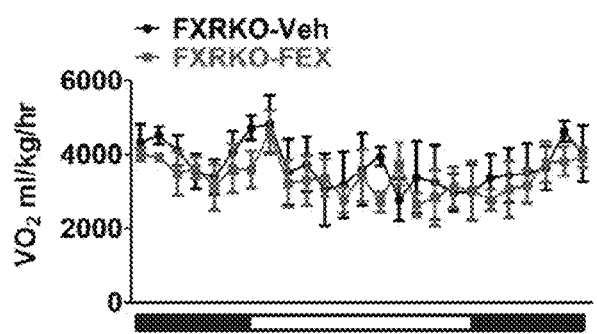

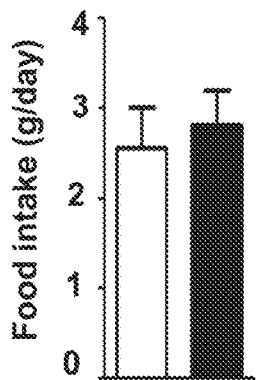
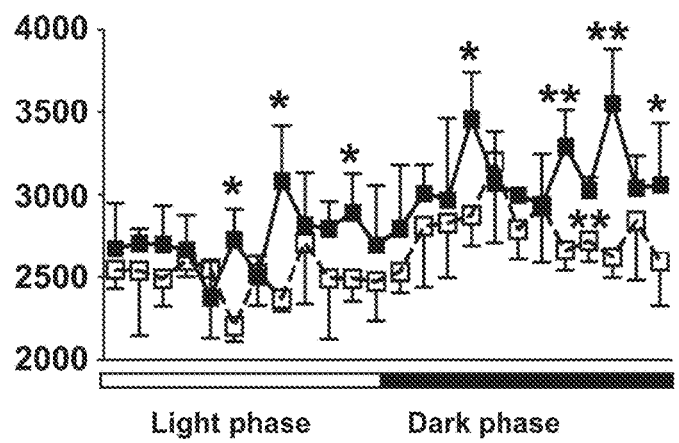
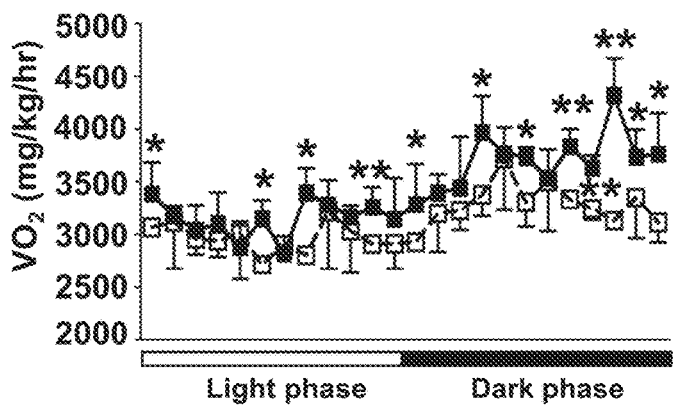
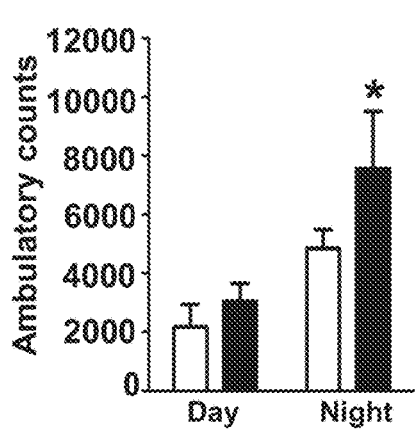
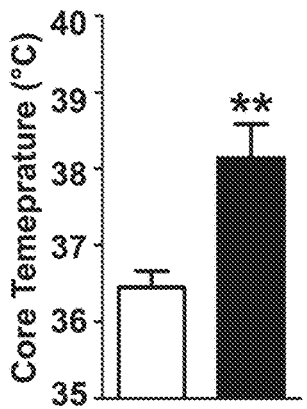
FIG. 6A
FIG. 6B
FIG. 6C
FIG. 6D
FIG. 6E

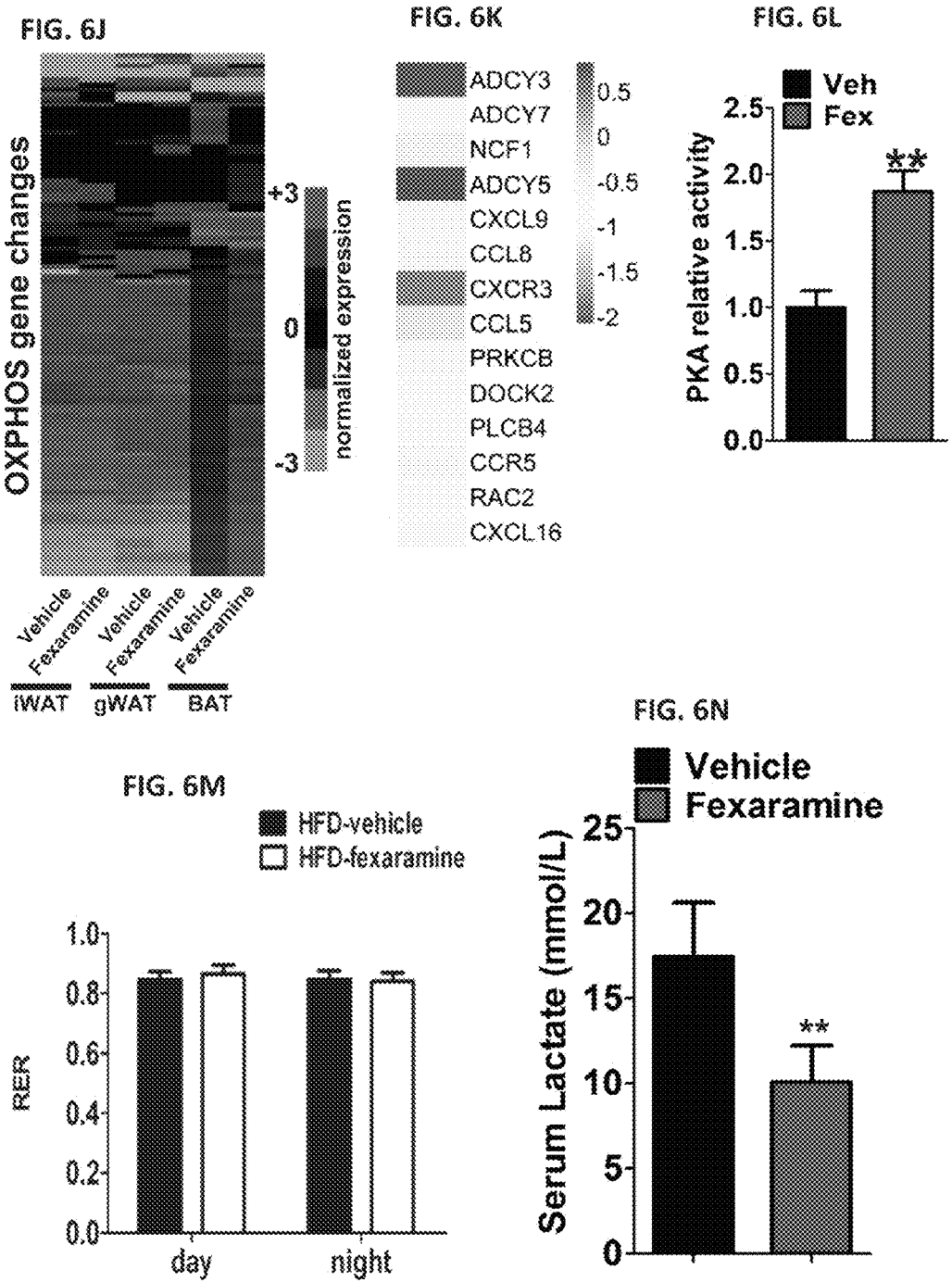

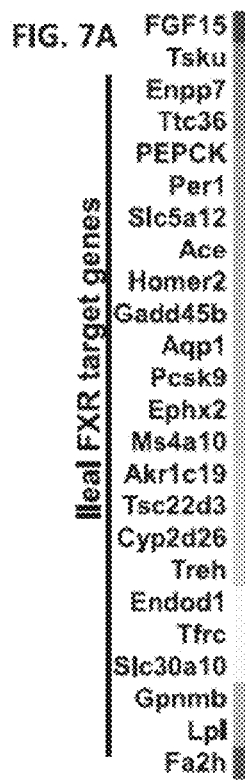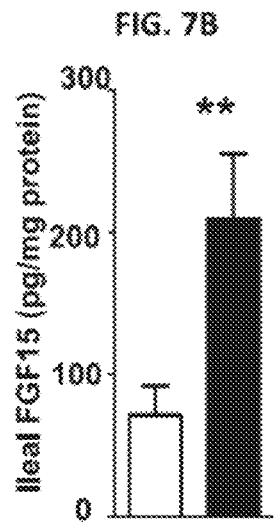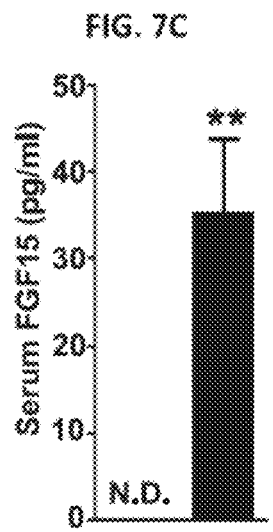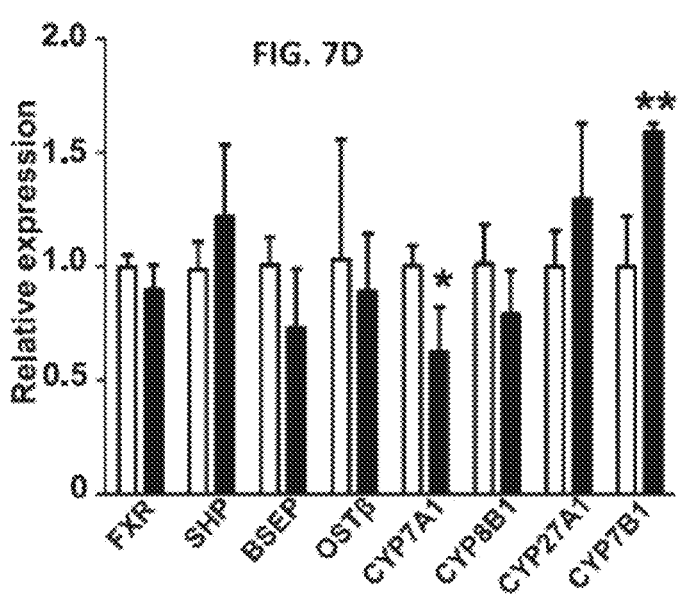

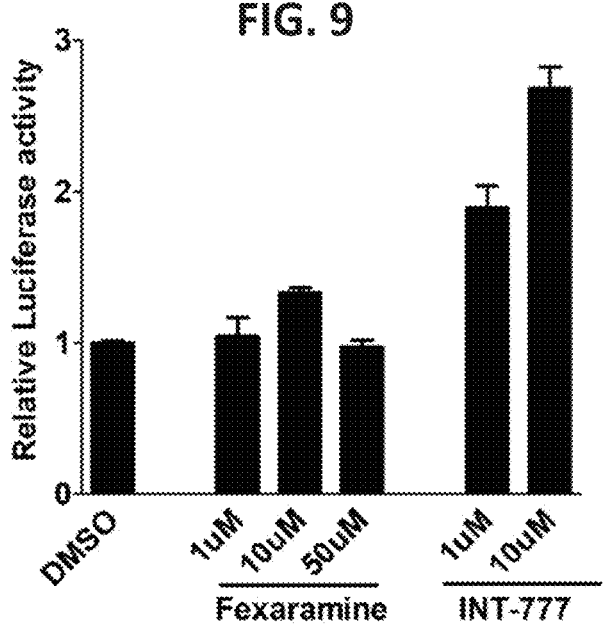
FIG. 9
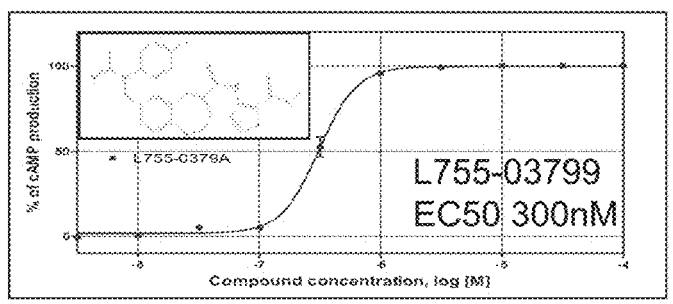
FIG. 10A
FIG. 10B
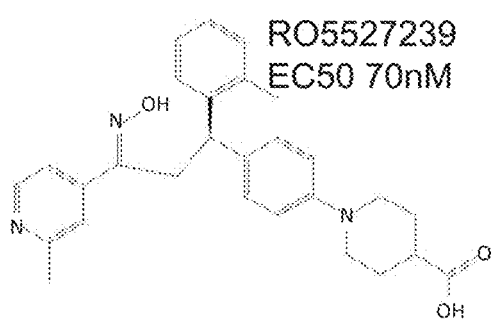
FIG. 10C
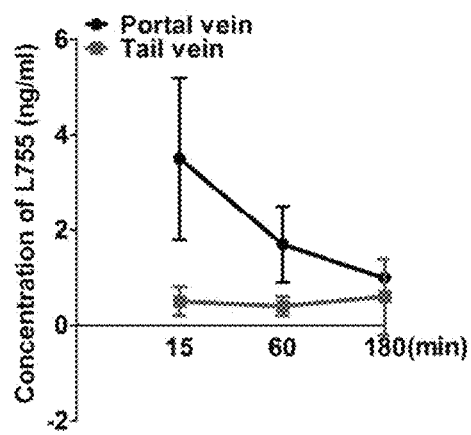

FIG. 11E
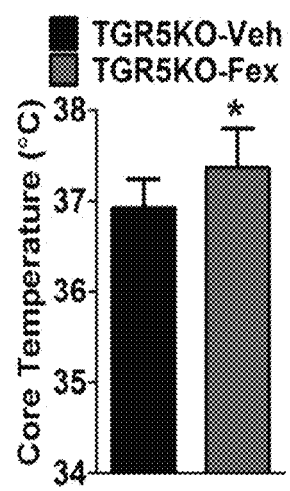
FIG. 11F
FIG. 11G
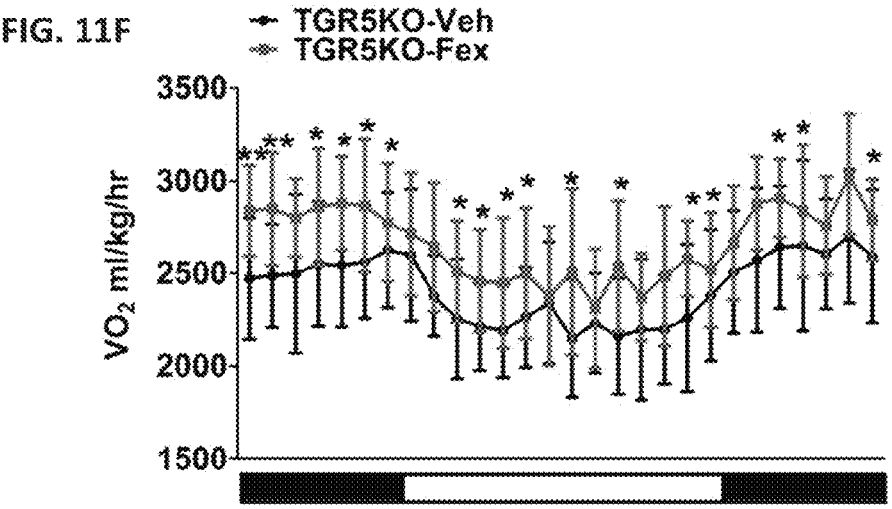

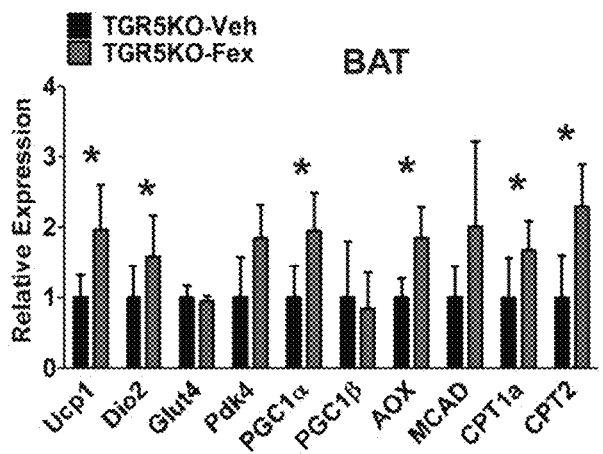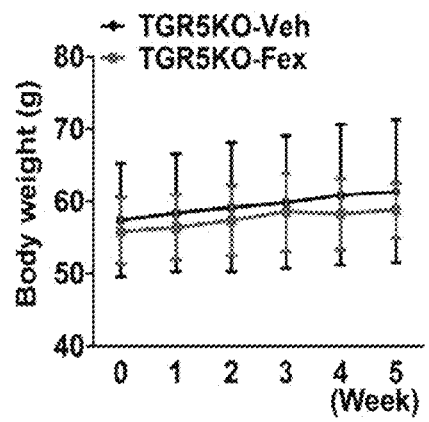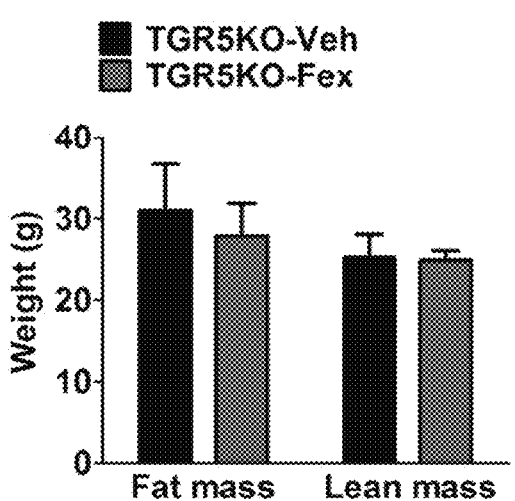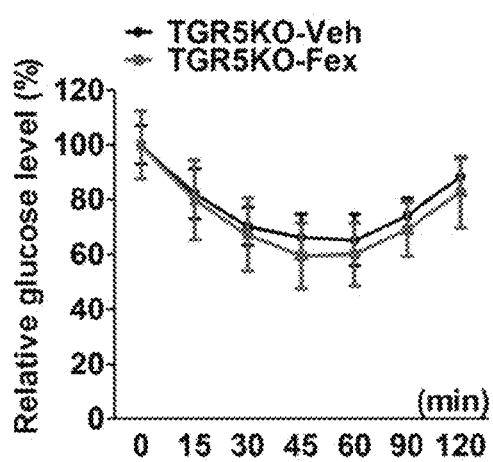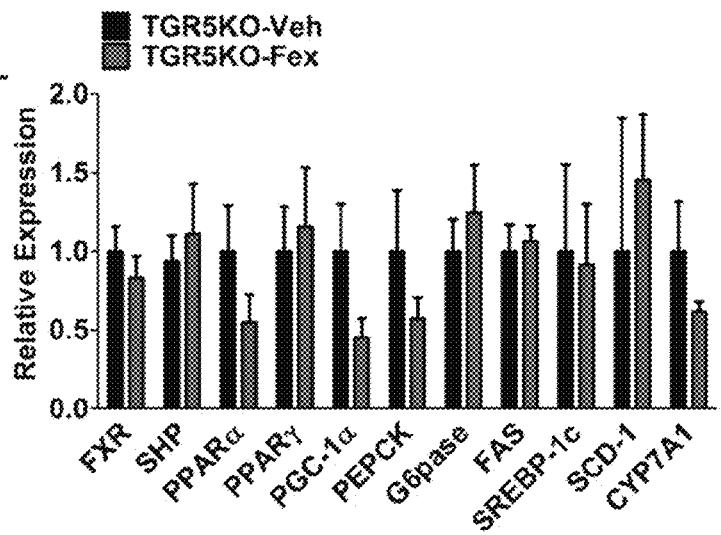

FXR AGONISTS AND METHODS FOR MAKING AND USING

CROSS-REFERENCE TO RELATED APPLICATIONS

This application is a continuation-in-part of International Application No. PCT/US2015/020582, filed Mar. 13, 2015, which claims the benefit of U.S. Provisional Application Nos. 61/952,754 filed Mar. 13, 2014 and 62/061,463 filed Oct. 8, 2014. This application also claims the benefit of U.S. Provisional Application No. 62/252,059, filed Nov. 6, 2015. Each of these prior applications is incorporated herein by reference.

ACKNOWLEDGEMENT OF GOVERNMENT SUPPORT

This invention was made with Government support under Grant Nos. DK062434 and DK097748 awarded by the National Institutes of Health. The government has certain rights in the invention.

FIELD

This disclosure concerns new FXR agonists and a method for using the agonists, such as to treat or prevent gastrointestinal (GI) inflammatory conditions, intestinal permeability conditions, intestinal altered microbiome conditions, cholestatic disorders, bile disorders, intestinal absorption disorders, and metabolic disorders, including obesity and diabetes.

PARTIES TO JOINT RESEARCH AGREEMENT

Salk Institute for Biological Studies and The University of Sydney are parties to a joint research agreement governing inventions disclosed herein.

BACKGROUND

Metabolic syndrome, a western diet-induced, pro-inflammatory disease affecting up to 25% of Americans, is characterized by central obesity, impaired glucose tolerance, dyslipidemia, insulin resistance, and type II diabetes. Secondary complications associated with metabolic syndrome include atherosclerosis, stroke, fatty liver disease, blindness, gallbladder disease, cancer, polycystic ovary disease and others. Consequently there is interest in reducing food intake, losing weight, and reducing elevated blood glucose. There is also an interest in combating obesity and related conditions using methods that do not require drastic lifestyle or dietary changes. In addition, inflammatory gastrointestinal conditions resulting from various types of pathology affect millions of people. Thus, effective and targeted treatments for various inflammatory gastrointestinal (GI) conditions are also needed.

Farnesoid X receptor (FXR) is a ligand-activated transcriptional receptor expressed in diverse tissues including the adrenal gland, kidney, stomach, duodenum, jejunum, ileum, colon, gall bladder, liver, macrophages, and white and brown adipose tissue (Forman et al., Cell 81: 687-693 (1995). FXR has been reported to contribute to the regulation of whole body metabolism including bile acid/cholesterol, glucose and lipid metabolism. Synthetic ligands for FXR have been identified and applied to animal models of metabolic disorders, but these known synthetic ligands have shown limited efficacy and, in certain cases, exacerbated phenotypes.

Bile acids (BAs) function as endogenous ligands for FXR such that enteric and systemic release of BAs induces FXR-directed changes in gene expression networks (Lee et al., *Trends Biochem Sci* 31: 572-580, 2006; Repa et al., *Science* 289: 1524-1529, 2000; Zollner et al., *J Hepatol* 39: 480-488, 2003; Fang et al., *J Biol Chem* 283: 35086-35095, 2008; Kemper et al., *Cell Metab* 10: 392-404, 2009; Makishima et al., *Science* 284: 1362-1365, 1999; Stedman et al., *Proc Natl Acad Sci USA* 103: 11323-11328, 2006). The complex role of FXR in metabolic homeostasis is evident in studies on whole body FXR knockout (FXR KO) mice. On a normal chow diet, FXR KO mice develop metabolic defects including hyperglycemia and hypercholesterolemia, but conversely, exhibit improved glucose homeostasis compared to control mice when challenged with a high fat diet (Sinal et al., *Cell* 102: 731-744, 2000; Prawitt et al., *Diabetes* 60: 1861-1871, 2011). Similar contrary effects are seen with systemic FXR agonists, with beneficial effects observed when administered to chow-fed mice and exacerbated weight gain and glucose intolerance observed when administered to diet-induced obesity (DIO) mice (Zhang et al., *Proc Natl Acad Sci USA* 103: 1006-1011, 2006; Watanabe et al., *J Biol Chem* 286: 26913-26920, 2011).

In the liver, FXR activation suppresses hepatic BA synthesis, alters BA composition, reduces the BA pool size (Wang et al., *Dev Cell* 2: 721-731, 2002; Fang et al., *Mol Cell Biol* 27: 1407-1424, 2007; Lu et al., *Mol Cell* 6: 507-515, 2000), and contributes to liver regeneration (Huang et al., *Science* 312:233-236, 2006) as well as lipid and cholesterol homeostasis (Zhang et al., *Genes Dev* 18: 157-169, 2004; Ma et al., *J Clin Invest* 116: 1102-1109, 2006). Consistent with this, activation of hepatic FXR by the synthetic bile acid 6α-ethyl chenodeoxycholic acid (6-eCDCA) is beneficial in the treatment of diabetes, non-alcoholic fatty liver disease (NAFLD), and primary biliary cirrhosis (PBC) (Stanimirov et al., *Acta Gastroenterol Belg* 75: 389-398, 2012; Mudaliar et al., *Gastroenterology* 145: 574-582 e571, 2013).

FXR is also widely expressed in the intestine where it regulates production of the endocrine hormone FGF15 (FGF19 in humans), which, in conjunction with hepatic FXR, is thought to control BA synthesis, transport and metabolism (Kim et al., *J Lipid Res* 48: 2664-2672, 2007; Song et al., *Hepatology* 49: 97-305, 2009; Inagak et al., *Cell Metab* 2: 217-225, 2005). Intestinal FXR activity is also known to be involved in reducing overgrowth of the microbiome during feeding (Li et al., *Nat Commun* 4: 2384, 2013; Inagaki et al., *Proc Natl Acad Sci USA* 103: 3920-3925, 2006).

SUMMARY

One disclosed embodiment of the present invention concerns a compound having a formula

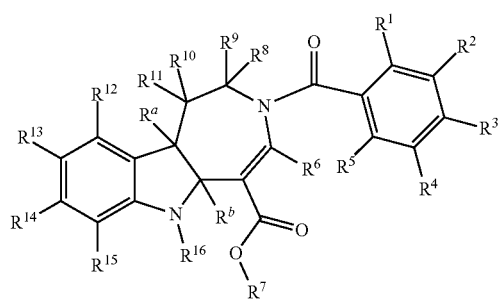

or a pharmaceutically acceptable salt, hydrate, N-oxide or solvate thereof. With reference to this formula: $R^1$-$R^{15}$ independently are selected from hydrogen, deuterium, halogen, $CF_3$, $NO_2$, OH, amino, acyl, carboxyl, carboxyl ester, cyano, aminocarbonyl, aminosulfonyl, aliphatic, D-aliphatic, heteroaliphatic, D-heteroaliphatic, or —$(CH_2)_{n1}$—$R^{150}$—$(CH_2)_{n2}$—$R^{151}$, wherein n1 and n2 are independently selected from the group consisting of 0, 1, 2, 3, and 4, $R^{150}$ is O, $NR^{16}$, or absent, and $R^{151}$ is carboxyl ester or amino; $R^{16}$ is selected from hydrogen, aliphatic, D-aliphatic, heteroaliphatic or D-heteroaliphatic; $R^a$ and $R^b$ are independently hydrogen, deuterium, aliphatic or D-aliphatic, or together form a bond, such as a pi-bond; and if $R^a$ and $R^b$ together form a pi-bond then at least one of $R^1$-$R^{16}$ is or comprises deuterium.

In some embodiments, the compound has a formula

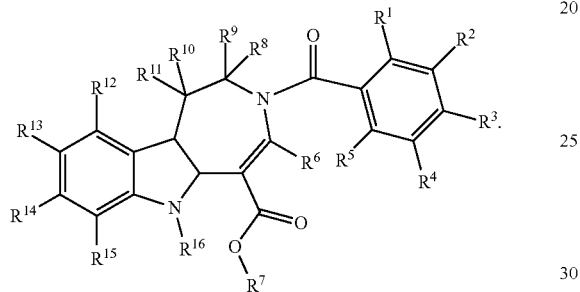

In other embodiments, the compound has a formula

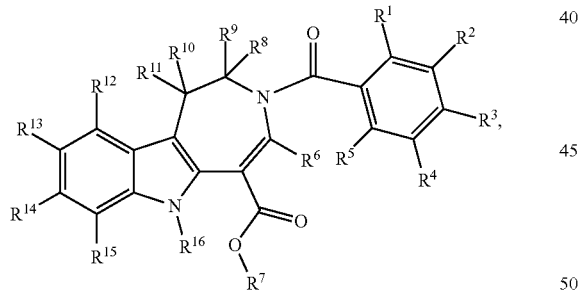

and at least one of $R^1$-$R^{16}$ is or comprises deuterium.

In certain disclosed embodiments, $R^7$ is alkyl or deuterated alkyl, such as isopropyl or a deuterated isopropyl group comprising from 1 to 7 deuterium atoms. In certain embodiments, at least one of $R^1$-$R^5$ is a halogen, such as fluoro. For certain embodiments, $R^{16}$ is hydrogen. In other disclosed embodiments, $R^{10}$ and $R^{11}$ independently are alkyl or deuterated alkyl, such as methyl or deuterated methyl, wherein the deuterated alkyl group comprises from 1 to n halogen atoms where n is the total number of hydrogen atoms on the substituent, such as from 1 to 3 deuterium atoms for a methyl group. Exemplary compounds having this formula include

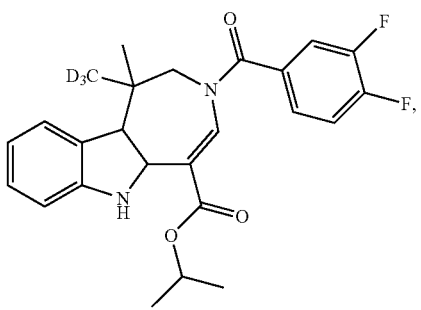

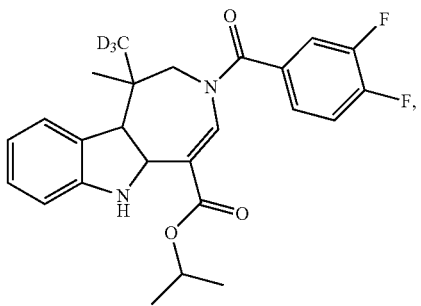

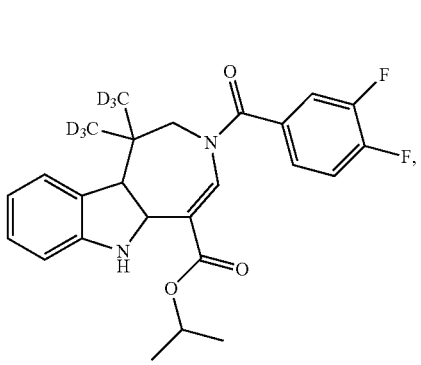

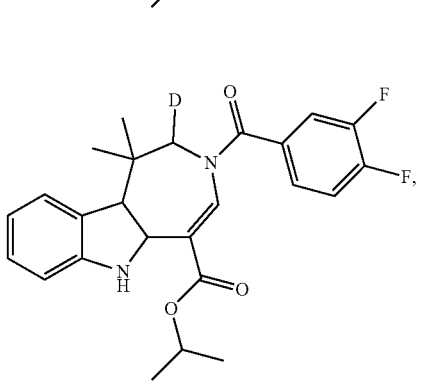

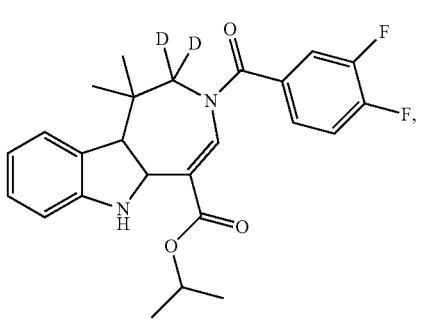

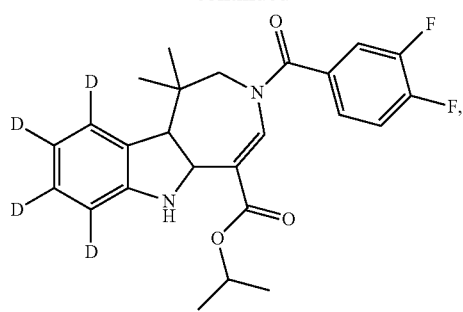
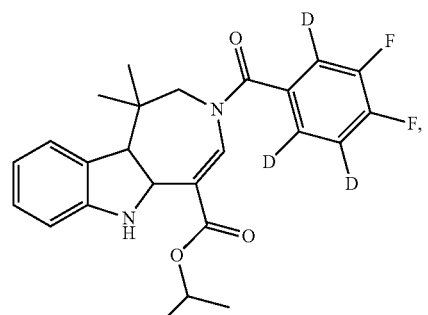
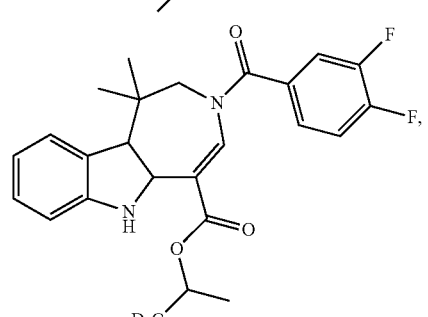
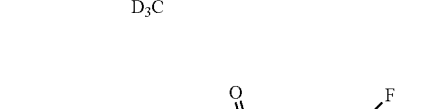
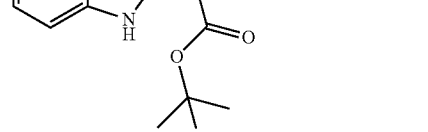
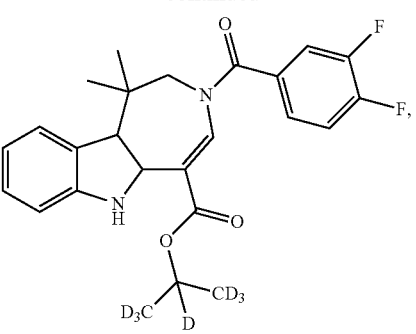
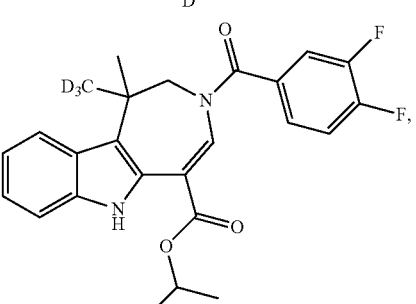
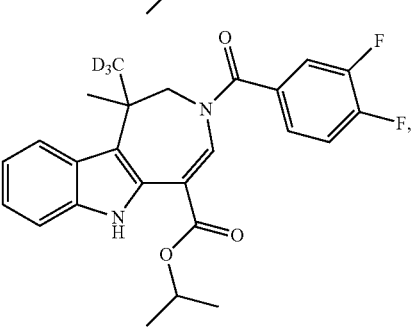
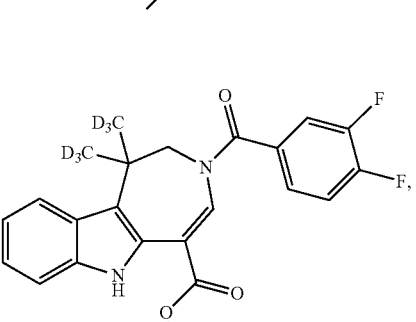
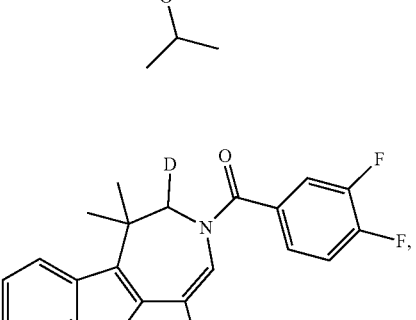

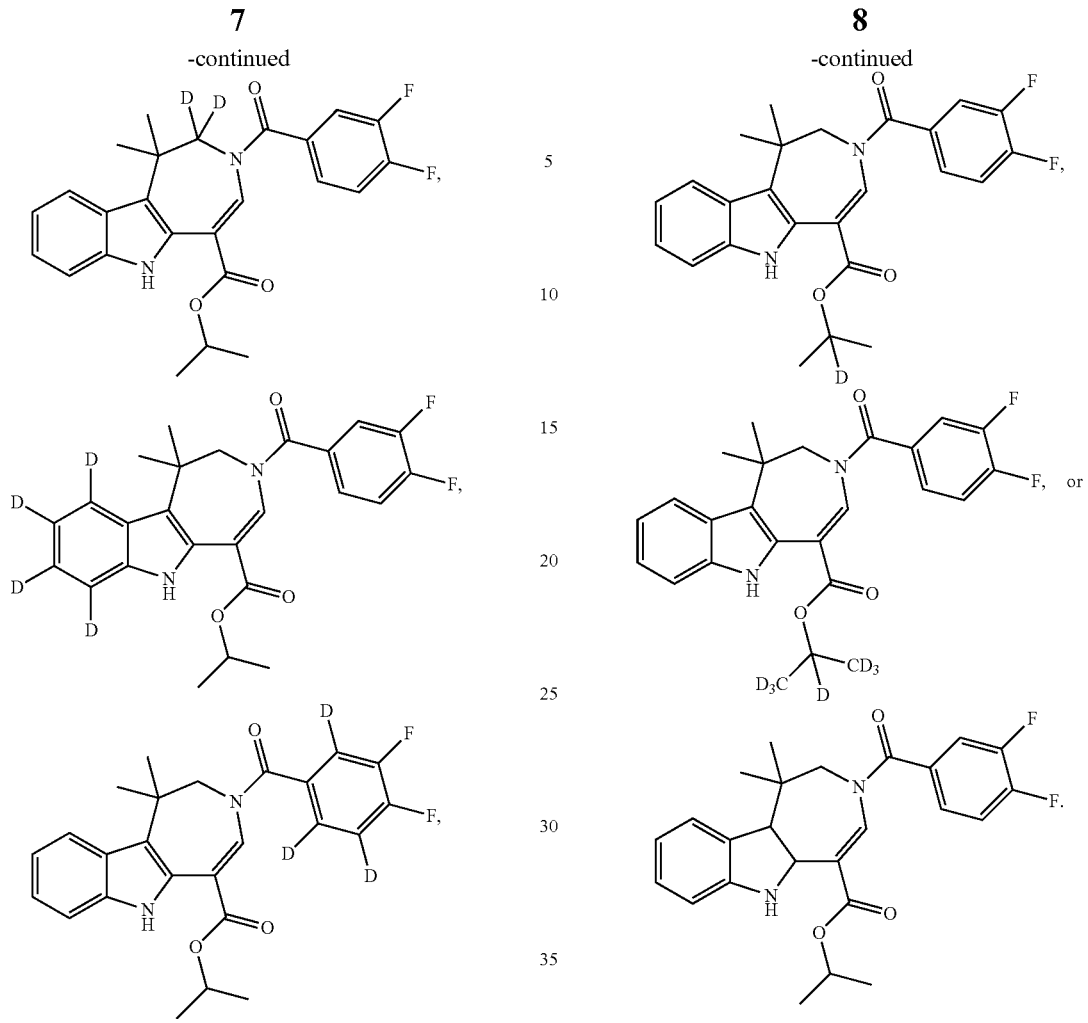

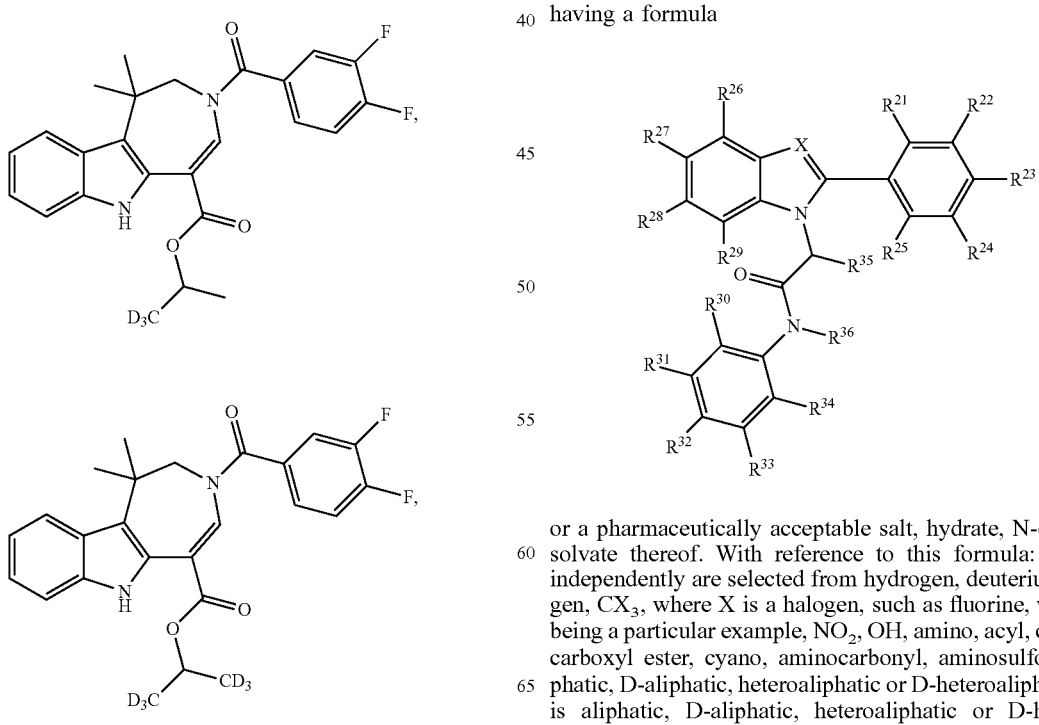

A second disclosed embodiment concerns a compound having a formula or a pharmaceutically acceptable salt, hydrate, N-oxide, or solvate thereof. With reference to this formula: $R^{21}$-$R^{34}$ independently are selected from hydrogen, deuterium, halogen, $CX_3$, where X is a halogen, such as fluorine, with $CF_3$ being a particular example, $NO_2$, OH, amino, acyl, carboxyl, carboxyl ester, cyano, aminocarbonyl, aminosulfonyl, aliphatic, D-aliphatic, heteroaliphatic or D-heteroaliphatic; $R^{35}$ is aliphatic, D-aliphatic, heteroaliphatic or D-heteroaliphatic; $R^{36}$ is hydrogen, aliphatic, D-aliphatic, heteroaliphatic or D-heteroaliphatic; X is N or $CR^{37}$; and $R^{37}$ is hydrogen, deuterium, halogen, $CF_3$, $NO_2$, OH, amino, acyl, carboxyl, carboxyl ester, cyano, aminocarbonyl, aminosulfonyl, aliphatic, D-aliphatic, heteroaliphatic or D-heteroaliphatic; where if X is N, then at least one of $R^{21}$-$R^{36}$ is or comprises deuterium.

In some embodiments, the compound has a formula

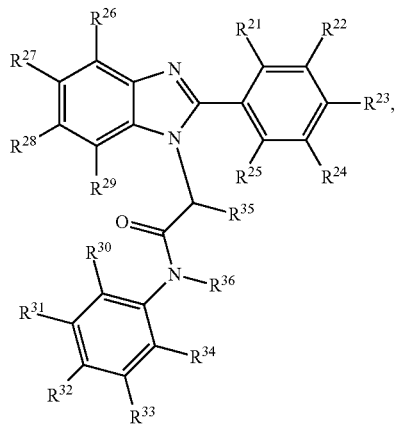

and in other embodiments, the compound has a formula

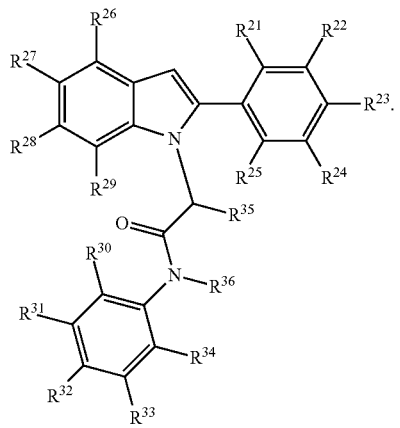

In particular embodiments, $R^{35}$ is alkyl, cycloalkyl, deuterated alkyl or deuterated cycloalkyl, such as cyclohexyl or deuterated cyclohexyl comprising 1 to 11 deuterium atoms. In particular embodiments, $R^{36}$ is hydrogen; $R^{34}$ is $CF_3$; and $R^{23}$ is halogen, such as fluorine or chlorine. Certain compounds are chiral, and all stereoisomers are included in this disclosure. For certain embodiments, the compound is the most biologically active stereoisomer, such as the S-stereoisomer. Exemplary compounds according to this formula include

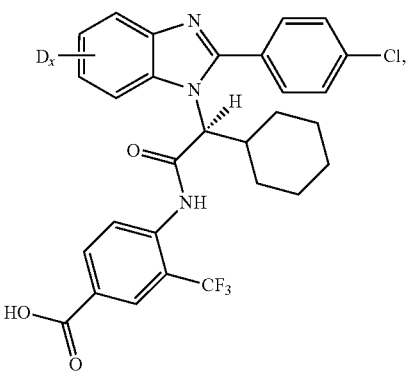

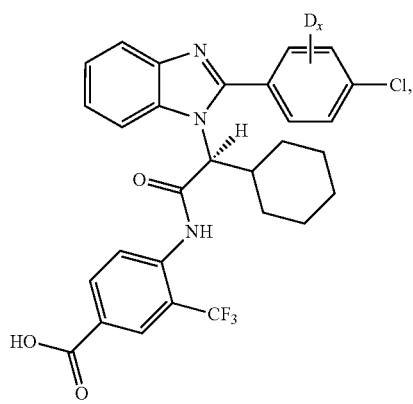

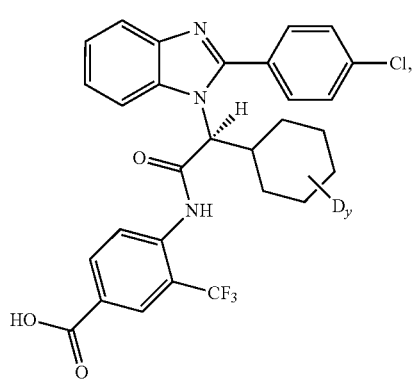

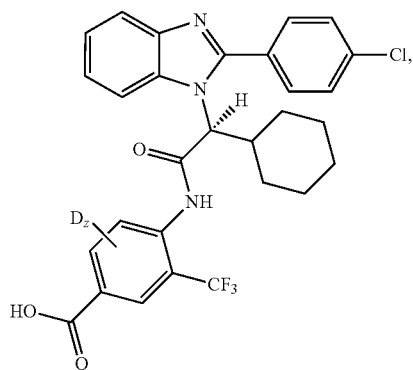

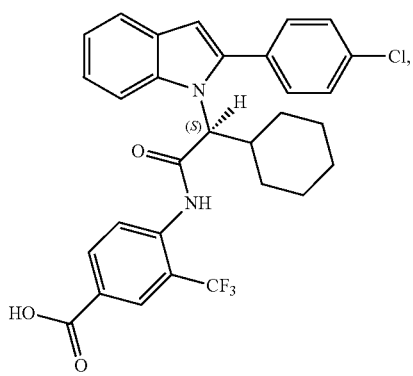

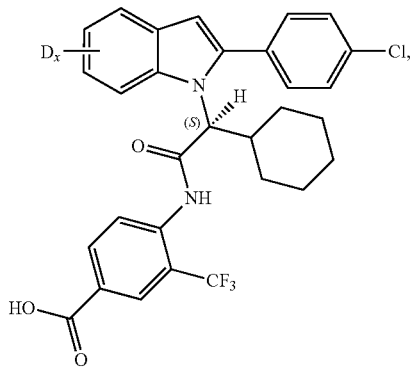

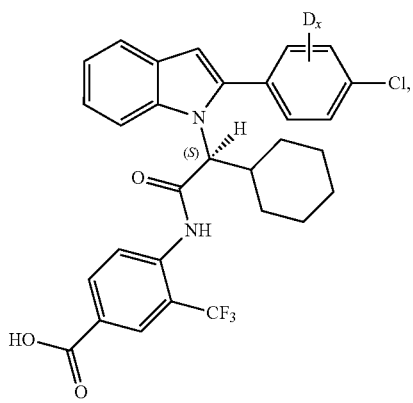

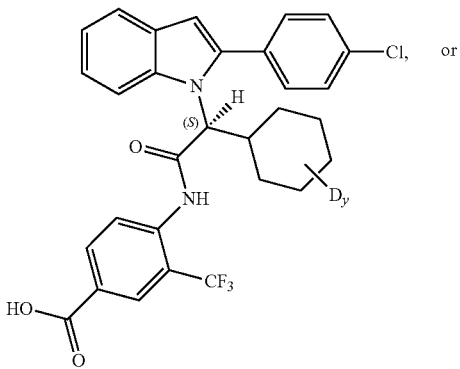

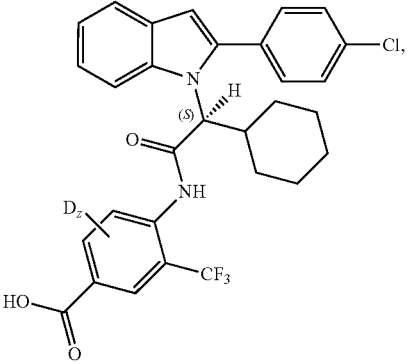

where x is 0 to 4, y is 0 to 11, and z is 0 to 3.

Another disclosed embodiment concerns compound having a formula

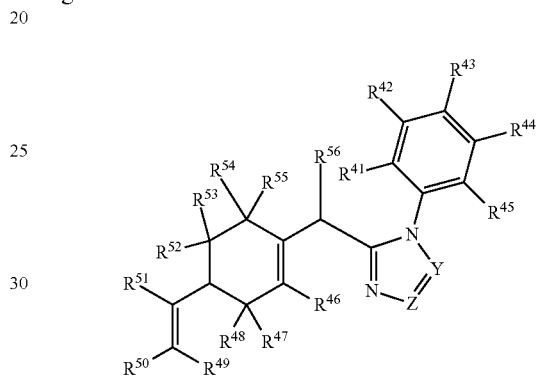

or a pharmaceutically acceptable salt, hydrate, N-oxide or solvate thereof, wherein: $R^{41}$-$R^{48}$ and $R^{52}$-$R^{55}$ independently are selected from hydrogen, deuterium, halogen, $CF_3$, $NO_2$, OH, amino, acyl, carboxyl, carboxyl ester, cyano, aminocarbonyl, aminosulfonyl, aliphatic, D-aliphatic, heteroaliphatic or D-heteroaliphatic; $R^{49}$-$R^{51}$ independently are selected from hydrogen, deuterium, aliphatic, D-aliphatic, heteroaliphatic or D-heteroaliphatic; $R^{56}$ is amino, cycloamino or substituted cycloamino; Y and Z are independently N or $CR^{57}$; and each $R^{57}$ independently is selected from deuterium, halogen, $CF_3$, $NO_2$, OH, amino, acyl, carboxyl, carboxyl ester, cyano, aminocarbonyl, aminosulfonyl, aliphatic, D-aliphatic, heteroaliphatic or D-heteroaliphatic. Certain compounds are chiral, and all stereoisomers are included in this disclosure.

In some embodiments, the compound has a formula selected from

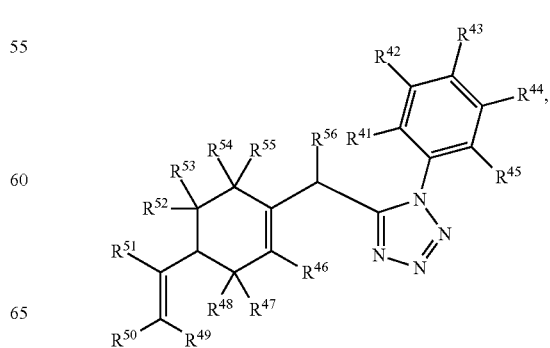

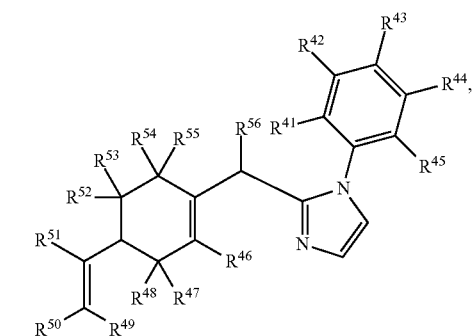

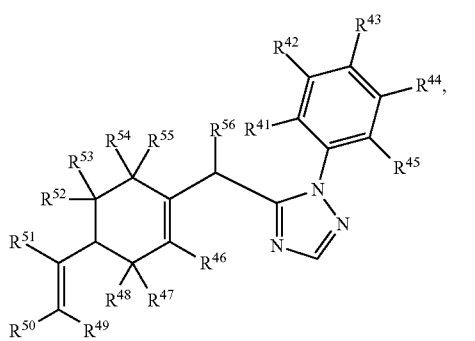

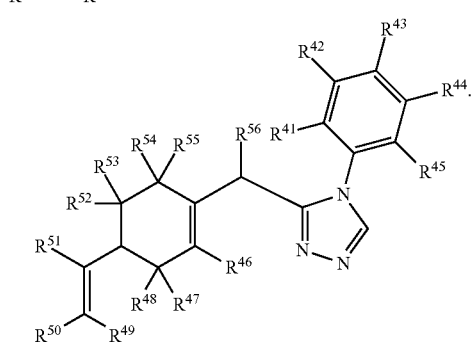

In some embodiments, at least one of $R^{41}$-$R^{56}$ is or comprises deuterium. For certain disclosed embodiments, $R^{51}$ is aliphatic or D-aliphatic, such as methyl or deuterated methyl having from 1 to 3 deuterium atoms. For certain disclosed embodiments, $R^{49}$ and $R^{50}$ independently are hydrogen or deuterium; and $R^{41}$ and $R^{45}$ independently are aliphatic or D-aliphatic, such as methyl or deuterated methyl having from 1 to 3 deuterium atoms. For other embodiments, $R^{56}$ is a cycloamino or substituted cycloamino, such as pyrrolidine, 2-methylpyrrolidine, morpholine, 4-methylpiperazine, piperidine, or azepane. Exemplary compounds having this formula include

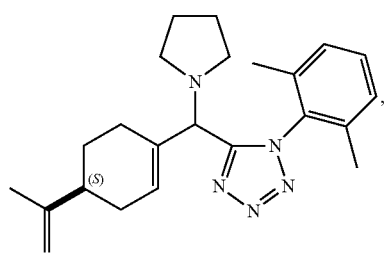

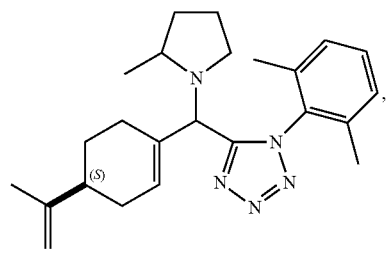

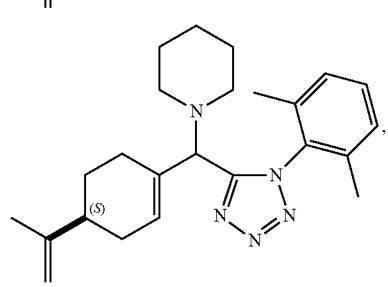

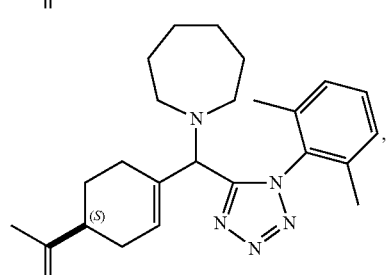

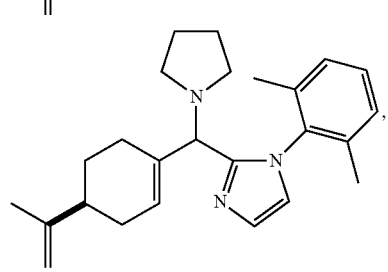

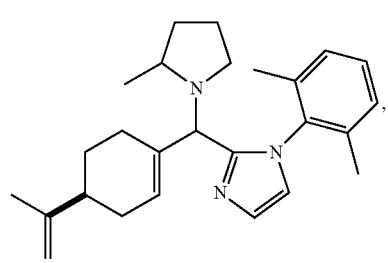

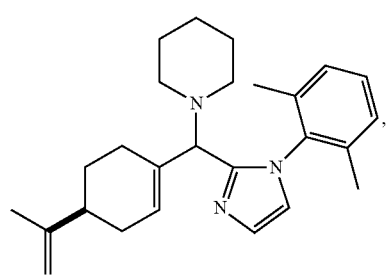

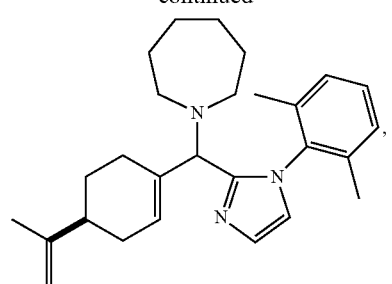,
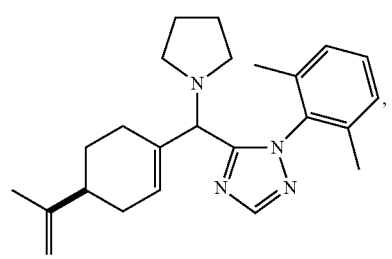,
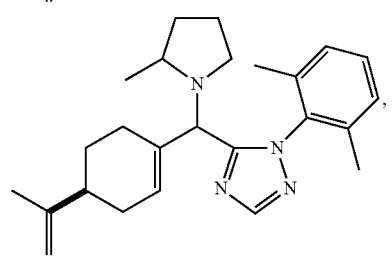,
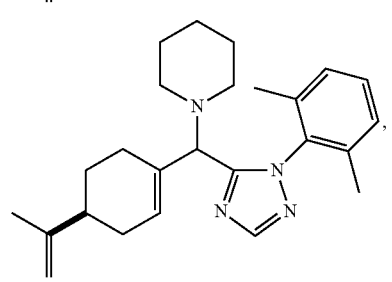,
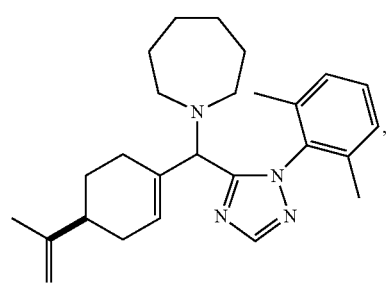,
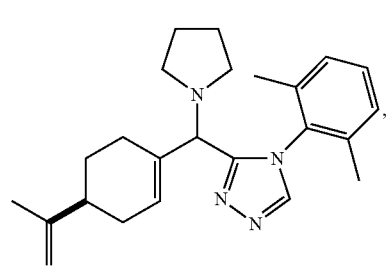,
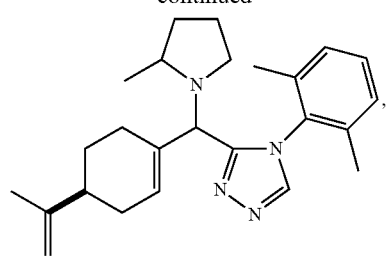,
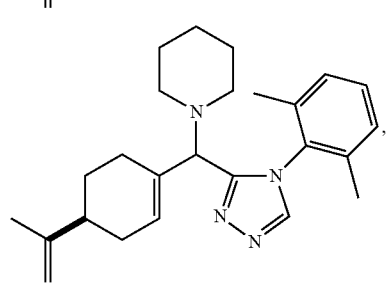,
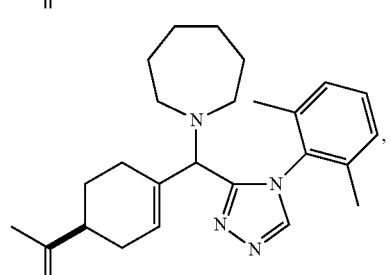,
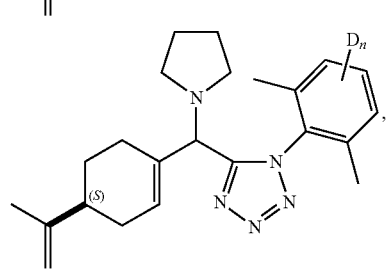,
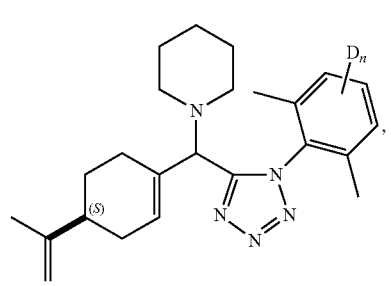,
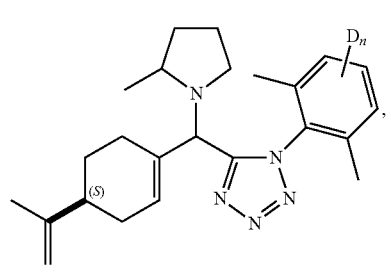,

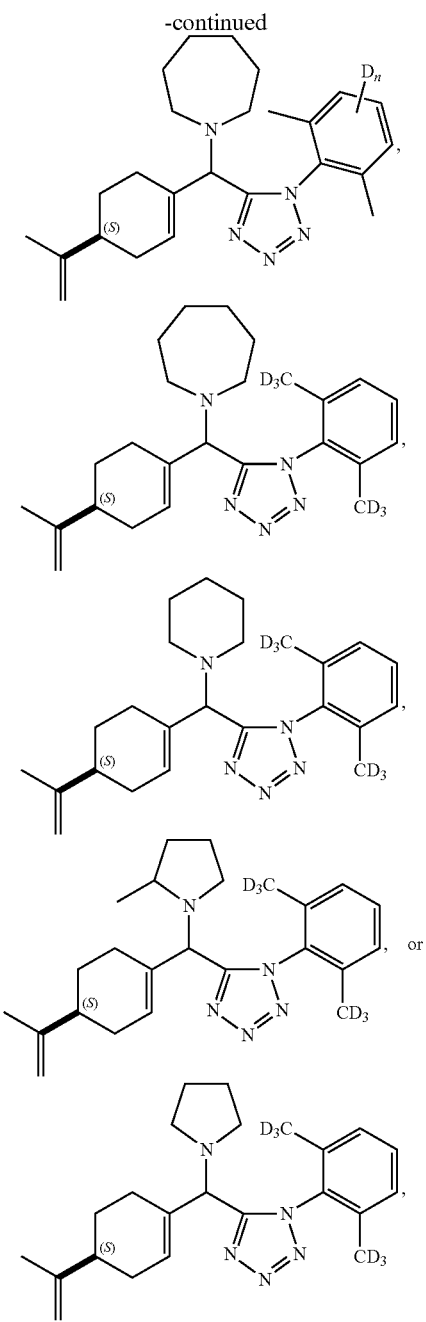

where n is 1 to 3.

Also, in any of the above embodiments, none of $R^1$-$R^{57}$ is —$R^x$-$L^x$-$R^{x2}$, where $R^x$ is selected from O, $NR^{x3}$, sulfonyl or S; $R^{x3}$ is selected from H, aliphatic, or aryl; $L^x$ is selected from a bond, aliphatic, heteroaliphatic, aryl, heteroaryl or $CR^{x4}R^{x5}$; $R^{x4}$ and $R^{x5}$ are each independently selected from H, D, halogen, aliphatic, —$C(O)OR^{x6}$, or —$C(O)NR^{x6}R^{x7}$; $R^{x6}$ and $R^{x7}$ are each independently selected from H, aliphatic; $R^{x2}$ is selected from —$C(O)L^{x2}R^{x8}$ or a carboxyl bioisostere; $L^{x2}$ is a bond or $NR^{x3}$; $R^{x8}$ is H, aliphatic, —$OR^{x9}$, $N(R^{x9})_2$, —$C(O)R^{x9}$, —$S(O)_2R^{x9}$, —$C(O)OR^{x9}$, —$S(O)_2N(R^{x9})_2$ or —$C(O)N(R^{x9})_2$; and each $R^{x9}$ is independently selected from H, aliphatic.

Compositions comprising any such compound, or compounds, and at least one additional component, such as a pharmaceutically exceptable excipient, an additional therapeutic, or combinations thereof, also are disclosed. The compositions may include an enteric coating.

Also disclosed herein are embodiments of a method for treating or preventing a disorder or disease, with particular embodiments concerning a method for treating or preventing a metabolic disorder in a subject. Such methods can include administering to the subject a therapeutically effective amount of one or more of the disclosed compounds and/or compositions (such as 1, 2, 3, 4, or 5 of such compounds and/or compositions). For example, certain disclosed embodiments concerning compounds that are substantially absorbed in the gastrointestinal tract, thereby activating FXR receptors in the intestines to treat or prevent a metabolic disorder in the subject. Certain method embodiments also may improve glucose and/or lipid homeostasis in the subject. In other embodiments, the method further includes administering to the subject a statin, an insulin sensitizing drug, (such as sitagliptin, vildagliptin, saxagliptin, linagliptin, anagliptin, teneligliptin, alogliptin, gemigliptin, or dutogliptin), meglitinide, sulfonylurea, peroxisome proliferator-activated receptor (alpha-glucosidase inhibitor, amylin agonist, dipeptidyl-peptidase 4 (DPP-4) inhibitor PPAR)-gamma agonist (e.g., a thiazolidinedione (TZD) [such as ioglitazone, rosiglitazone, rivoglitazone, or troglitazone], aleglitazar, farglitazar, muraglitazar, or tesaglitazar), a glucagon-like peptide (GLP) agonist, anti-inflammatory agent (e.g., oral corticosteroid), nicotinamide ribonucleoside, analogs of nicotinamide ribonucleoside, or a combination thereof.

In some examples, the compounds are gut-selective, non-bile acid FXR agonists.

In some examples, absorption of the compounds is substantially limited to the intestines. In other examples, the compound substantially enhances FXR target gene expression in the intestines while not substantially enhancing FXR target gene expression in the liver or kidney.

In some embodiments, administering the compounds reduces or prevents diet-induced weight gain and/or increases a metabolic rate in the subject. Increasing the metabolic rate may include enhancing oxidative phosphorylation in the subject.

In some embodiments, administering the compounds results in no substantial change in food intake and/or fat consumption in the subject, and/or no substantial change in appetite in the subject. Administering the compounds can protect against diet-induced weight gain, reduce inflammation, enhance thermogenesis, enhance insulin sensitivity in the liver, reduce hepatic steatosis, promote browning of white adipose tissue (WAT), promote activation of brown adipose tissue (BAT), decrease blood glucose, increase weight loss, or any combination thereof. In particular embodiments, administering the compounds enhances insulin sensitivity in the liver and promotes BAT activation.

Exemplary metabolic disorders include but are not limited to: obesity, diabetes (such as a BMI of greater than 25, at least 30, at least 35, or at least 40, such as 25 to 30, 35 to 40, or over 40), insulin resistance, dyslipidemia (such as an elevated serum lipids and/or triglycerides, such as a serum LDL of at least 100 mg/dL, such as at least 130 mg/dL, at least 160 mg/dL or at least 200 mg/dL, such as 100 to 129 mg/dL, 130 to 159 mg/dL, 160 to 199 mg/dL or greater than 200 mg/dL, and/or such as a serum triglyceride of at least of at least 151 mg/dL, such as at least 200 mg/dL, or at least 500 mg/dL, such as 151 to 199 mg/dL, 200 to 499 mg/dL or greater than 499 mg/dL) or any combination thereof. In particular examples, the metabolic disorder is non-insulin dependent diabetes mellitus.

Embodiments of a method for treating or preventing inflammation, such as inflammation in an intestinal region of a subject, are also disclosed. Administering to a subject a therapeutically effective amount of one or more of the disclosed compounds, such as 1, 2, 3, 4, or 5 of such compounds and/or compositions, activates FXR receptors in the intestines, thereby treating or substantially preventing inflammation in the intestinal region of the subject. In some embodiments, the method further includes administering a therapeutically effective amount of an antibiotic (such as metronidazole, vancomycin, and/or fidaxomicin) to the subject, such as to treat or substantially prevent inflammation associated with pseudomembranous colitis in the subject. In other embodiments, the method comprises administering to the subject a therapeutically effective amount of an oral corticosteroid and/or other anti-inflammatory or immunomodulatory therapy in combination with the compound, and/or in combination with an antibiotic.

Intestinal inflammation may be associated with a clinical condition selected from necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis, infectious colitis, or any combination thereof. In certain examples, the one or more FXR target genes comprises IBABP, OSTα, Per1, FGF15, FGF19, or combinations thereof.

Embodiments of a method for treating or preventing cholestatic disorders in subject (such as an adult or pediatric subject) are also disclosed. Administering to a subject a therapeutically effective amount of one or more of the disclosed compounds, or one or more of the disclosed compositions, such as 1, 2, 3, 4, or 5 of such compounds, can be used to treat or prevent a cholestatic disorder in subject. Cholestasis is a condition where bile cannot flow (or flow is significantly reduced) from the liver to the duodenum, for example due to a mechanical blockage (e.g., gallstone, malignancy, or congenital defect), or as a result of a defect in bile formation (e.g., due to a genetic defect, side effect of medication). Examples of such disorders include, but are not limited to, primary biliary cirrhosis (PBC), primary sclerosing cholangitis (PSC), overlap syndrome (PBC plus autoimmune hepatitis), cholestasis resulting from a drug (e.g., one or more of androgen, birth control pills, gold salts, nitrofurantoin, anabolic steroids, chlorpromazine, prochlorperazine, sulindac, cimetidine, estrogen, statins, and antibiotics such as TMP/SMX, flucoxacillin and erythromycin), drug-induced cholestatic hepatitis, total parenteral nutrition (TPN)-induced cholestasis, ICU/sepsis-related cholestasis, obstetric cholestasis, graft vs. host disease, prolonged cholestasis due to hepatitis A, B or C infection, cholestasis due to cystic fibrosis, alcoholic hepatitis, progressive familial intrahepatic cholestasis (PFIC) syndromes, Alagille syndrome, biliary atresia, or any combination thereof. In some embodiments, the method further includes administering a therapeutically effective amount of another therapeutic agent (such as ursodeoxycholic acid, phenobarbital, methotrexate, fat-soluble vitamins, or combinations thereof) to the subject, such as to treat or substantially prevent one or more cholestatic disorders in the subject.

Embodiments of a method for treating or preventing intestinal permeability conditions in subject are also disclosed. Administering to a subject a therapeutically effective amount of one or more of the disclosed compounds, or one or more of the disclosed compositions, such as 1, 2, 3, 4, or 5 of such compounds, can be used to treat or prevent an intestinal permeability condition in subject. Intestinal permeability is a condition where the gut wall exhibits excessive permeability (which some in the field call leaky gut syndrome). Examples of such disorders include, but are not limited to, Crohn's disease, ulcerative colitis, infectious colitis, celiac disease, type 1 diabetes, inflammatory bowel disease, irritable bowel syndrome, or any combination thereof. In some embodiments, the method further includes administering a therapeutically effective amount of another therapeutic agent (such as glutamine, prebiotics, probiotics, *Escherichia coli* Nissle 1917, or combinations thereof) to the subject, such as to treat or substantially prevent one or more intestinal permeability disorders in the subject.

Embodiments of a method for treating or preventing disorder that causes or results from an altered intestinal microbiome in subject are also disclosed. Administering to a subject a therapeutically effective amount of one or more of the disclosed compounds, or one or more of the disclosed compositions, such as 1, 2, 3, 4, or 5 of such compounds, can be used to treat or prevent a disorder resulting altered intestinal microbiome in subject. An altered intestinal microbiome is a condition where the abundance and/or types of bacteria (such as *Bacteriodes. E. coli, Lactobacillus*, and *Bifidobacteria* species) and other microbes (such as yeast) in the intestine are abnormal. Examples of disorders that can have an altered gut microbiome include, but are not limited to, celiac disease, the intestinal permeability conditions described herein, the intestinal inflammation disorders described herein, alcoholic hepatitis, necrotizing enterocolitis, Crohn's disease, ulcerative colitis, intestinal lesions (such as those in a cystic fibrosis patient), cirrhosis, or any combination thereof. In some embodiments, the method further includes administering a therapeutically effective amount of another therapeutic agent (such as a fecal microbiota transplant, immunosuppressant, antibiotic, mesalamine, steroid, altered diet, or combinations thereof) to the subject, such as to treat or substantially prevent one or more disorders resulting from or that causes an altered intestinal microbiome in the subject.

Embodiments of a method for treating an inborn error of metabolism in subject are also disclosed. Administering to a subject a therapeutically effective amount of one or more of the disclosed compounds, or one or more of the disclosed compositions, such as 1, 2, 3, 4, or 5 of such compounds, can be used to treat or prevent an inborn error of metabolism in subject. An inborn error of metabolism is a genetic condition resulting in accumulation of substance which interfere with normal function or the reduced ability to synthesize essential compounds, (such as a reduction in bile acid production, lipid production, or lipid storage). One example of an inborn error of metabolism is cerebrotendinous xanthomatosis (CTX). In some embodiments, the method further includes administering a therapeutically effective amount of another therapeutic agent (such as chenodeoxycholic acid (CDCA), an HMG-CoA reductase inhibitor ("statins" such as simvastatin) or combinations thereof) to the subject, such as to treat an inborn error of metabolism in the subject.

Embodiments of a method for treating or preventing a bile disorder in subject are also disclosed. Administering to a subject a therapeutically effective amount of one or more of the disclosed compounds, or one or more of the disclosed compositions, such as 1, 2, 3, 4, or 5 of such compounds, can be used to treat or prevent a bile disorder in subject. Bile disorders include mechanical biliary obstructions, disorders that result from bile acid malabsorption, and bile acid synthesis disorders. Examples of bile disorders that can be treated with the disclosed compounds include, but are not limited to, benign biliary stricture, malignant biliary obstruction, bile acid diarrhea, or any combination thereof. In some embodiments, the method further includes administering a therapeutically effective amount of another therapeutic agent (such as bile acid sequestrant, cholestyramine, colestipol, farnesoid X receptor agonist (such as obeticholic acid), or combinations thereof) to the subject, such as to treat or prevent a bile disorder in the subject.

Embodiments of a method for treating or preventing a malabsorption disorder (e.g., intestinal malabsorption), such as short bowel syndrome (or symptoms arising from such, such as diarrhea, steatorhea, malnutrition, fatigue, vitamin deficiency), environmental enteropathy, or tropical sprue, in subject are also disclosed. Administering to a subject a therapeutically effective amount of one or more of the disclosed compounds, or one or more of the disclosed compositions, such as 1, 2, 3, 4, or 5 of such compounds, can be used to treat a malabsorption disorder in subject. Short bowel syndrome is a malabsorption disorder causes by surgical removal of the small intestine or dysfunction of a large segment of bowel. Short bowel syndrome can be caused by a birth defect, Crohn's disease, volvulus, tumors, injury, necrotizing enterocolitis, or surgery. Environmental enteropathy is a malabsorption disease believed to be due to frequent intestinal infections, which can result in chronic malnutrition and growth stunting. Tropical sprue is a malabsorption disease found in tropical regions, with abnormal flattening of the villi and inflammation of the small intestine. In some embodiments, the method further includes administering a therapeutically effective amount of another therapeutic agent (such as an anti-diarrheal medicine such as loperamide or codeine, vitamin supplement (such as $B_{12}$ and folic acid), mineral supplement, L glutamine, proton pump inhibitors, lactase, tedulutide (a glucagon-like peptide-2 analog), total parenteral nutrition, antibiotic (e.g., tetracycline or sulfamethoxazole/trimethoprim) or combinations thereof) to the subject, such as to treat or prevent a malabsorption disorder in the subject.

Embodiments of a method for treating or preventing a cell proliferation disease (e.g., cancer, such as adenocarcinoma, such as cancer of the colon, jejunum, and/or ileum), for example in an intestinal region of a subject, are also disclosed. Administering to a subject a therapeutically effective amount of one or more of the disclosed compounds, or one or more of the disclosed compositions, such as 1, 2, 3, 4, or 5 of such compounds and/or compositions, activates FXR receptors in the intestines, thereby treating or substantially preventing a cell proliferation disease, for example in the intestinal region of the subject. In some embodiments, the method further includes administering a therapeutically effective amount of another therapeutic agent, (such as a chemotherapeutic, a biologic, a radiotherapeutic, or combinations thereof) to the subject, such as to treat or substantially prevent a cell proliferation disease in the subject.

In any of the above embodiments, the method may increase HSL phosphorylation and β3-adrenergic receptor expression (such as an increase of at least 20%, at least 25%, at least 30%, at least 40%, at least 50%, at least 75%, or at least 100%). Additionally, the serum concentration of the compound in the subject may remain below its $EC_{50}$ following administration of the compound.

The foregoing and other objects and features of the disclosure will become more apparent from the following detailed description, which proceeds with reference to the accompanying figures.

BRIEF DESCRIPTION OF THE DRAWINGS

This application contains at least one drawing executed in color. Copies of any patent(s) issuing from this application, or patent application publication(s), with color drawing(s) will be provided by the Office upon request and payment of the necessary fee.

FIG. 1A shows FXR target SHP gene expression in FXR abundant tissues including liver, kidney and intestine from 8 week-old mice that were treated with vehicle or fexaramine (100 mg/kg) via oral (PO) or intraperitoneal (IP) injection for three days. FXR target gene expression was analyzed by qPCR. Gene expression was normalized against a vehicle-treated group.

FIG. 1B shows that PO administration of fexaramine (solid bars), but not vehicle (open bars), substantially enhances FXR target gene expression in the intestine, and not in the liver or kidney.

FIG. 1C shows that IP injection of fexaramine increases FXR target gene expression in the liver and kidney, in addition to the intestines. Data represent the mean±SD. Statistical analysis was performed with the Student's t test. *p<0.05, **p<0.01

FIGS. 2A-2G are graphs illustrating the reduction of diet-induced obesity and improvement in metabolic homeostasis with fexaramine Mice were fed a high fat diet (HFD) for 14 weeks and then administered daily oral injections of vehicle (open boxes) or fexaramine (100 mg/kg) (solid boxes) for 5 weeks with HFD. Data represent the mean±STD. Statistical analysis was performed with the Student's t test (*p<0.05, **p<0.01).

FIG. 2A is a line chart illustrating changes in body weight of mice fed a high fat diet (HFD) for 14 weeks and then administered daily oral injections of vehicle (open boxes) or fexaramine (100 mg/kg) (solid boxes) for 5 weeks with HFD. n=8 per group.

FIG. 2B shows mice body weight composition by MRI at the completion of the study.

FIG. 2C shows the wet weight of inguinal fat (iWAT), gonadal fat (gWAT), mesenteric fat (mWAT), liver, kidney, heart and spleen at the completion of the study.

FIG. 2D shows the serum levels (samples were collected after 8 hours-fasting for parameter analysis) of insulin, cholesterol, leptin, resistin and triglycerides.

FIG. 2E shows the serum levels of cytokines at the completion of the study.

FIG. 2F is a line graph representing glucose tolerance testing (GTT), which revealed that fexaramine treatment improved glucose clearance.

FIG. 2G is a line graph representing insulin tolerance testing (ITT), which showed that fexaramine treatment improved insulin sensitivity.

FIG. 3A is a line graph showing hourly composite carbon dioxide production.

FIG. 3B is a line graph showing hourly composite oxygen consumption.

FIG. 3C is a glucose tolerance test.

FIG. 3D is a bar graph showing core body temperature.

FIG. 4C is a line graph showing glucose tolerance tests in mice fed a HFD for 14 weeks and then administered daily oral injections of vehicle or fexaramine (10, 50 or 100 mg/kg) for 5 weeks with HFD. Data represent the mean±STD. Statistical analysis was performed with the Student's t test (*p<0.05, **p<0.01).

FIG. 4D is a line graph showing fasting glucose levels in 14 week HFD-fed mice treated with vehicle or fexaramine (100 mg/kg/day os for 5 week). Data represent the mean±STD. Statistical analysis was performed with the Student's t test (*p<0.05, **p<0.01).

FIGS. 5A-5I show that FXR is required for fexaramine's effects (A) Body weights, (B) glucose tolerance test, (C) insulin tolerance test, (D) oxygen consumption, (E) carbon dioxide production, (F) core body temperature, (G) brown adipose tissue gene expression, (H) liver gene expression, and (I) FXR target gene expressions in ileum of 14 week HFD fed FXR-null mice treated with vehicle or fexaramine (100 mg/kg) for 5 week with HFD. Data represent the mean±SD. Statistical analysis was performed with the Student's t test. *p<0.05, **p<0.01.

FIGS. 6A-6J demonstrate that fexaramine increases OXPHOS to enhance metabolic rate in brown adipose tissue. Mice were fed HFD for 14 weeks and then administered vehicle or fexaramine (100 mg/kg) daily by oral administration for 5 weeks with HFD. Data represent the mean±STD. Statistical analysis was performed with the Student's t test (*p<0.05, **p<0.01).

FIG. 6A is a bar chart showing daily food intake during the first week treatment.

FIG. 6B is a line chart showing carbon dioxide production.

FIG. 6C is a line chart showing oxygen consumption.

FIG. 6D is a bar chart showing daytime and nighttime cumulative ambulatory counts.

FIG. 6E is a bar chart showing core body temperature.

FIG. 6F shows hematoxyin and eosin staining of brown adipose tissue (BAT) for histological analysis.

FIG. 6G is a bar chart showing relative gene expression of nuclear receptors and other genes encoding proteins involved in mitochondrial biogenesis, glucose transport and FA oxidation in BAT.

FIG. 6H is a set of digital images of gel electrophoreses showing protein expression levels of total and phosphorylated p38 in BAT. RalA levels are shown as a loading control.

FIG. 6I is a bar chart showing the relative levels of phosphorylated p38 in BAT after vehicle (open bar) or Fexaramine administration (solid bar).

FIG. 6J is a chart showing changes in relative expression of OXPHOS genes based on RNA-sequencing transcriptomic analysis in inguinal fat (iWAT), gonadal fat (gWAT) and brown fat (BAT) after vehicle or fexaramine treatment.

FIG. 6K is a heatmap depiction of changes in genes involved in chemokine and cytokine signaling in BAT after vehicle or fexaramine treatment.

FIG. 6L is a bar graph showing PKA activity in BAT. Data represent the mean±SD. Statistical analysis was performed with the Student's t test. *p<0.05, **p<0.01.

FIG. 6M is a bar chart showing the effect of fexaramine on respiratory exchange ratio (RER). Mice were fed on HFD for 14 weeks, and then administered daily oral injections of vehicle (solid bar) or fexaramine (100 mg/kg) (open bar) for 5 weeks with HFD. No changes were observed in respiratory exchange ratio by fexaramine treatment.

FIG. 6N is a bar graph showing the effect of fexaramine administration on serum lactate concentrations. Mice were fed on HFD for 14 weeks, and then administered daily oral injections of vehicle (left bar) or fexaramine (100 mg/kg) (right bar) for 5 weeks with HFD. Serum lactate levels were found to be significantly decreased with fexaramine treatment. Data represent the mean±STD. Statistical analysis was performed with the Student's t test (*p<0.05, **p<0.01).

FIGS. 7A-7H show a comparative expression chart and bar charts illustrating that fexaramine increased endogenous FGF15 signaling and changes in BA composition. Mice were fed HFD for 14 weeks and then administered daily oral injections of vehicle or fexaramine (100 mg/kg) for 5 weeks with HFD. In the bar graphs, open bars represent vehicle treatment and solid bars represent fexaramine treatment, and data represent the mean±STD. Statistical analysis was performed with the Student's t test (*p<0.05, **p<0.01).

FIG. 7A is a heatmap depicting changes in expression of ileal FXR target genes following PO fexaramine administration.

FIG. 7B is a bar chart showing FGF15 protein levels from ileal extract.

FIG. 7C is a bar chart showing FGF15 protein levels in the serum.

FIG. 7D is a bar chart showing changes in the expression of hepatic genes involved in bile acid metabolism.

FIG. 7E is a bar chart showing total serum bile acid (BA) levels.

FIG. 7F is a bar chart showing composition ratios of bile acids. The ratio of unconjugated to conjugated cholic acid was remarkably increased by fexaramine FIG. 7G is a bar chart showing changes in intestinal permeability.

FIG. 7H is a bar chart showing changes in expression of intestinal genes involved in mucosal defense.

FIG. 9 is a bar graph showing that fexaramine fails to activate TGR5. HEK293 cells were transfected with expression vectors for cAMP-response element luciferase, β-galactosidase and human TGR5. 24 hours after transfection, cells were treated with fexaramine or INT-777 (a TGR5 agonist).

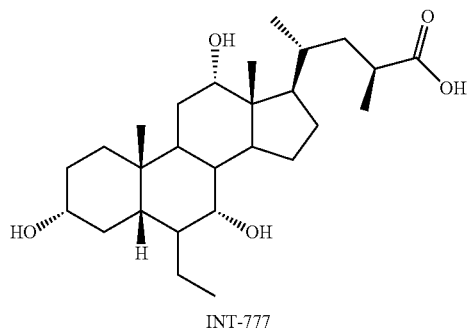 [SMILES: CCC1[C@@H](O)C2C3CC[C@H]([C@H](C)C[C@H](C)C(=O)O)[C@@]3(C)[C@@H](O)CC2[C@@]2(C)CC[C@@H](O)C[C@@H]12]

INT-777

FIGS. 10A-10F show that systemic TGR5 activation is required to affect glucose homeostasis. HFD-fed mice were treated with vehicle, the intestinally-restricted TGR5 ligand L755-0379 (A, L755, 100 mg/kg, EC50 300 nM) or the systemic ligand RO5527239 (B, RO, 100 mg/kg. EC50 70 nM) via per os for 14 days. C, Plasma L755 concentrations in portal and tail veins after PO administration. D, Body weight curve. E, Glucose tolerance test. F, Serum insulin levels after a glucose challenge (vehicle left bar, RO middle bar, L755 right bar). Data represent the mean±SD. Statistical analysis was performed with the Student's t test. *p<0.05, **p<0.01.

Figure 11A:
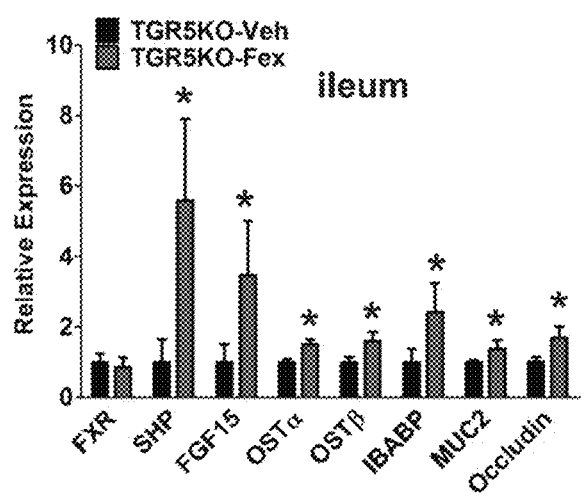
Figure 11B:
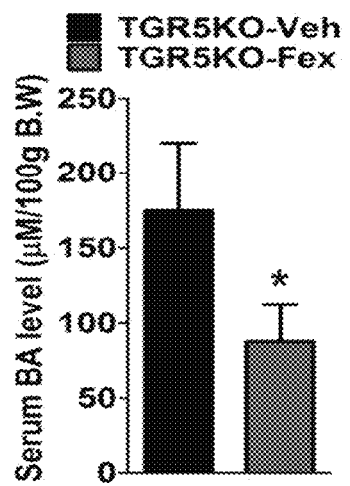
Figure 11C:
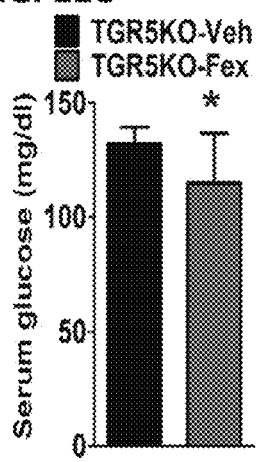
Figure 11D:
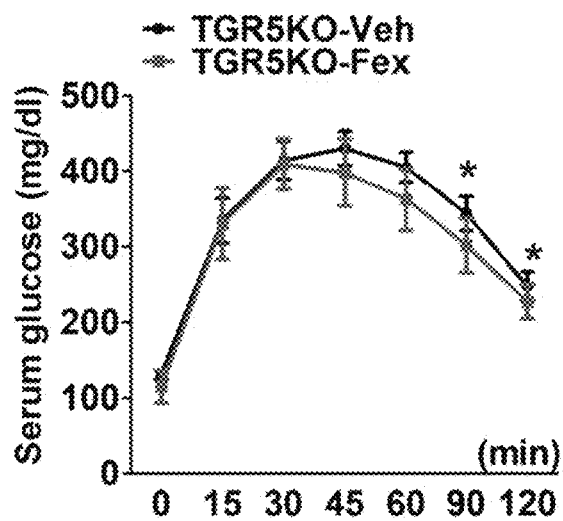
Figure 11M:
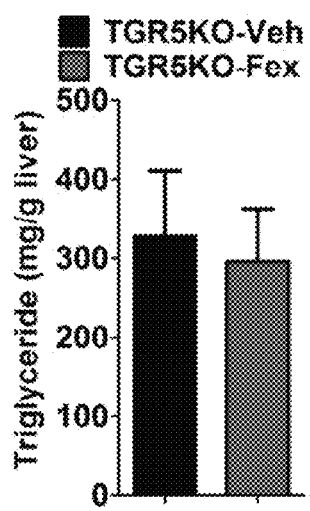
Figure 11N:
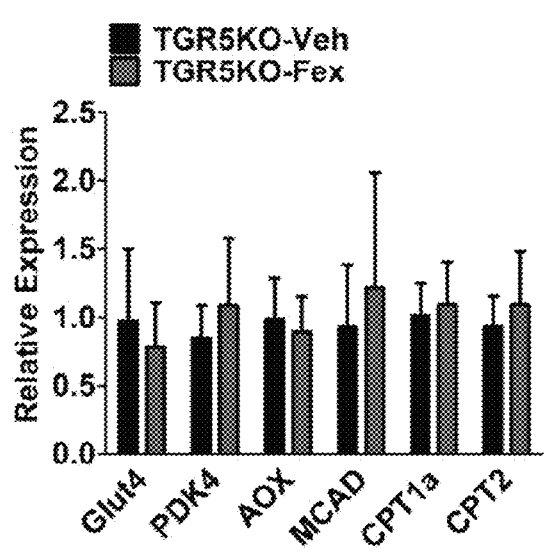

FIGS. 11A-11N show that TGR5 is required for a subset of fexaramine's effects. HFD-fed TGR5-null mice were treated with vehicle or fexaramine (100 mg/kg os daily for 5 weeks with HFD, n=10). (A) Ileal FXR target gene expressions (B) Serum BA levels (C) Fasting glucose levels (D) Glucose tolerance test (E) Core body temperature (F) Oxygen consumption rate (G) Carbon dioxide production (H) Gene expression in BAT (I) Body weight curve (J) Body composition by MRI (K) Insulin Tolerance Test (L) Hepatic gene expression (M) Hepatic TG levels (N) and Gene expression in soleus of TGR5 knockout mice with and without fexaramine treatment. For bar graphs, vehicle is left bar, Fex is right bar. Data represent the mean±SD. Statistical analysis was performed with the Student's t test. *p<0.05, **p<0.01.

FIGS. 12A-12H demonstrate that fexaramine reduces inflammation and increases lipolysis in adipose tissues. Mice were fed on HFD for 14 weeks and subsequently subjected to daily PO injection of vehicle or fexaramine (100 mg/kg) for 5 weeks with HFD. In the bar graphs, open bars are vehicle, solid bars of fexaramine, and data represent the mean±STD. Statistical analysis was performed with the Student's t test (*p<0.05, **p<0.01).

Figure 12A:
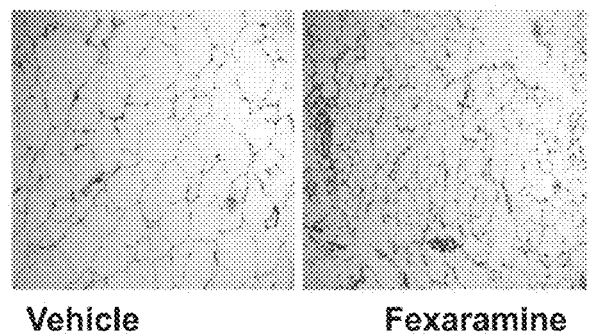

FIG. 12A shows histological sections of mesenteric white adipose tissues from vehicle and fexaramine-treated mice.

Figure 12B:
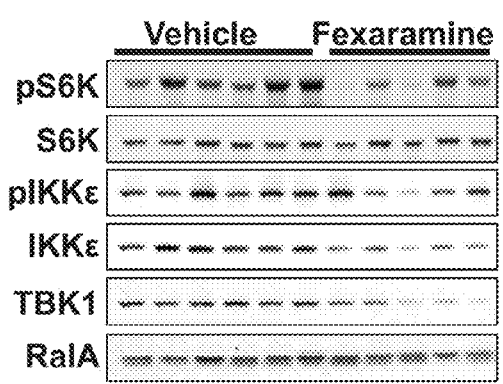

FIG. 12B is a set of photographs of gel electrophoreses showing protein expression levels of TBK1, and total and phosphorylated IKKε and S6K, in gonadal adipose tissues (gWAT) from vehicle or fexaramine-treated mice.

Figure 12C:
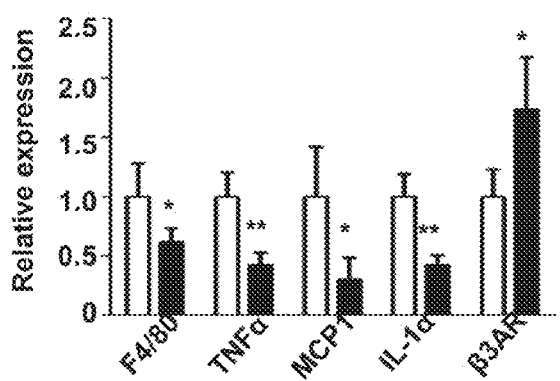

FIG. 12C is a bar chart showing relative gene expression levels of β-3-adrenergic receptor and various cytokines in gonadal adipose tissue. Vehicle open bar, Fex solid bar.

Figure 12D:
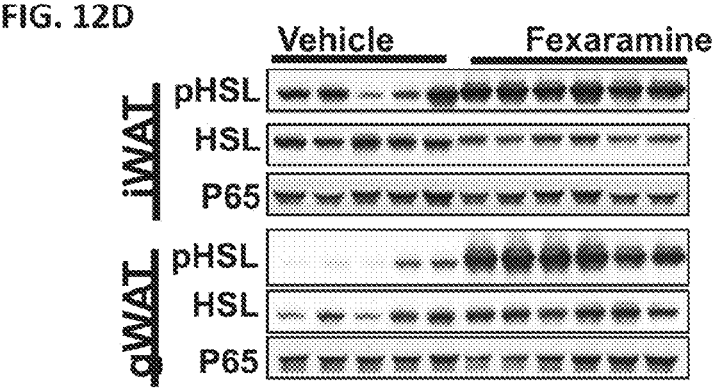

FIG. 12D is a set of photographs of gel electrophoreses showing protein expression levels of total and phosphorylated HSL (p-HSL) and p65 in gonadal and inguinal adipose tissues.

Figure 12E:
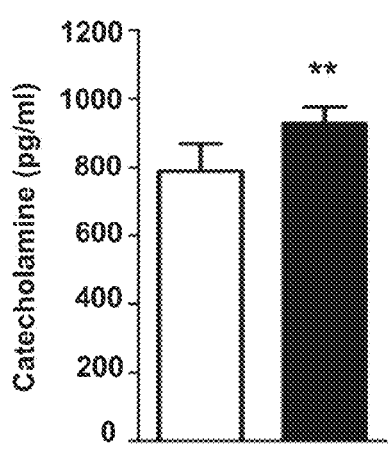

FIG. 12E is a bar chart showing serum levels of catecholamines, in vehicle or fexaramine-treated mice. Vehicle open bar, Fex solid bar.

Figure 12F:
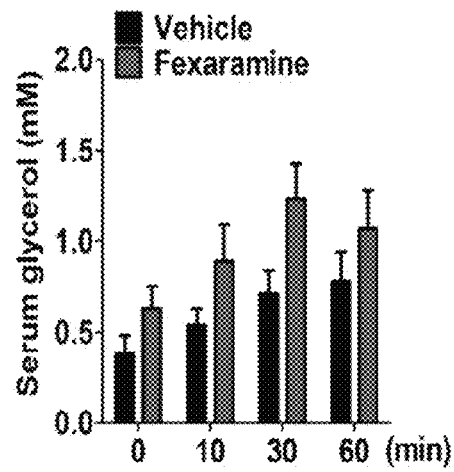

FIG. 12F is a bar chart showing serum glycerol levels, in vehicle or fexaramine-treated mice. Isoproterenol (1 µg/kg) was injected at 0 minutes and free glycerol levels were measured at the indicated time points. Vehicle left bar, Fex right bar.

Figure 12G:
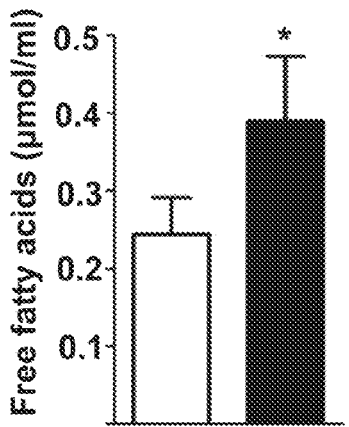

FIG. 12G is a bar chart showing serum levels of free fatty acids in vehicle or fexaramine-treated mice. Data represent the mean±STD. Statistical analysis was performed with the Student's t test (*p<0.05, **p<0.01). Vehicle open bar, Fex solid bar.

Figure 12H:
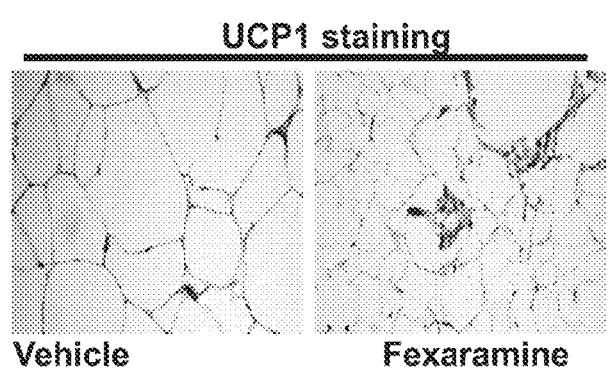

FIG. 12H shows UCP1 staining of brown fat-like cells in inguinal adipose tissues (iWAT) from vehicle or fexaramine-treated mice (Magnification:100×).

Figure 12I:
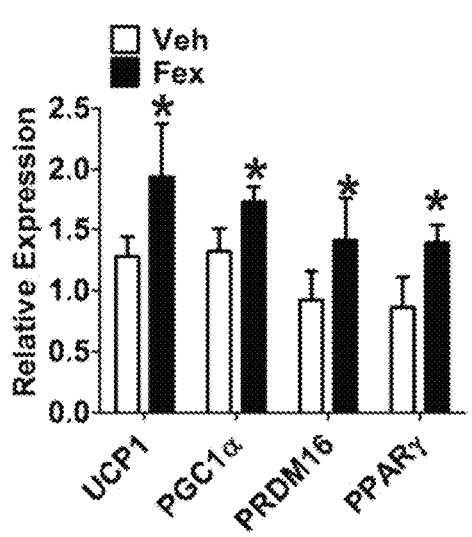
Figure 12J:
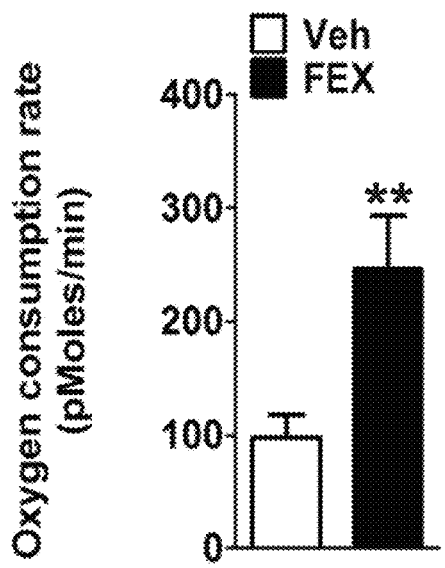

FIGS. 12I and 12J show that fexaramine enhances OXPHOS in iWAT. Mice fed a HFD for 14 weeks were maintained on a HFD and treated with vehicle or fexaramine (100 mg/kg/day os for 5 week). (I) Changes in genes associated with the browning of adipose tissue and (J) oxygen consumption rate of the stromal vascular fraction (SVF) from inguinal fat (iWAT). Data represent the mean±SD. Statistical analysis was performed with the Student's t test. *p<0.05, **p<0.01.

Figure 13:
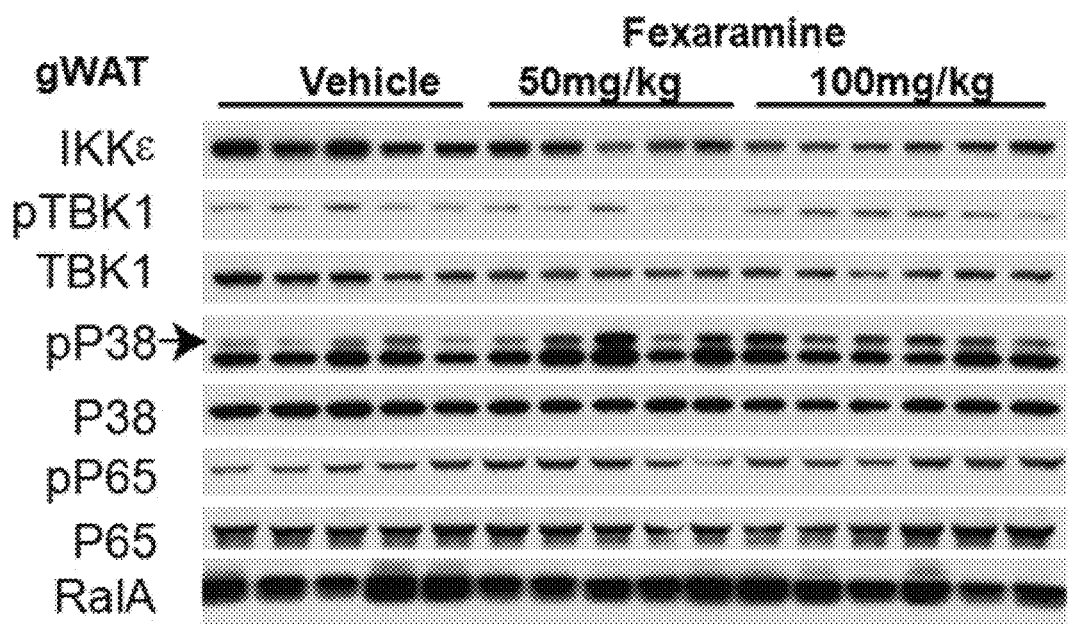

FIG. 13 is a set of digital images of gel electrophoreses (Western blots) showing the level of expression of various proteins in gonadal white adipose tissue (gWAT). Mice fed a HFD for 14 weeks were maintained on a HFD and treated with vehicle or fexaramine (50 mg or 100 mg/kg/day os for 5 week).

Figure 14:
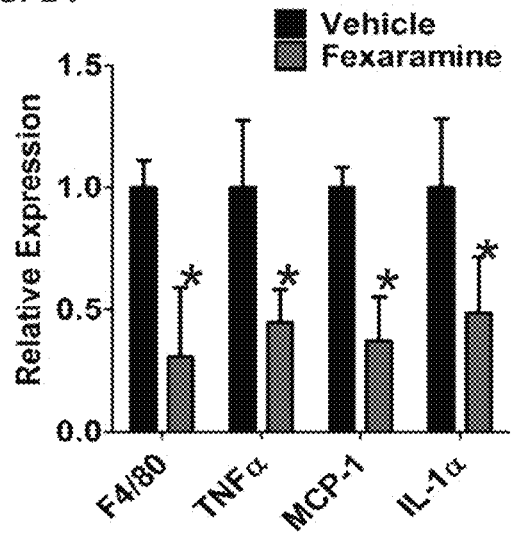

FIG. 14 is a bar chart showing that fexaramine reduces brown adipose tissue (BAT) inflammation. Mice fed a HFD for 14 weeks were maintained on a HFD and treated with vehicle or fexaramine (100 mg/kg/day os for 5 week). Expression of inflammatory cytokines in BAT. Data represent the mean±SD. Statistical analysis was performed with the Student's t test. *p<0.05, **p<0.01.

FIGS. 15A-15H are a set of histology stains and bar charts demonstrating that fexaramine induced less weight gain and improved glucose homeostasis relative to mice that did not receive fexaramine. Mice were fed HFD for 14 weeks and then subjected to daily PO injection of vehicle (open bar in bar graphs) or fexaramine (100 mg/kg) (solid bar in bar graphs) for 5 weeks with HFD.

Figure 15A:
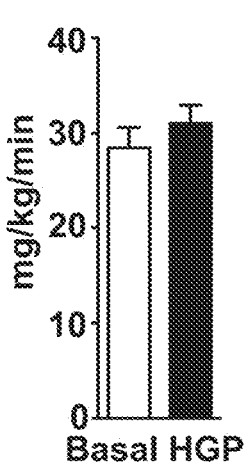

FIG. 15A is a bar chart showing basal hepatic glucose production (HGP).

Figure 15B:
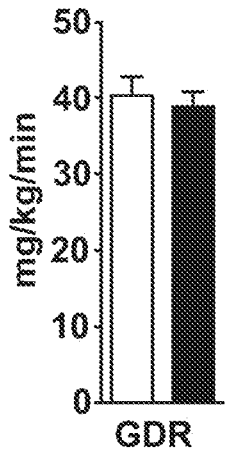

FIG. 15B is a bar chart showing glucose disposal rate (GDR).

Figure 15C:
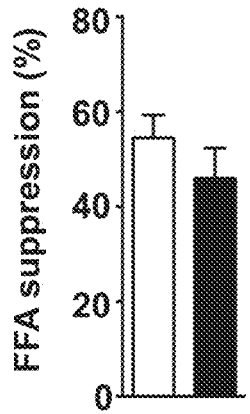

FIG. 15C is a bar chart showing percentage free fatty acid (FFA) suppression by insulin.

Figure 15D:
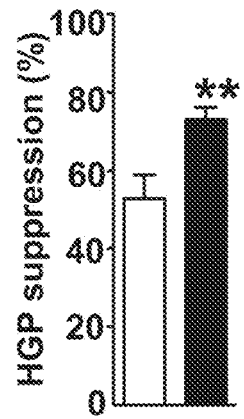

FIG. 15D is a bar chart showing HGP suppression by insulin, as measured by hyperinsulinemic-euglycemic clamps.

Figure 15E:
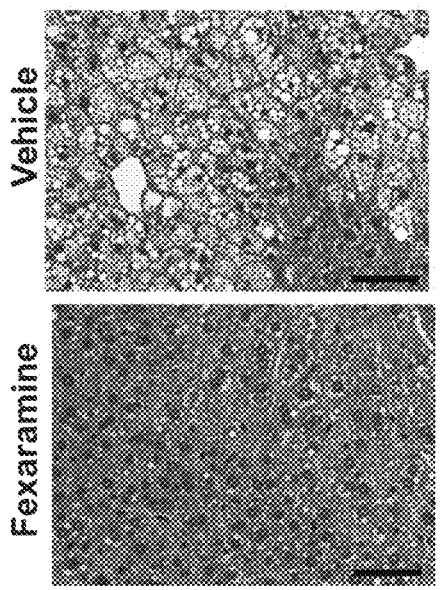

FIG. 15E shows hematoxylin and eosin staining for liver histology.

Figure 15F:
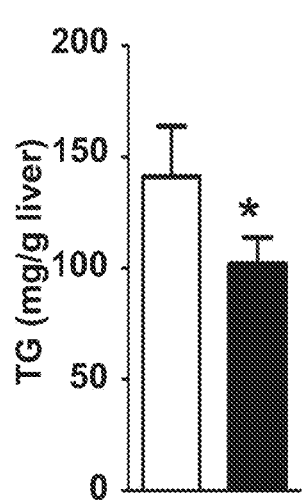

FIG. 15F is a bar chart showing triglyceride levels in the liver.

Figure 15G:
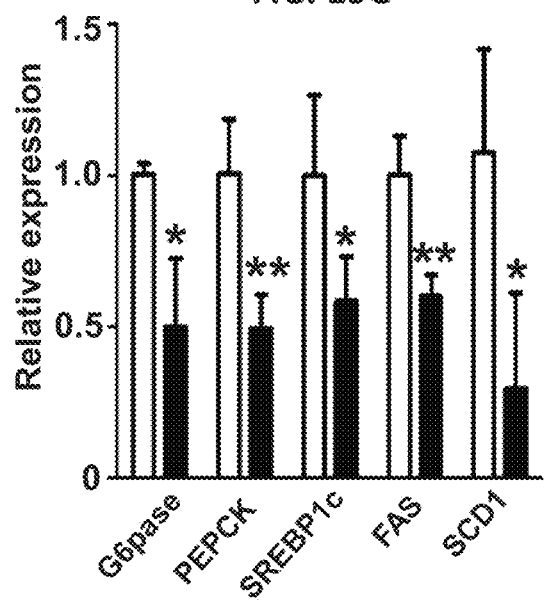

FIG. 15G is a bar chart showing hepatic gene expression levels for genes involved in gluconeogenesis and lipogenesis.

Figure 15H:
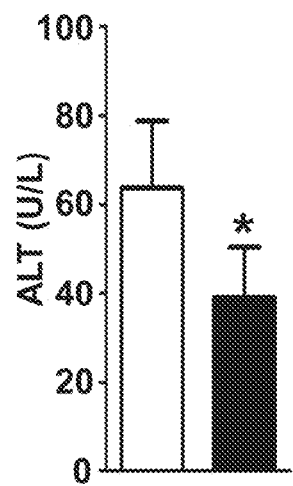

FIG. 15H is a bar chart showing serum levels of alanine aminotransferase (ALT). Vehicle open bar, Fex, solid bar.

Figure 15I:
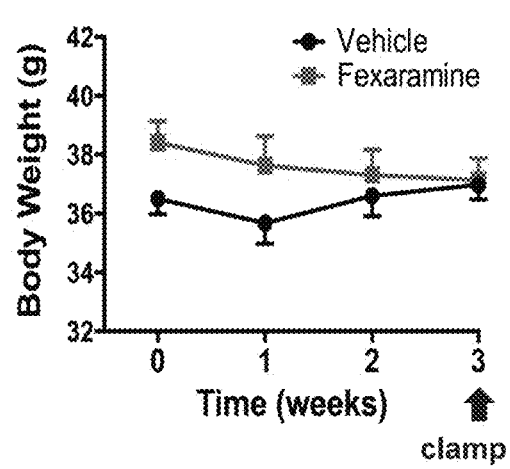
Figure 15J:
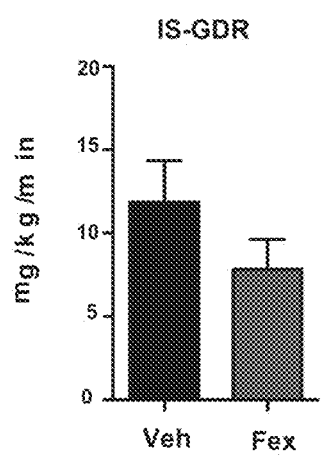
Figure 15K:
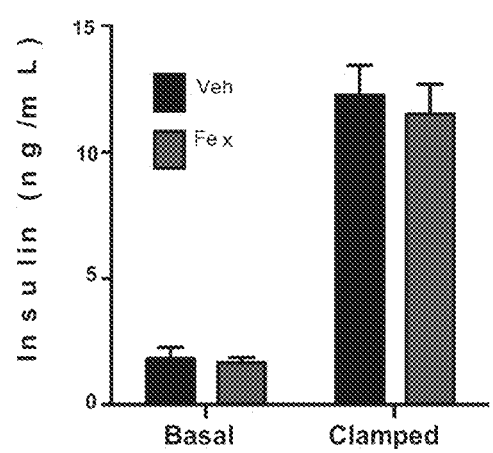

FIGS. 15I-15K are a line graph and two bar graphs showing the effect of fexaramine treatment on body weight, insulin-stimulated GDR, and fasting insulin levels. Mice were fed HFD for 14 weeks, and then administered daily oral injections of vehicle or fexaramine (100 mg/kg) for 3 weeks with HFD. The mice treated with fexaramine were initially heavier (by 2-3 grams). Three weeks after treatment, a clamp study was performed on the mice. Data represent the mean±STD. Statistical analysis was performed with the Student's t test (*$p<0.05$, **$p<0.01$).

FIG. 15I is a line graph showing the changes in body weight for the two groups of mice. Vehicle bottom line, Fex, top line.

FIG. 15J is a bar chart showing the insulin-stimulated GDR (IS-GDR). Vehicle left bar, Fex, right bar.

FIG. 15K is a bar chart showing the fasting insulin levels. Vehicle left bar, Fex, right bar.

SEQUENCE LISTING

The amino acid sequences are shown using standard three letter code for amino acids, as defined in 37 C.F.R. 1.822.

SEQ ID NO. 1 is a protein sequence of GLP-1-(7-36).
SEQ ID NO. 2 is a protein sequence of GLP-2.

DETAILED DESCRIPTION

I. Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a FXR agonist" includes single or plural FXR agonists and is considered equivalent to the phrase "comprising at least one FXR agonist." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank® Accession Nos. referred to herein are the sequences available at least as early as Mar. 13, 2014. All references, including patents and patent applications, and GenBank® Accession numbers cited herein, are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

A wavy line "∽" or "∼" or an arrow "→" denoted a point of attachment of a group or moiety to the parent structure.

"Aliphatic" refers to a substantially hydrocarbon-based compound, or a radical thereof (e.g., $C_6H_{13}$, for a hexane radical), including alkanes, alkenes, alkynes, including cyclic versions thereof, such as alkyl, alkenyl, alkynyl, cycloalkyl, cycloalkenyl, and cycloalkynyl, and further including straight- and branched-chain arrangements, and all stereo and position isomers as well. Unless expressly stated otherwise, an aliphatic group contains from one to at least twenty-five carbon atoms; for example, from one to fifteen, from one to ten, from one to six, or from one to four carbon atoms. The term "lower aliphatic" refers to an aliphatic group comprising from one to ten carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene [—$CH_2$—] carbon in an aliphatic chain, or up to one substituent for each carbon of a —C═C— double bond in an aliphatic chain, or up to one substituent for a carbon of a terminal methine group). Exemplary aliphatic substituents include, for instance, amino, amide, sulfonamide, halo, cyano, carboxy, hydroxyl, mercapto, trifluoromethyl, alkyl, alkoxy, acetoxy, alkylthio, thioalkoxy, arylalkyl, heteroaryl, alkylamino, dialkylamino, or other functionality.

"D-aliphatic" refers to an aliphatic group where at least one hydrogen has been substituted by deuterium.

"Amino" refers to the group —NR'R", wherein R' and R" independently are selected from hydrogen, aliphatic, D-aliphatic, heteroaliphatic or D-heteroaliphatic, or where R' and R" are optionally joined together with the nitrogen bound thereto to form a cycloamino group such as a heterocyclic, deuterated heterocyclic, heteroaryl or deuterated heteroaryl group comprising at least one ring nitrogen. Exemplary cycloamino groups include, but are not limited to, pyrrolidine, pyrrole, imidazole, triazole, tetrazole, piperidine, triazinane, piperazine, morpholine, azepane, diazepane, azocane, diazocane, azonane or azecane.

The term "aminocarbonyl" refers to a chemical functional group —C(═O)-amino, where amino is as defined herein. A primary aminocarbonyl is —$CONH_2$.

The term "cyano" refers to the chemical functional group —CN.

The term "carboxyl," "carboxylic acid" or "carboxy" refers to the chemical functional group —$CO_2H$.

The term "carboxyl ester," "carboxylic acid ester," or "carboxy ester" refers to the chemical functional group —$CO_2R$ where R is aliphatic, D-aliphatic, heteroaliphatic or D-heteroaliphatic.

The term "aminosulfonyl" refers to a chemical function group —$SO_2$-amino, where amino is as defined herein. A primary aminosulfonyl is —$SO_2NH_2$.

The term "acyl" means, unless otherwise stated, —C(O)R where R is aliphatic, D-aliphatic, heteroaliphatic or D-heteroaliphatic.

The term "aryl" or "Ar" refers to a monovalent aromatic carbocyclic group of from 6 to 15 carbon atoms having a single ring (e.g., phenyl) or multiple condensed rings (e.g., naphthyl or anthryl) in which at least one of the condensed rings is aromatic (e.g., 2-benzoxazolinone, 2H-1,4-benzoxazin-3(4H)-one-7-yl, 9,10-dihydrophenanthrene, and the like), provided that the point of attachment is through an atom of the aromatic aryl group. Unless otherwise specified, the aryl group may be optionally substituted. Preferred aryl groups include phenyl and naphthyl.

"Heteroaliphatic" refers to an aliphatic compound or group having at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched, cyclic or acyclic, and include "heterocycle", "heterocyclyl", "heterocycloaliphatic", or "heterocyclic" groups. Examples of heterocycles include morpholine and piperidine.

"D-heteroaliphatic" refers to a heteroaliphatic group where at least one hydrogen has been substituted by a deuterium.

"Halo", "halide" or "halogen" refers to fluoro, chloro, bromo, and iodo, and is preferably fluoro or chloro.

"Heteroaryl" refers to an aromatic group having from 1 to 15 carbon atoms and at least one, and more typically 1 to 4, heteroatoms selected from oxygen, nitrogen or sulfur within the ring. Unless otherwise specified, the heteroaryl group may be optionally substituted. Such heteroaryl groups can have a single ring (e.g., pyridinyl, imidazolyl or furyl) or multiple condensed rings (e.g., indolizinyl, quinolinyl, benzimidazolyl, benzopyrazolyl or benzothienyl), wherein at least one of the condensed rings is aromatic and may or may not contain a heteroatom, provided that the point of attachment is through an atom of an aromatic ring. In one embodiment, the nitrogen and/or sulfur ring atom(s) of the heteroaryl group are optionally oxidized to provide N-oxide (N→O), sulfinyl, or sulfonyl moieties. Preferred heteroaryls include pyridinyl, pyrrolyl, indolyl, thiophenyl, benzopyrazolyl and furanyl.

"Sulfonyl" refers to the group —$SO_2$—, and includes —$SO_2$-aliphatic, —$SO_2$-aryl, —$SO_2$-heteroaryl, or —$SO_2$-heterocyclic, wherein aliphatic, aryl, heteroaryl, and heterocyclic are as defined herein. Sulfonyl includes groups such as methyl-$SO_2$—, phenyl-$SO_2$—, and 4-methylphenyl-$SO_2$—.

The terms "carboxyl bioisosteric," or "carboxyl bioisostere" refer to a group with similar physical or chemical properties to a carboxyl groupthat produce broadly similar biological properties, but which may reduce toxicity or modify the activity of the compound, and may alter the metabolism of the compound. Exemplary carboxyl bioisosteres include, but are not limited to,

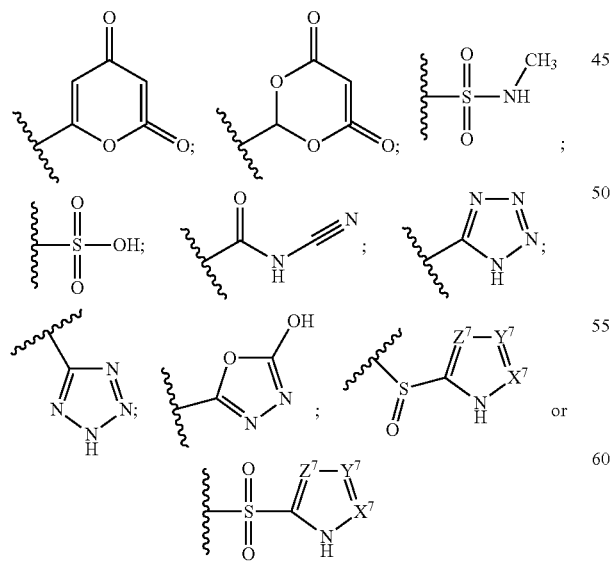

where $X^7$, $Y^7$, and $Z^7$ are each independently selected from N, $CH_2$ or CO;

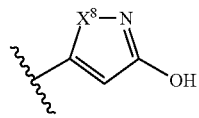

where $X^8$ is selected from O, S or NMe;

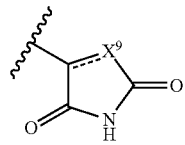

where $X^9$ is selected from O, N, S, CH or $CH_2$;

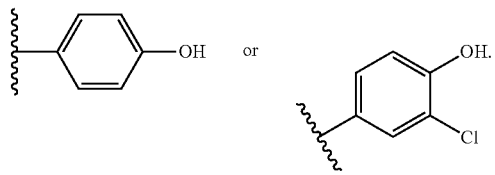 [SMILES: *c1ccc(O)cc1 ; "or" ; *c1ccc(O)c(Cl)c1]

Additional carboxyl bioisosteric groups contemplated by the present disclosure include

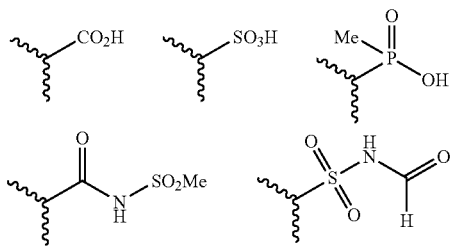

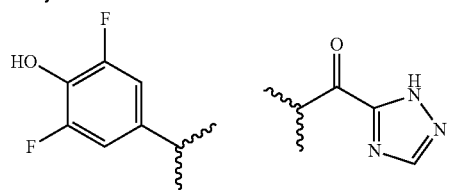

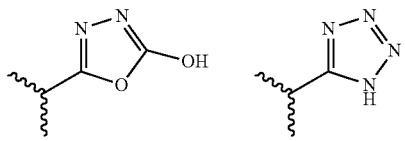

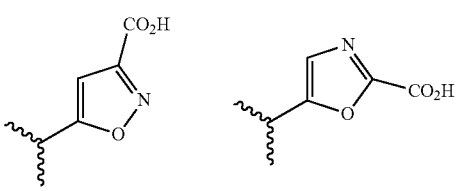

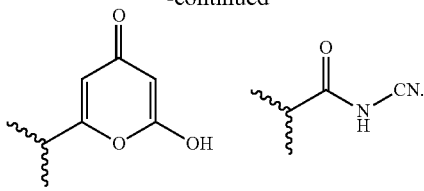

In a preferred embodiment, a group that is substituted has 1 substituent, 1 or 2 substituents, 1, 2, or 3 substituents or 1, 2, 3 or 4 substituents.

Also, it is understood that the above definitions are not intended to include impermissible substitution patterns. Such impermissible substitution patterns are understood by a person having ordinary skill in the art.

Additionally, it is understood by a person of ordinary skill in the art that if an atom does not appear to have sufficient specific bonds to satisfy valence requirements, such as an apparent trivalent carbon, there are sufficient implicit hydrogens present to satisfy those valence requirements.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like. If the molecule contains a basic functionality, pharmaceutically acceptable salts include salts of organic or inorganic acids, such as hydrochloride, hydrobromide, tartrate, mesylate, acetate, maleate, oxalate, and the like.

"Pharmaceutically acceptable excipient" refers to a substantially physiologically inert substance that is used as an additive in a pharmaceutical composition. As used herein, an excipient may be incorporated within particles of a pharmaceutical composition, or it may be physically mixed with particles of a pharmaceutical composition. An excipient can be used, for example, as a carrier, flavoring agent, thickener, diluent, buffer, preservative, or surface active agent and/or to modify properties of a pharmaceutical composition. Examples of excipients include, but are not limited, to polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

"Enteric coating" refers to a coating such as may be applied to disclosed compounds or compositions comprising the compounds to help protect drugs from disintegration, digestion etc. in the stomach, such as by enzymes or the pH of the stomach. Typically, the coating helps prevent the drug from being digested in the stomach, and allows delivery of the medication to the intestine.

The terms "administer," "administering", "administration," and the like, as used herein, refer to methods that may be used to enable delivery of agents or compositions to the desired site of biological action. These methods include, but are not limited to oral routes, intraduodenal routes and rectal administration. Administration techniques that are optionally employed with the agents and methods described herein are found in sources e.g., Goodman and Gilman, The Pharmacological Basis of Therapeutics, current ed.; Pergamon; and Remington's, Pharmaceutical *Sciences* (current edition), Mack Publishing Co., Easton, Pa. In certain embodiments, the agents and compositions described herein are administered orally.

The term "calorie" refers to the amount of energy, e.g. heat, required to raise the temperature of 1 gram of water by 1° C. In various fields such as medicine, nutrition, and the exercise sciences, the term "calorie" is often used to describe a kilocalorie. A kilocalorie is the amount of energy needed to increase the temperature of 1 kilogram of water by 1° C. One kilocalorie equals 1000 calories. The kilocalorie is abbreviated as kc, kcal or Cal, whereas the calorie or gram calorie is abbreviated as cal. In some embodiments, food intake in the subject is measured in terms of overall calorie consumption. Likewise, in some embodiments, fat intake can be measured in terms of calories from fat.

As used herein, the terms "co-administration," "administered in combination with," and their grammatical equivalents, are meant to encompass administration of the selected therapeutic agents to a single patient, and are intended to include treatment regimens in which the agents are administered by the same or different route of administration or at the same or different times. In some embodiments the agents described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the agents described herein and the other agent(s) are administered in a single composition. In some embodiments, the agents described herein and the other agent(s) are admixed in the composition.

The terms "effective amount," "pharmaceutically effective amount" or "therapeutically effective amount" as used herein, refer to a sufficient amount of at least one agent being administered to achieve a desired result, e.g., to relieve to some extent one or more symptoms of a disease or condition being treated. In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case can be determined using any suitable technique, such as a dose escalation study.

"Enhancing enteroendocrine peptide secretion" refers to a sufficient increase in the level of the enteroendocrine peptide agent to, for example, decrease hunger in a subject, to curb appetite in a subject and/or decrease the food intake of a subject or individual and/or treat any disease or disorder described herein.

"FXR": farnesoid X receptor (also known as nuclear receptor subfamily 1, group H, member 4 (NR1H4)) (OMIM: 603826): This protein functions as a receptor for bile acids, and when bound to bile acids, regulates the expression of genes involved in bile acid synthesis and transport. FXR is expressed at high levels in the liver and intestine. Chenodeoxycholic acid and other bile acids are natural ligands for FXR. Similar to other nuclear receptors, when activated, FXR translocates to the cell nucleus, forms a dimer (in this case a heterodimer with RXR) and binds to hormone response elements on DNA, which up- or down-regulates the expression of certain genes. One of the primary functions of FXR activation is the suppression of cholesterol 7 alpha-hydroxylase (CYP7A1), the rate-limiting enzyme in bile acid synthesis from cholesterol. FXR does not directly bind to the CYP7A1 promoter. Rather, FXR induces expression of small heterodimer partner (SHP), which then functions to inhibit transcription of the CYP7A1 gene. In this way, a negative feedback pathway is established in which synthesis of bile acids is inhibited when cellular levels are already high. FXR sequences are publically available, for example from GenBank® sequence database (e.g., accession numbers NP_001193906 (human, protein) and NP_001156976 (mouse, protein), and NM_001206977 (human, nucleic acid) and NM_001163504 (mouse, nucleic acid)).

The term "metabolic disorder" refers to any disorder that involves an alteration in the normal metabolism of carbohydrates, lipids, proteins, nucleic acids or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, but are not limited to, the endocrine (hormonal) control system (e.g., the insulin pathway, the enteroendocrine hormones including GLP-1, GLP-2, oxyntomodulin, PYY or the like), the neural control system (e.g., GLP-1 in the brain) or the like. Examples of metabolic disorders include and are not limited to diabetes, insulin resistance, dyslipidemia, metabolic syndrome, or the like.

The term "metabolic rate" refers to the rate at which the subject uses energy. This is also known as the rate of metabolism, or the rate of energy consumption, and reflects the overall activity of the individual's metabolism. The term basal metabolism refers to the minimum amount of energy required to maintain vital functions in an individual at complete rest, measured by the basal metabolic rate in a fasting individual who is awake and resting in a comfortably warm environment. The term "basal metabolic rate" refers to the rate at which energy is used by an individual at rest. Basal metabolic rate is measured in humans by the heat given off per unit time, and expressed as the calories released per kilogram of body weight or per square meter of body surface per hour. The heart beating, breathing, maintaining body temperature, and other basic bodily functions all contribute to basal metabolic rate. Basal metabolic rate can be determined to be the stable rate of energy metabolism measured in individuals under conditions of minimum environmental and physiological stress, or essentially at rest with no temperature change. The basal metabolic rate among individuals can vary widely. One example of an average value for basal metabolic rate is about 1 calorie per hour per kilogram of body weight.

The terms "non-systemic" or "minimally absorbed" as used herein refer to low systemic bioavailability and/or absorption of an administered compound. In some instances a non-systemic compound is a compound that is substantially not absorbed systemically. In some embodiments, FXR agonist compositions described herein deliver an FXR agonist to the distal ileum, colon, and/or rectum and not systemically (e.g., a substantial portion of the FXR agonist administered is not systemically absorbed). In some embodiments, the systemic absorption of a non-systemic compound is <0.1%, <0.3%, <0.5%, <0.6%, <0.7%, <0.8%, <0.9%, <1%, <1.5%, <2%, <3%, or <5% of the administered dose (wt. % or mol %). In some embodiments, the systemic absorption of a non-systemic compound is <15% of the administered dose. In some embodiments, the systemic absorption of a non-systemic compound is <25% of the administered dose. In an alternative approach, a non-systemic FXR agonist is a compound that has lower systemic bioavailability relative to the systemic bioavailability of a systemic FXR agonist. In some embodiments, the bioavailability of a non-systemic FXR agonist described herein is <30%, <40%, <50%, <60%, or <70% of the bioavailability of a systemic FXR agonist. In some embodiments, the serum concentration of the FXR agonist in the subject remains below the compound's $EC_{50}$ following administration.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to a patient at risk of developing a particular disease, to a patient reporting one or more of the physiological symptoms of a disease, or to a patient at risk of reoccurrence of the disease.

The term "subject", "patient" or "individual" may be used interchangeably herein and refer to mammals and non-mammals, e.g., suffering from a disorder described herein. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, amphibians, and the like. In one embodiment of the methods and compositions provided herein, the mammal is a human.

The terms "treat," "treating" or "treatment," and other grammatical equivalents as used herein, include alleviating, inhibiting or reducing symptoms, reducing or inhibiting severity of, reducing incidence of, prophylactic treatment of, reducing or inhibiting recurrence of, preventing, delaying onset of, delaying recurrence of, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. Therapeutic benefit means eradication or amelioration of the underlying disorder being treated, and/or the eradication or amelioration of one or more of the physiological symptoms associated with the underlying disorder, such that an improvement is observed in the patient.

II. Overview

Disclosed herein are compounds that have activity as FXR agonists that are structurally distinct from bile acids, other synthetic FXR ligands, and other natural FXR ligands. Also disclosed herein are embodiments of a method for treating or preventing inflammation in the intestines and/or a metabolic disorder, such as diabetes or obesity, by administering a therapeutically effective amount of an FXR agonist to the GI tract of a subject, such as one of the novel FXR agonists disclosed herein. Also disclosed herein are methods for treating or preventing a cell proliferative disorder, such as cancer, for example in the intestine, by administering a therapeutically effective amount of an FXR agonist to the subject (e.g., to the GI tract), such as one of the novel FXR agonists disclosed herein.

The absorption of these FXR agonists may be substantially restricted to the intestinal lumen when delivered orally.

In various embodiments, administration of one or more of the disclosed FXR agonists may result in activation of FXR transcriptional activity in the intestine, without substantially affecting other target tissues, such as liver or kidney. Despite this restricted activity, chronic administration with these agonists may lead to beneficial body-wide effects in obese subjects. The disclosed FXR agonists may have potent anti-obesity and glucose lowering effects in vivo. These effects have not been observed with systemically-acting FXR ligands and may include reductions in weight gain, hyperglycemia, and/or insulin resistance. In addition, administration of these FXR agonists may produce a beneficial, anti-inflammatory effect in the intestines.

III. Compounds

Disclosed herein are embodiments of a compound that may have activity as an FXR agonist. Without limitation, these embodiments include compounds of Formula I, II, III, IV, V, VI, VII, VIII, IX, X, XI, XII, XIII, XIV, XV, XVI and XVII. Certain compounds are chiral, and all stereoisomers are included in this disclosure, as well as all geometric and structural isomers such as cis and trans isomers.

Certain disclosed embodiments have formula I

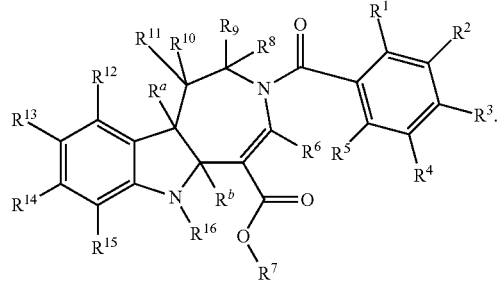

I

With reference to formula I, $R^1$-$R^{15}$ independently are selected from hydrogen, deuterium, halogen, $CF_3$, $NO_2$, OH, amino, acyl, carboxyl, carboxyl ester, cyano, aminocarbonyl, aminosulfonyl, aliphatic, D-aliphatic, heteroaliphatic, D-heteroaliphatic, or —$(CH_2)_{n1}$—$R^{150}$—$(CH_2)_{n2}$—$R^{151}$, wherein n1 and n2 are independently selected from the group consisting of 0, 1, 2, 3, and 4, $R^{150}$ is O, $NR^{16}$, or absent, and $R^{151}$ is carboxyl ester or amino; $R^{16}$ is selected from hydrogen, aliphatic, D-aliphatic, heteroaliphatic or D-heteroaliphatic; $R^a$ and $R^b$ are independently hydrogen, deuterium, aliphatic or D-aliphatic, or together form a pi-bond.

Also with reference to formula I, none of $R^1$-$R^{16}$ is —$R^x$-$L^x$-$R^{x2}$, where $R^x$ is selected from O, $NR^{x3}$, sulfonyl or S; $R^{x3}$ is selected from H, aliphatic, or aryl; $L^x$ is selected from a bond, aliphatic, heteroaliphatic, aryl, heteroaryl or $CR^{x4}R^{x5}$; $R^{x4}$ and $R^{x5}$ are each independently selected from H, D, halogen, aliphatic, —C(O)$OR^{x6}$, or —C(O)$NR^{x6}R^{x7}$; $R^{x6}$ and $R^{x7}$ are each independently selected from H, aliphatic; $R^{x2}$ is selected from —C(O)$L^{x2}R^{x8}$ or a carboxyl bioisostere; $L^{x2}$ is a bond or $NR^{x3}$; $R^{x8}$ is H, aliphatic, —$OR^{x9}$, $N(R^{x9})_2$, —C(O)$R^{x9}$, —$S(O)_2R^{x9}$, —C(O)$OR^{x9}$, —$S(O)_2N(R^{x9})_2$ or —C(O)$N(R^{x9})_2$; and each $R^{x9}$ is independently selected from H, aliphatic.

In some embodiments, at least one of $R^1$-$R^{16}$ is or comprises deuterium.

$R^7$ may be H, aliphatic, heteroaliphatic or D-heteroaliphatic. In some embodiments, $R^7$ is alkyl or deuterated alkyl, and in certain embodiments, $R^7$ is isopropyl or deuterated isopropyl, having from 1 to 7 deuterium atoms.

In some embodiments, at least one of $R^1$-$R^5$ is a halogen. In certain examples, $R^2$ and $R^3$ are both fluoro.

In some embodiments, $R^{16}$ is hydrogen.

In some examples, $R^{10}$ and $R^{11}$ independently are alkyl or deuterated alkyl, and in certain examples, $R^{10}$ and $R^{11}$ independently are methyl or deuterated methyl, having from 1 to 3 deuterium atoms.

In some embodiments, $R^a$ and $R^b$ together form a pi-bond, leading to compounds have formula II

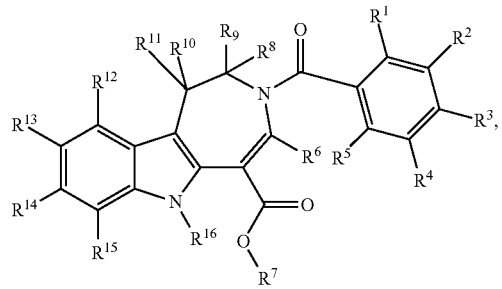

II where $R^1$-$R^{16}$ are as defined above with respect to formula I, and at least one of $R^1$-$R^{15}$ is or comprises deuterium.

In other embodiments, $R^a$ and $R^b$ are both hydrogen, leading to compounds having a formula III

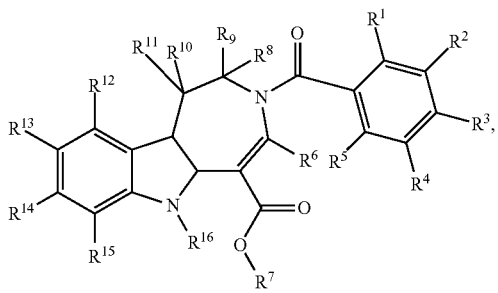

III where $R^1$-$R^{16}$ are as defined above with respect to formula I.

Exemplary compounds having formula I include:

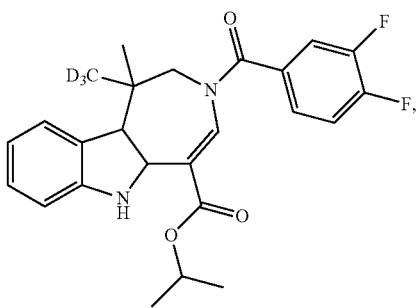

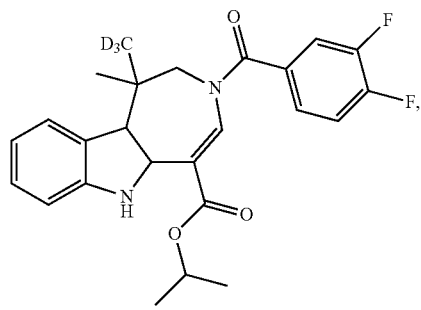
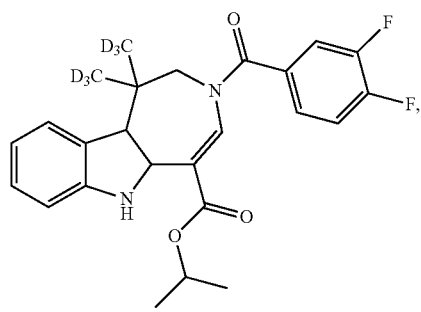
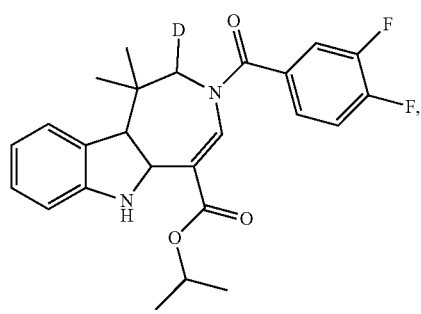
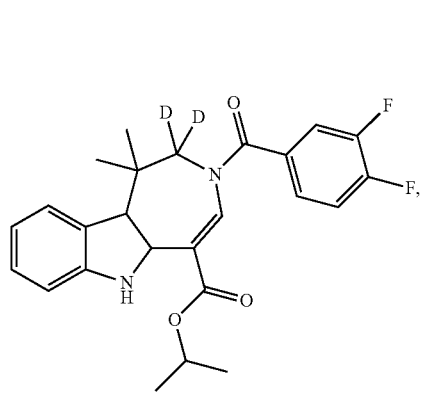
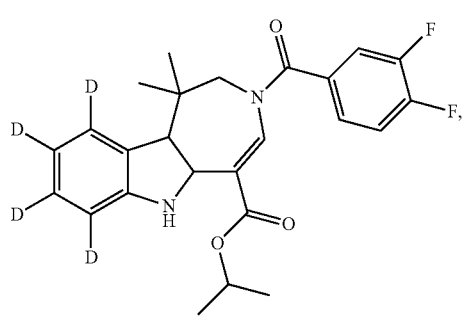
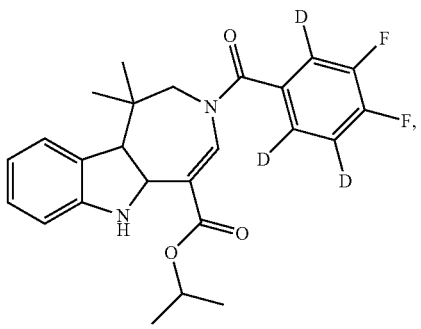
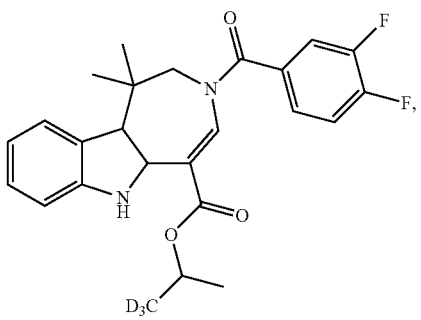
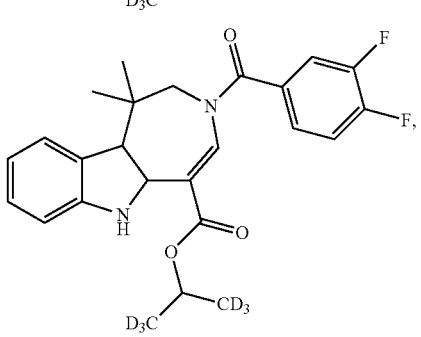
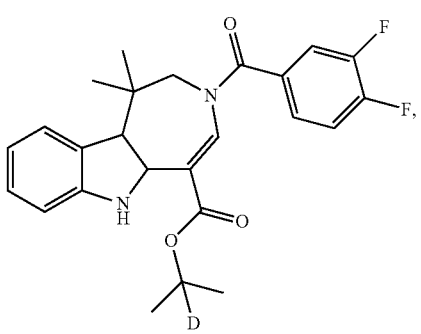
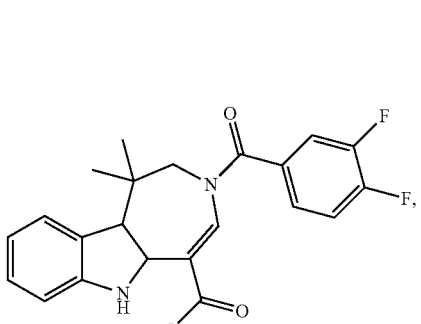

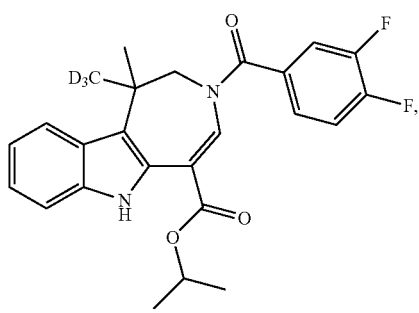
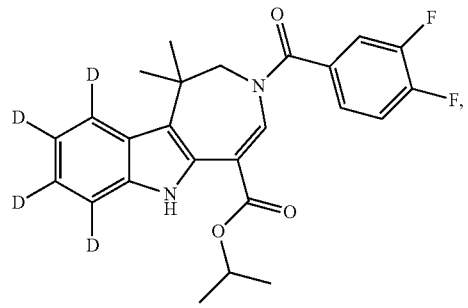

-continued

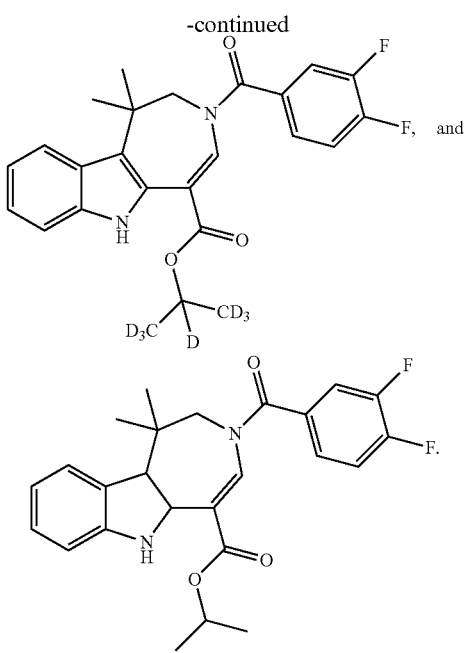

Also disclosed herein are compounds having formula IV

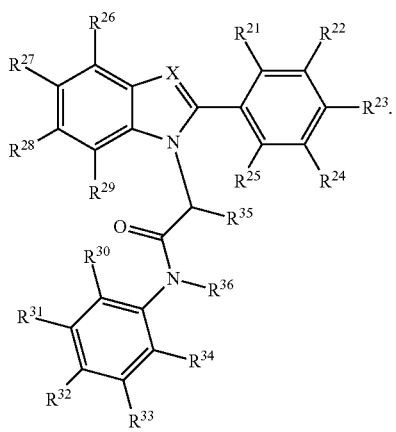

IV

With reference to formula IV, X is N or CR$^{37}$; R$^{21}$-R$_{34}$ independently are selected from hydrogen, deuterium, halogen, CF$_3$, NO$_2$, OH, amino, acyl, carboxyl, carboxyl ester, cyano, aminocarbonyl, aminosulfonyl, aliphatic, D-aliphatic, heteroaliphatic or D-heteroaliphatic; R$^{35}$ is aliphatic, D-aliphatic, heteroaliphatic or D-heteroaliphatic; R$^{36}$ is hydrogen, aliphatic, D-aliphatic, heteroaliphatic or D-heteroaliphatic; and R$^{37}$ is hydrogen, deuterium, halogen, CF$_3$, NO$_2$, OH, amino, acyl, carboxyl, carboxyl ester, cyano, aminocarbonyl, aminosulfonyl, aliphatic, D-aliphatic, heteroaliphatic or D-heteroaliphatic. In some embodiments, at least one of R$^{21}$-R$^{35}$ and R$^{37}$ is or comprises deuterium, and in certain embodiments, at least one of R$^{21}$-R$^{35}$ is or comprises deuterium.

Also with reference to formula IV, none of R$^{21}$-R$^{37}$ is —R$^x$-L$^x$-R$^{x2}$, where R$^x$ is selected from O, NR$^{x3}$, sulfonyl or S; R$^{x3}$ is selected from H, aliphatic, or aryl; L$^x$ is selected from a bond, aliphatic, heteroaliphatic, aryl, heteroaryl or CR$^{x4}$R$^{x5}$; R$^{x4}$ and R$^{x5}$ are each independently selected from H, D, halogen, aliphatic, —C(O)OR$^{x6}$, or —C(O)NR$^{x6}$R$^{x7}$; R$^{x6}$ and R$^{x7}$ are each independently selected from H, aliphatic; R$^{x2}$ is selected from —C(O)L$^{x2}$R$^{x8}$ or a carboxyl bioisostere; L$^{x2}$ is a bond or NR$^{x3}$; R$^{x8}$ is H, aliphatic, —OR$^{x9}$, N(R$^{x9}$)$_2$, —C(O)R$^{x9}$, —S(O)$_2$R$^{x9}$, —C(O)OR$^{x9}$, —S(O)$_2$N(R$^{x9}$)$_2$ or —C(O)N(R$^{x9}$)$_2$; and each R$^{x9}$ is independently selected from H, aliphatic.

In some embodiments, R$^{35}$ is alkyl, cycloalkyl, deuterated alkyl or deuterated cycloalkyl. In certain disclosed embodiments, R$^{35}$ is cycloalkyl or deuterated cycloalkyl, typically cyclohexyl or deuterated cyclohexyl, having from 1 to 11 deuterium atoms.

In some examples, R$^{36}$ is hydrogen.

In some embodiments, R$^{32}$ is carboxyl and/or R$^{34}$ is CF$_3$.

In some embodiments, R$^{23}$ is halogen, and in certain embodiments R$^{23}$ is chloro.

In some embodiments, the compound is chiral, and in certain embodiments, the compound is the S-stereoisomer.

In some embodiments, X is N, leading to compounds having a formula V

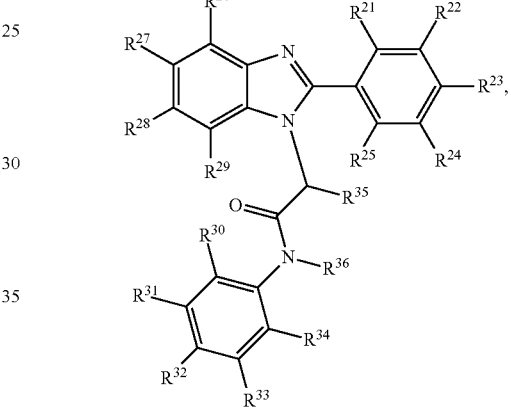

V where R$^{21}$-R$^{36}$ is as defined above with respect to formula IV, and at least one of R$^{21}$-R$^{36}$ is or comprises deuterium.

In other embodiments, X is CH, leading to compounds having formula VI

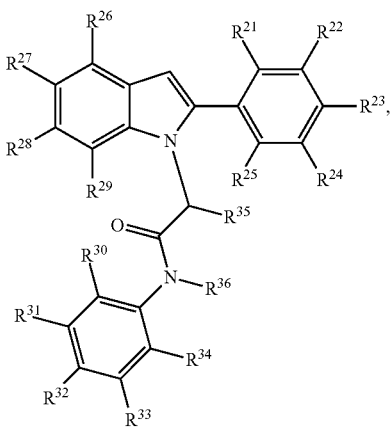

VI where R$^{21}$-R$^{36}$ is as defined above with respect to formula IV.

Exemplary compounds having formula IV include:
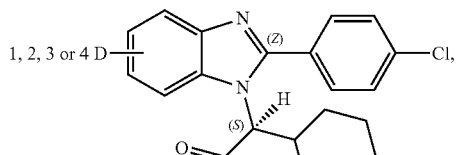
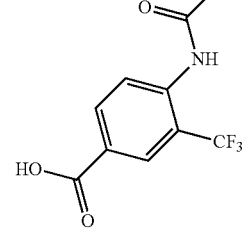
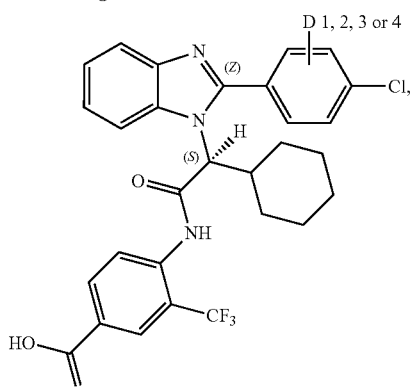
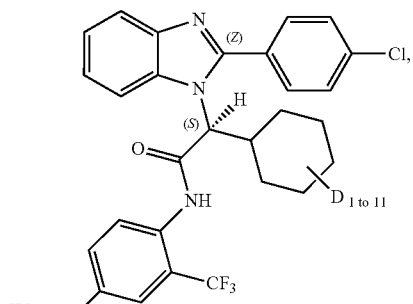
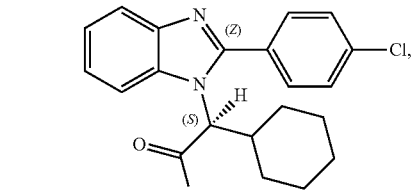
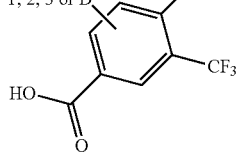
-continued
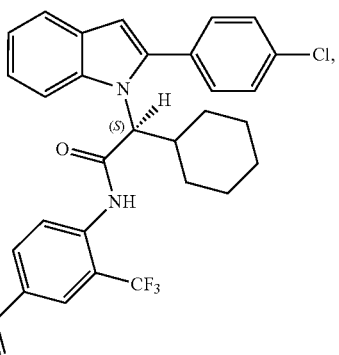
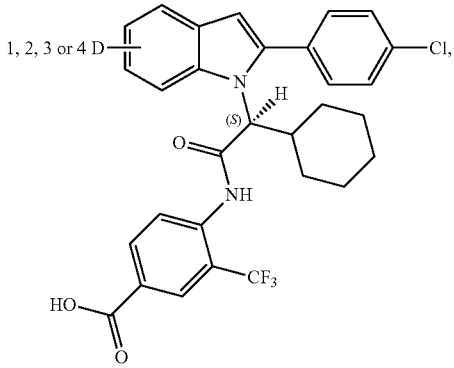
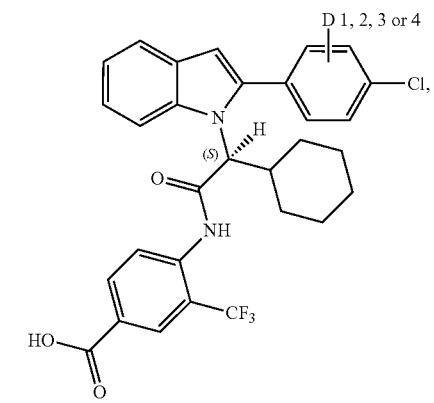
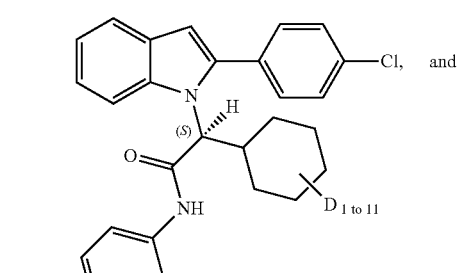

-continued

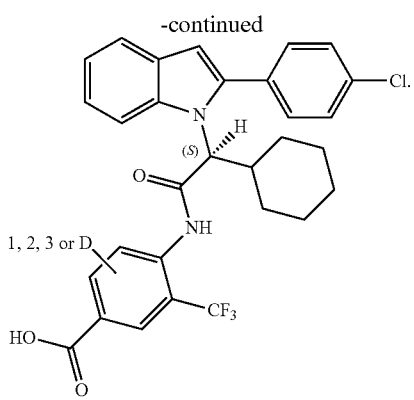

Also disclosed herein are compounds having formula VII

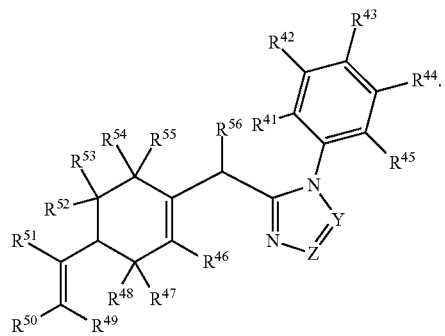

VII

With reference to formula VII, $R^{41}$-$R^{48}$ and $R^{52}$-$R^{55}$ independently are selected from hydrogen, deuterium, halogen, $CF_3$, $NO_2$, OH, amino, acyl, carboxyl, carboxyl ester, cyano, aminocarbonyl, aminosulfonyl, aliphatic, D-aliphatic, heteroaliphatic or D-heteroaliphatic; $R^{49}$-$R^{51}$ independently are selected from hydrogen, deuterium, aliphatic, D-aliphatic, heteroaliphatic or D-heteroaliphatic; $R^{56}$ is amino, cycloamino or substituted cycloamino, such as 5-, 6-, or 7-membered cycloamino; Y and Z are independently N or $CR^{57}$; and each $R^{57}$ independently is selected from deuterium, halogen, $CF_3$, $NO_2$, OH, amino, acyl, carboxyl, carboxyl ester, cyano, aminocarbonyl, aminosulfonyl, aliphatic, D-aliphatic, heteroaliphatic or D-heteroaliphatic.

Also with reference to formula VII, none of $R^{41}$-$R^{57}$ is —$R^x$-$L^x$-$R^{x2}$, where $R^x$ is selected from O, $NR^{x3}$, sulfonyl or S; $R^{x3}$ is selected from H, aliphatic, or aryl; $L^x$ is selected from a bond, aliphatic, heteroaliphatic, aryl, heteroaryl or $CR^{x4}R^{x5}$; $R^{x4}$ and $R^{x5}$ are each independently selected from H, D, halogen, aliphatic, —C(O)O$R^{x6}$, or —C(O)N$R^{x6}R^{x7}$; $R^{x6}$ and $R^{x7}$ are each independently selected from H, aliphatic; $R^{x2}$ is selected from —C(O)$L^{x2}R^{x8}$ or a carboxyl bioisostere; $L^{x2}$ is a bond or $NR^{x3}$; $R^{x8}$ is H, aliphatic, —O$R^{x9}$, N($R^{x9}$)$_2$, —C(O)$R^{x9}$, —S(O)$_2R^{x9}$, —C(O)O$R^{x9}$, —S(O)$_2$N($R^{x9}$)$_2$ or —C(O)N($R^{x9}$)$_2$; and each $R^{x9}$ is independently selected from H, aliphatic.

In some embodiments, at least one of $R^{41}$-$R^{56}$ is or comprises deuterium.

In some embodiments, $R^{51}$ is an aliphatic or D-aliphatic, and in certain embodiments, $R^{51}$ is a methyl or deuterated methyl, having from 1 to 3 deuterium atoms.

In some embodiments, $R^{49}$ and $R^{50}$ independently are hydrogen or deuterium.

In some embodiments, $R^{41}$ and $R^{45}$ independently are aliphatic or D-aliphatic, and in particular embodiments, $R^{41}$ and $R^{45}$ are methyl or deuterated methyl, having from 1 to 3 deuterium atoms.

In some embodiments, $R^{56}$ is a cycloamino or substituted cycloamino, such as pyrrolidine, 2-methylpyrrolidine, morpholine, 4-methylpiperazine, piperidine, or azepane (homopiperidine).

In some embodiments, Y is N and Z is N leading to compounds having a formula VIII

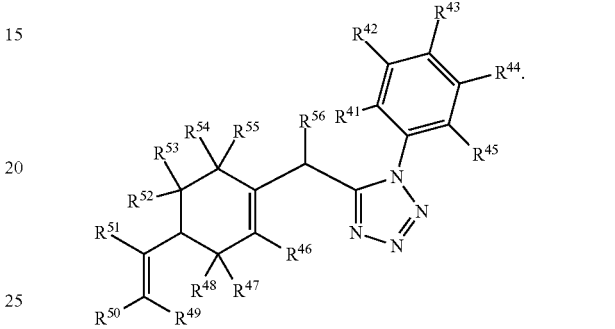

VIII

In other embodiments, Y is CH and Z is CH leading to compounds having a formula IX

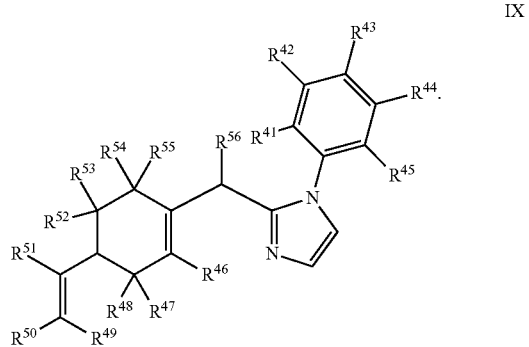

IX

In other examples, Y is N and Z is CH leading to compounds having a formula X

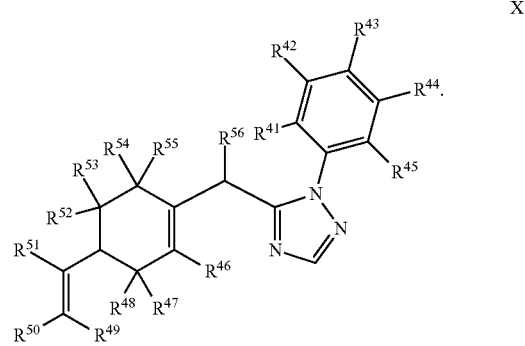

X

And in other examples Y is CH and Z is N leading to compounds having a formula XI

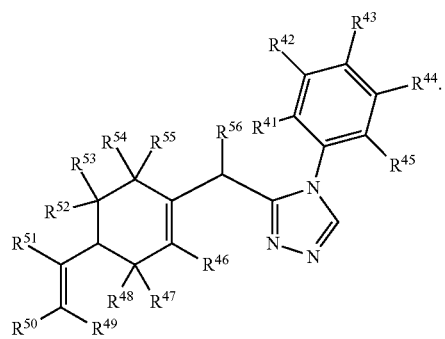
With respect to formulas VIII-XI, $R^{41}$-$R^{56}$ are as defined for formula VII.
Exemplary compounds having formula VII include:
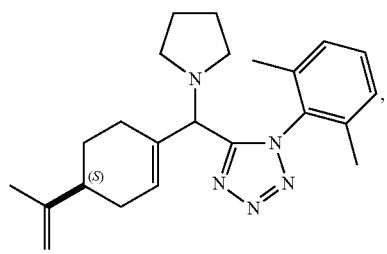
31% activity
CLogP: 4.757
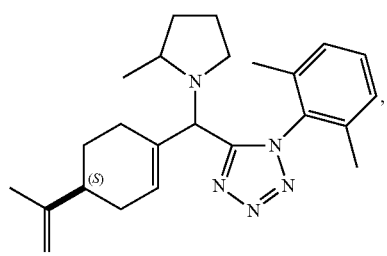
11.5% activity
CLogP: 5.276
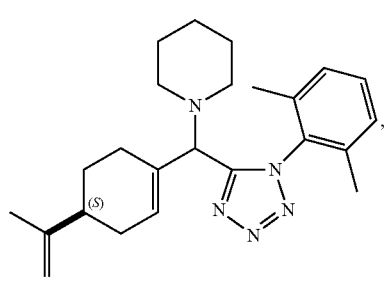
7.2% activity
CLogP: 5.316
-continued
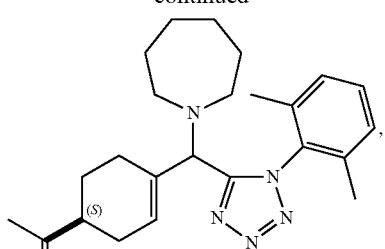
34% activity
CLogP: 5.875
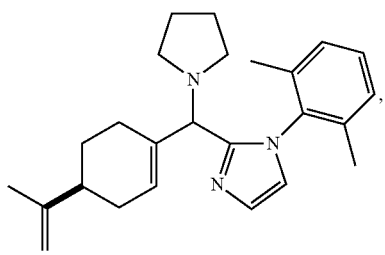
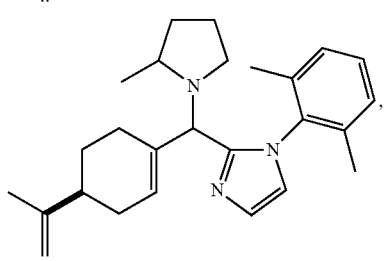
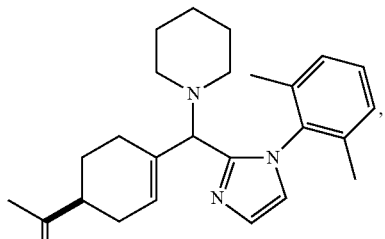
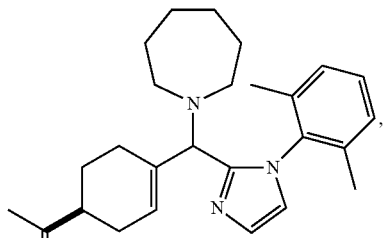
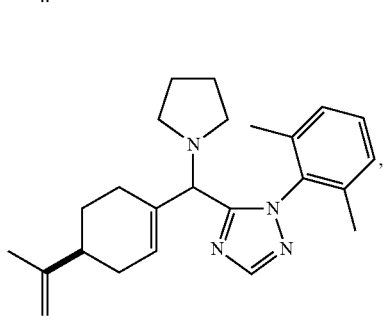

49
-continued
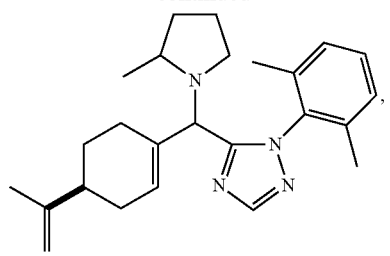
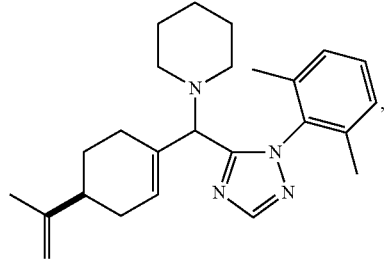
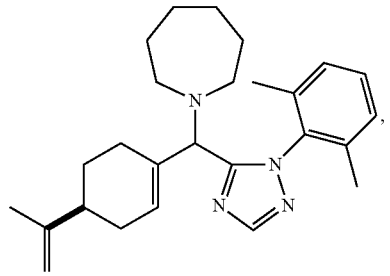
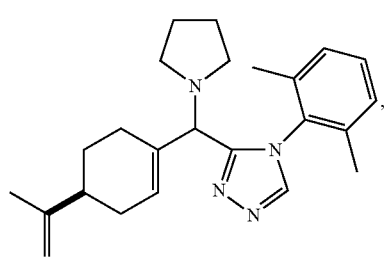
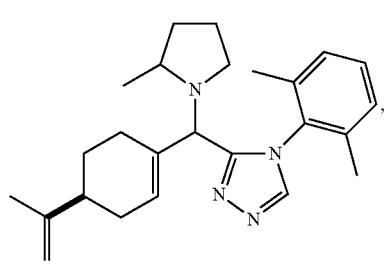
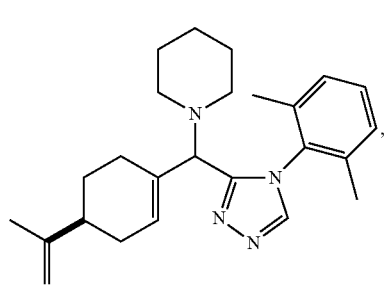
50
-continued
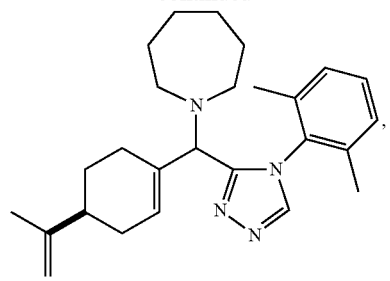
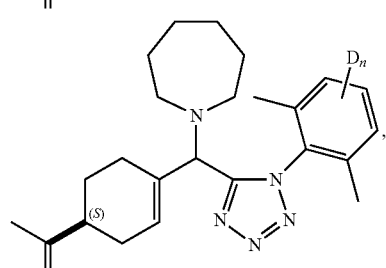
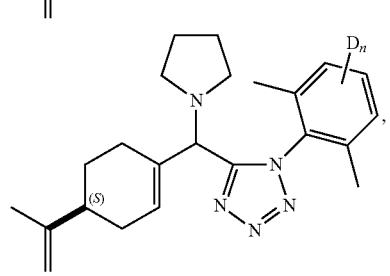
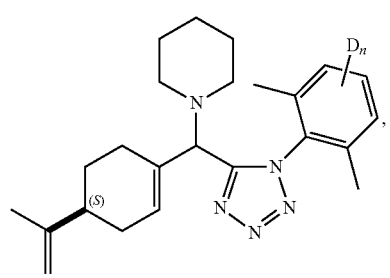
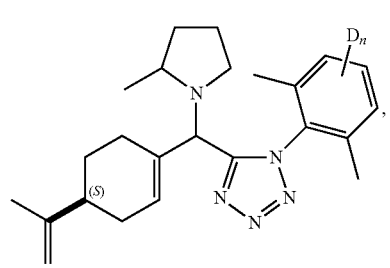
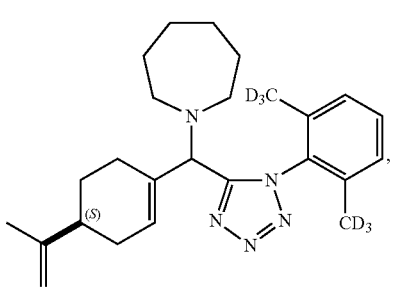

-continued

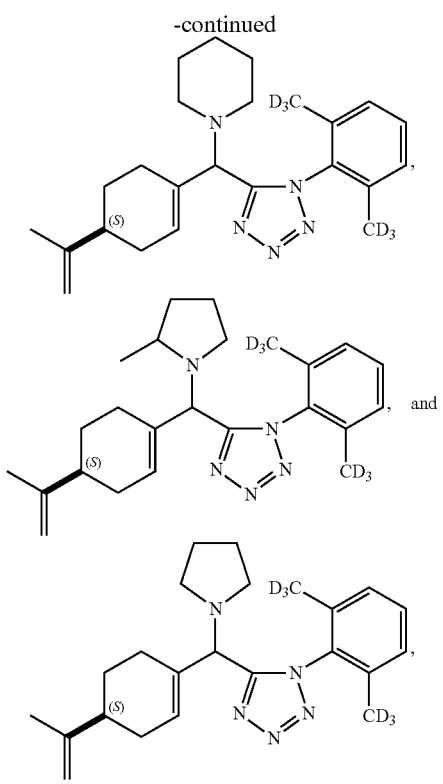

wherein n is from 1 to 3.

Also disclosed herein are compounds having formula XII,

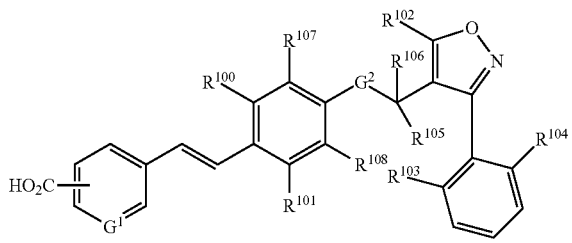

wherein $G^1$ is CH or N; $G^2$ is O or NH; $R^{100}$ and $R^{101}$ are independently H, D, halogen, aliphatic, D-aliphatic, heteroaliphatic or D-heteroaliphatic; $R^{102}$ is aliphatic, heteropaliphatic, D-aliphatic or D-heteroaliphatic; $R^{103}$ and $R^{104}$ are independently H, D, halogen, OH, alkoxy, O-polyhaloalkyl, aliphatic, D-aliphatic, heteroaliphatic or D-heteroaliphatic; $R^{105}$ and $R^{106}$ are each independently H, D, halogen, aliphatic or D-aliphatic; $R^{107}$ and $R^{108}$ are each independently H, D, aliphatic, D-aliphatic or halogen. In some embodiments, $R^{100}$ and $R^{101}$ are independently H, D, lower alkyl, halogen, or $CF_3$; $R^{102}$ is lower alkyl; $R^{103}$ and $R^{104}$ are independently H, D, lower alkyl, halogen, $CF_3$, OH, O-alkyl, or O-polyhaloalkyl; $R^{105}$ and $R^{106}$ are each independently H, D, halogen, alkyl or deuterated alkyl; $R^{107}$ and $R^{108}$ are each independently H, D, alkyl, deuterated alkyl or halogen. In some embodiments, at least one of $R^{100}$, $R^{101}$, $R^{102}$, $R^{103}$, $R^{104}$, $R^{105}$, $R^{106}$, $R^{107}$ and $R^{108}$ is or comprises deuterium. In some embodiments, at least one of $R^{105}$, $R^{106}$, $R^{107}$ and $R^{108}$ is or comprises deuterium. In other embodiments, at least one of $R^{107}$ and $R^{108}$ is halogen, and may be fluoro.

In certain embodiments, the compound has a formula XIII

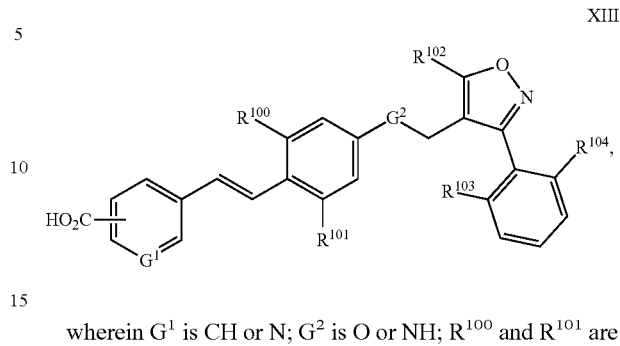

wherein $G^1$ is CH or N; $G^2$ is O or NH; $R^{100}$ and $R^{101}$ are independently H, lower alkyl, halogen, or $CF_3$; $R^{102}$ is lower alkyl; $R^{103}$ and $R^{104}$ are independently H, lower alkyl, halogen, $CF_3$, OH, O-alkyl, or O-polyhaloalkyl.

Exemplary compounds having formula XII or formula XIII include

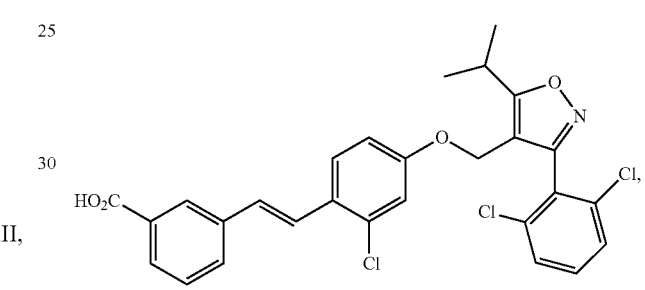

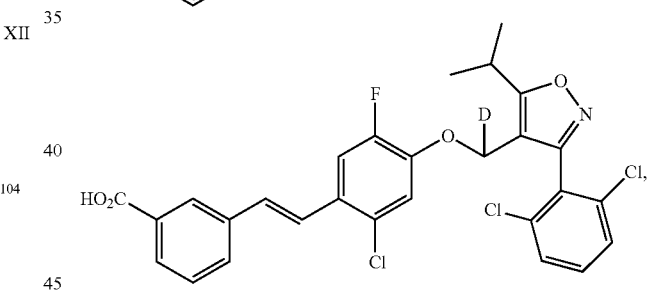

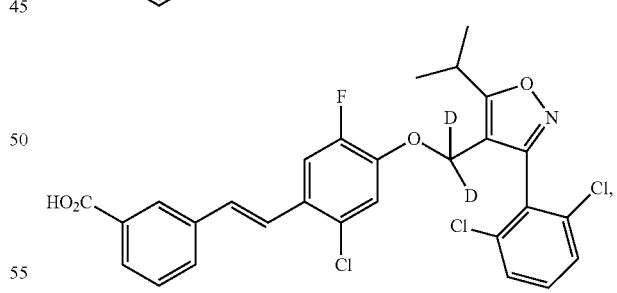

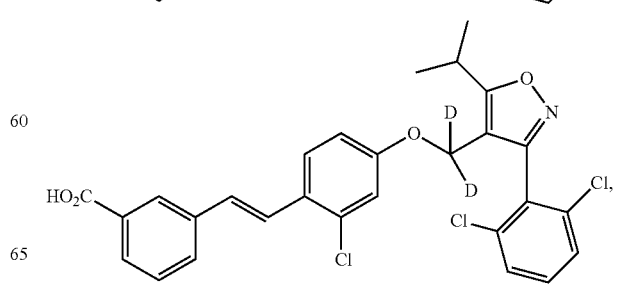

-continued

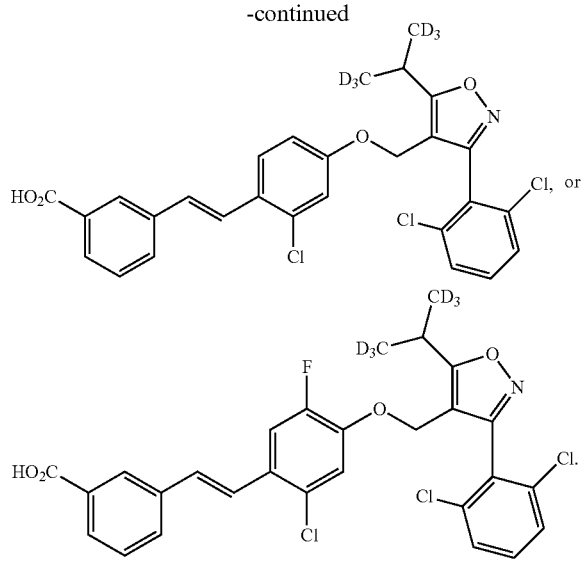

Other exemplary compounds having formula XII or formula XIII include
(E)-3-(2-chloro-4-((3-(2,6-dichlorophenyl)-5-isopropylisoxazol-4-yl)methoxy)styryl)benzoic acid;
(E)-3-(2-chloro-4-((3-(2,6-dichlorophenyl)-5-isopropylisoxazol-4-yl)methoxy-d)-5-fluorostyryl-d)benzoic acid;
(E)-3-(2-chloro-4-((3-(2,6-dichlorophenyl)-5-isopropylisoxazol-4-yl)methoxy-d2)-5-fluorostyryl-d2)benzoic acid;
(E)-3-(2-chloro-4-((3-(2,6-dichlorophenyl)-5-isopropylisoxazol-4-yl)methoxy-d2)styryl-d2)benzoic acid;
(E)-3-(2-chloro-4-((3-(2,6-dichlorophenyl)-5-(propan-2-yl-1,1,1,3,3,3-d6)isoxazol-4-yl)methoxy)styryl-d6)benzoic acid; or
(E)-3-(2-chloro-4-((3-(2,6-dichlorophenyl)-5-(propan-2-yl-1,1,1,3,3,3-d6)isoxazol-4-yl)methoxy)-5-fluorostyryl-d6)benzoic acid.

Also disclosed herein are compounds having formula XIV,

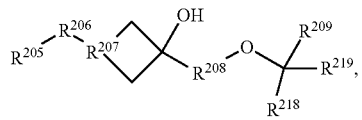

XIV wherein
$R^{205}$ is selected from the group consisting of COOR$^{210}$, CONR$^{211}$R$^{212}$, tetrazolyl, SO$_2$NR$^{211}$R$^{212}$, C$_{1-6}$ alkyl, SO$_2$—C$_{1-6}$ alkyl and H, with R$^{210}$ independently selected from the group consisting of H or C$_{1-6}$ alkyl, and R$^{211}$ and R$^{212}$ independently from each other selected from the group consisting of H, C$_{1-6}$ alkyl, halo-C$_{1-6}$ alkyl, C$_{1-6}$ alkylene-R$^{213}$, SO$_2$—C$_{1-6}$ alkyl, wherein R$^{213}$ is selected from the group consisting of COOH, OH and SO$_3$H;
$R^{206}$ is selected from the group consisting of phenyl, pyridyl, pyrimidyl, pyrazolyl, indolyl, thienyl, benzothienyl, indazolyl, benzisoxazolyl, benzofuranyl, benzotriazolyl, furanyl, benzothiazolyl, thiazolyl, oxadiazolyl, each optionally substituted with one or two groups independently selected from the group consisting of OH, O—C$_{1-6}$ alkyl, O-halo-C$_{1-6}$ alkyl, C$_{1-6}$ alkyl, halo-C$_{1-6}$ alkyl, C$_{3-6}$ cycloalkyl, D and halogen;

$R^{207}$ is selected from N or CH;
$R^{208}$ is selected from the group consisting of phenyl, pyridyl, thiazolyl, thiophenyl, pyrimidyl, each optionally substituted with one or two groups independently selected from the group consisting of D, C$_{1-6}$ alkyl, halo-C$_{1-6}$ alkyl, halogen and CF$_3$;
$R^{209}$ is selected from

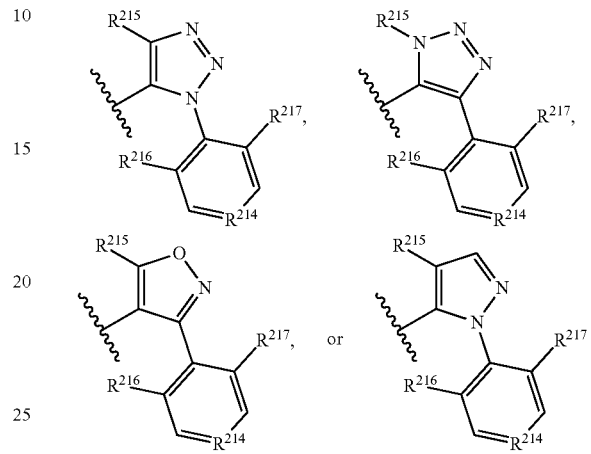

wherein
$R^{214}$=CH, N, NO, CD;
$R^{215}$ is selected from the group consisting of hydrogen, C$_{1-3}$ alkyl, C$_{3-6}$ cylcoalkyl, C$_{4-5}$ alkylcycloalkyl, wherein C$_{1-3}$ alkyl is optionally substituted with 1 to 3 substituents independently selected from halogen, hydroxy or C$_{1-6}$ alkoxy;
$R^{216}$ and $R^{217}$ are independently selected from the group consisting of hydrogen, D, C$_{1-3}$ alkyl, C$_{1-3}$ haloalkyl, C$_{1-3}$ alkoxy, C$_{1-3}$ haloalkoxy, D-aliphatic and halogen.
$R^{218}$ and $R^{219}$ are each independently H or D. In some embodiments, $R^{218}$ and $R^{219}$ are both H. In other embodiments, at least one of $R^{218}$ and $R^{219}$ is D.

In some embodiments, the compound comprises at least one deuterium. In some embodiments, $R^{206}$ and/or $R^{208}$ comprise at least one deuterium. In other embodiments, $R^{214}$ is CD. In certain embodiments, at least one of $R^{216}$ and $R^{217}$ is or comprises deuterium.

In some embodiments for compounds having formula XIV, $R^{205}$-$R^{206}$ is selected from

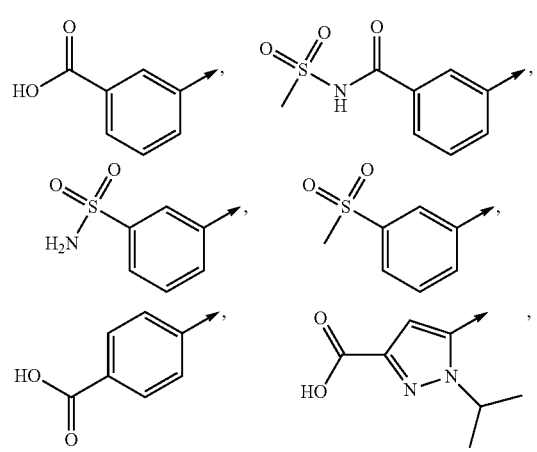

-continued
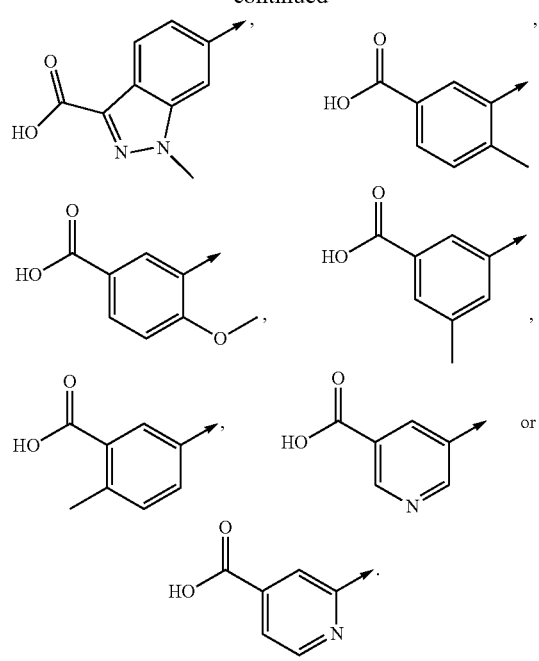
In some embodiments for compounds having formula XIV, $R^{208}$ is
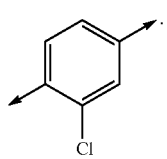
In some embodiments for compounds having formula XIV, $R^{209}$ is
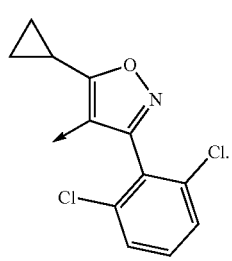
Exemplary compounds having formula XIV include:
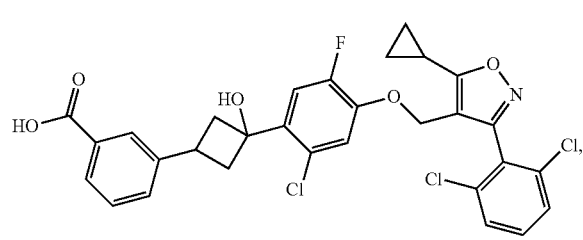
-continued
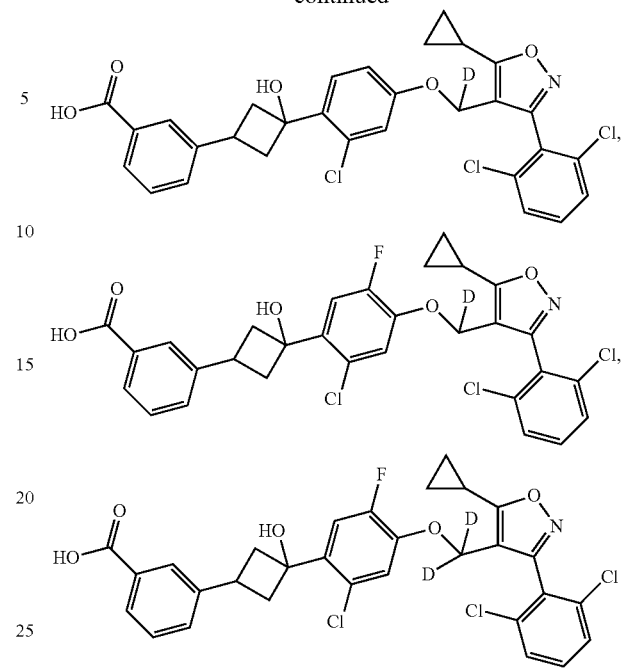
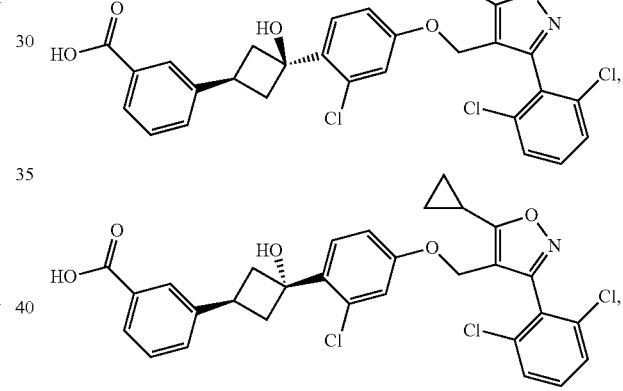
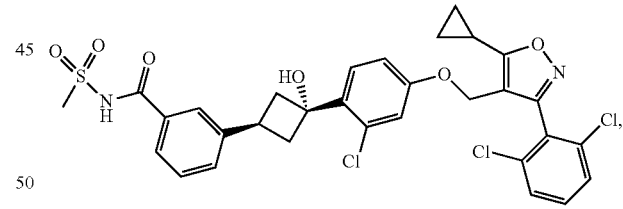
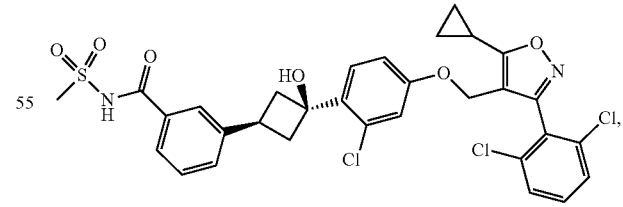
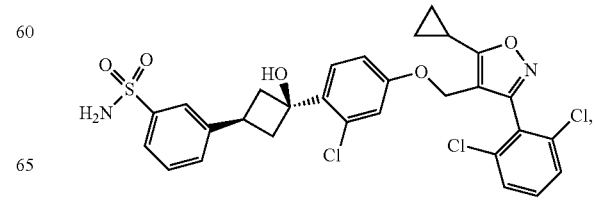

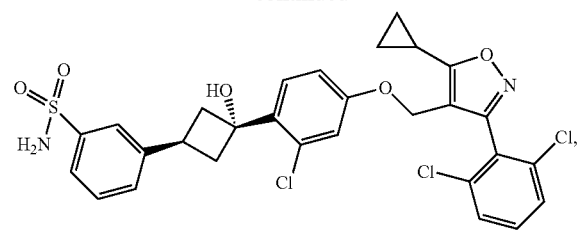
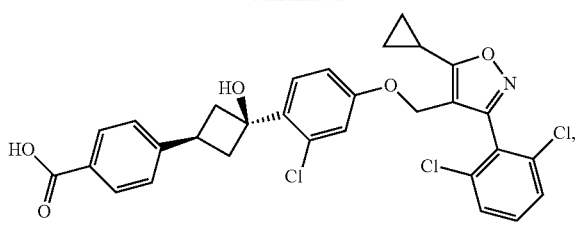
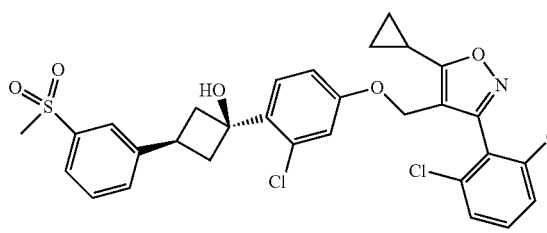
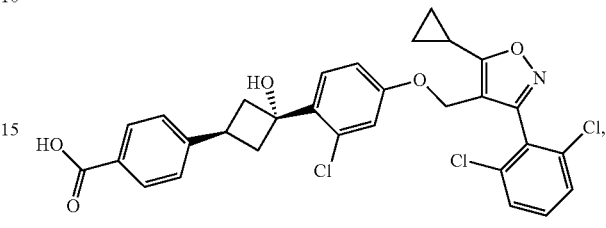
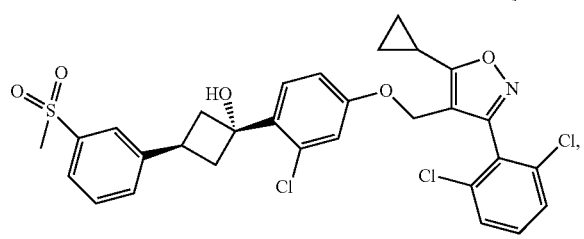
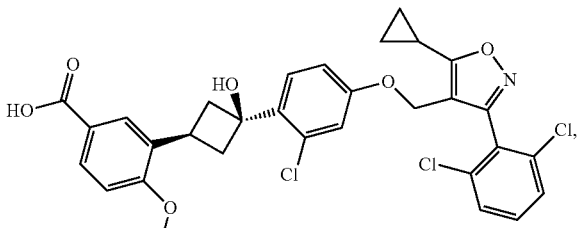
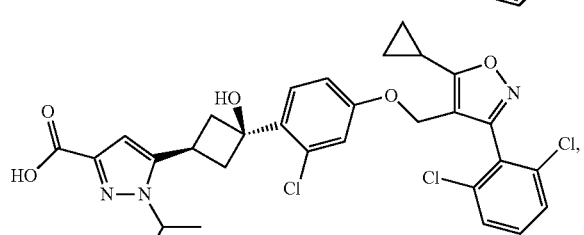
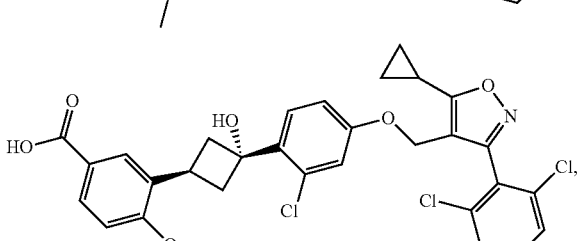
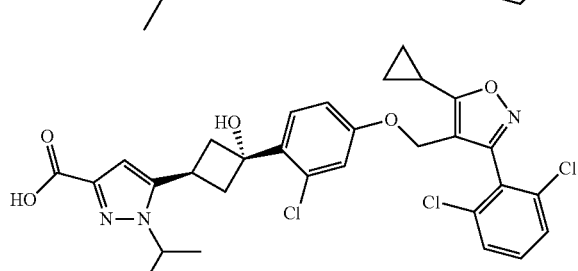
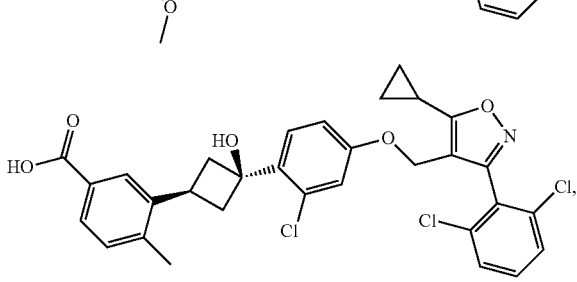
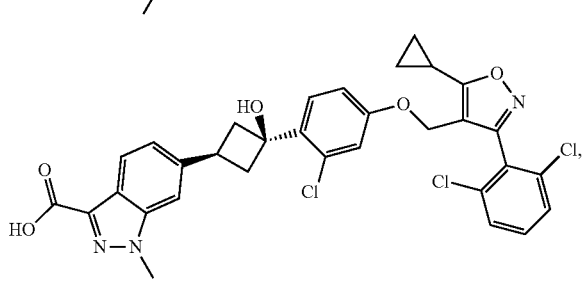
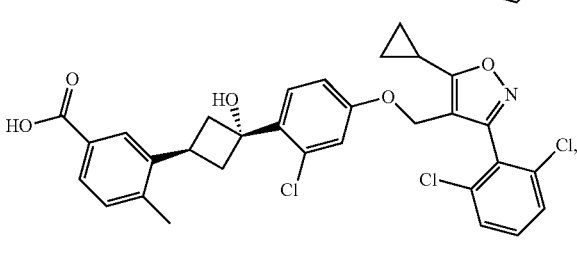
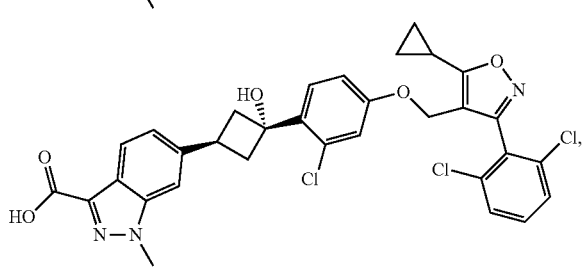
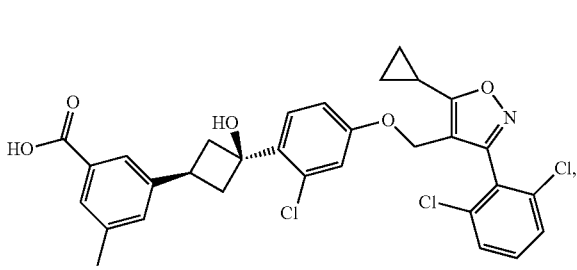

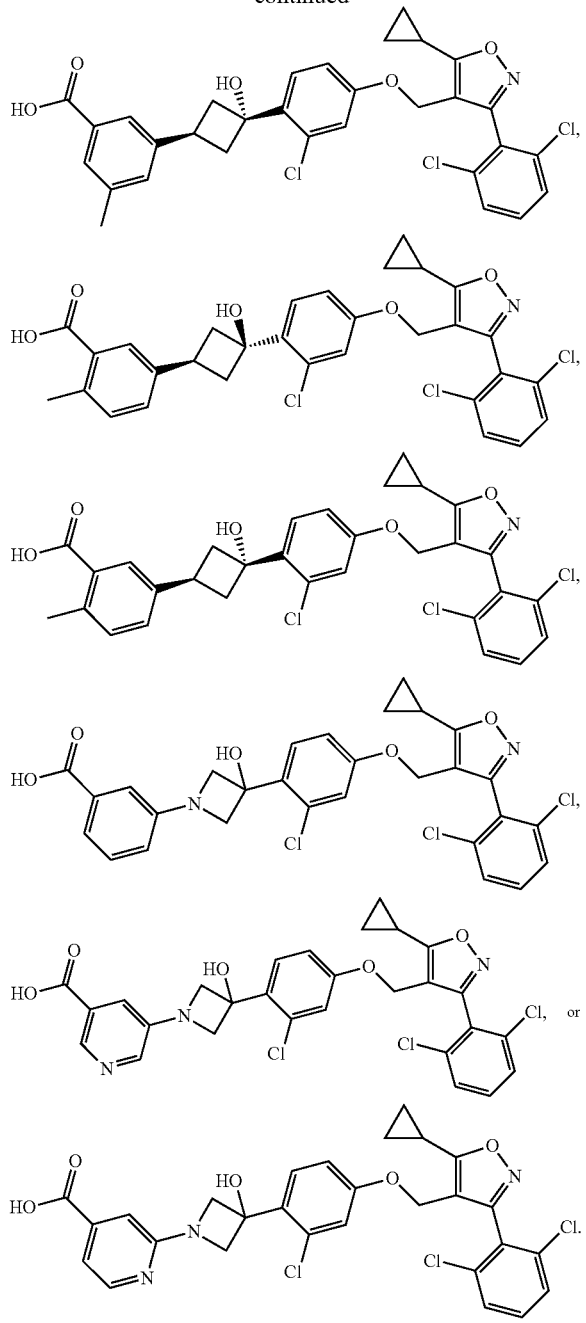

Other Exemplary compounds having formula XIV include
- 3-(3-(2-chloro-4-((5-cyclopropyl-3-(2,6-dichlorophenyl)isoxazol-4-yl)methoxy)-5-fluorophenyl)-3-hydroxycyclobutyl)benzoic acid;
- 3-(3-(2-chloro-4-((5-cyclopropyl-3-(2,6-dichlorophenyl)isoxazol-4-yl)methoxy-d)phenyl)-3-hydroxycyclobutyl)benzoic acid;
- 3-(3-(2-chloro-4-((5-cyclopropyl-3-(2,6-dichlorophenyl)isoxazol-4-yl)methoxy-d)-5-fluorophenyl)-3-hydroxycyclobutyl)benzoic acid;
- 3-(3-(2-chloro-4-((5-cyclopropyl-3-(2,6-dichlorophenyl)isoxazol-4-yl)methoxy-d2)-5-fluorophenyl)-3-hydroxycyclobutyl)benzoic acid;
- 3-((1s,3s)-3-(2-chloro-4-((5-cyclopropyl-3-(2,6-dichlorophenyl)isoxazol-4-yl)methoxy)phenyl)-3-hydroxycyclobutyl)benzoic acid;
- 3-((1r,3r)-3-(2-chloro-4-((5-cyclopropyl-3-(2,6-dichlorophenyl)isoxazol-4-yl)methoxy)phenyl)-3-hydroxycyclobutyl)benzoic acid;
- 3-((1r,3r)-3-(2-chloro-4-((5-cyclopropyl-3-(2,6-dichlorophenyl)isoxazol-4-yl)methoxylphenyl)-3-hydroxycyclobutyl)-N-(methylsulfonyl)benzamide;
- 3-((1s,3s)-3-(2-chloro-4-((5-cyclopropyl-3-(2,6-dichlorophenyl)isoxazol-4-yl)methoxy)phenyl)-3-hydroxycyclobutyl)-N-(methylsulfonyl)benzamide;
- 3-((1s,3s)-3-(2-chloro-4-((5-cyclopropyl-3-(2,6-dichlorophenyl)isoxazol-4-yl)methoxy)phenyl)-3-hydroxycyclobutyl)benzenesulfonamide;
- 3-((1r,3r)-3-(2-chloro-4-((5-cyclopropyl-3-(2,6-dichlorophenyl)isoxazol-4-yl)methoxy)phenyl)-3-hydroxycyclobutyl)benzenesulfonamide;
- (1s,3s)-1-(2-chloro-4-((5-cyclopropyl-3-(2,6-dichlorophenyl)isoxazol-4-yl)methoxy)phenyl)-3-(3-(methylsulfonyl)phenyl)cyclobutan-1-ol;
- (1r,3r)-1-(2-chloro-4-((5-cyclopropyl-3-(2,6-dichlorophenyl)isoxazol-4-yl)methoxy)phenyl)-3-(3-(methylsulfonyl)phenyl)cyclobutan-1-ol;
- 5-((1s,3s)-3-(2-chloro-4-((5-cyclopropyl-3-(2,6-dichlorophenyl)isoxazol-4-yl)methoxy)phenyl)-3-hydroxycyclobutyl)-1-isopropyl-1H-pyrazole-3-carboxylic acid;
- 5-((1r,3r)-3-(2-chloro-4-((5-cyclopropyl-3-(2,6-dichlorophenyl)isoxazol-4-yl)methoxy)phenyl)-3-hydroxycyclobutyl)-1-isopropyl-1H-pyrazole-3-carboxylic acid;
- 6-((1s,3s)-3-(2-chloro-4-((5-cyclopropyl-3-(2,6-dichlorophenyl)isoxazol-4-yl)methoxy)phenyl)-3-hydroxycyclobutyl)-1-methyl-1H-indazole-3-carboxylic acid;
- 6-((1r,3r)-3-(2-chloro-4-((5-cyclopropyl-3-(2,6-dichlorophenyl)isoxazol-4-yl)methoxy)phenyl)-3-hydroxycyclobutyl)-1-methyl-1H-indazole-3-carboxylic acid;
- 4-((1s,3s)-3-(2-chloro-4-((5-cyclopropyl-3-(2,6-dichlorophenyl)isoxazol-4-yl)methoxy)phenyl)-3-hydroxycyclobutyl)benzoic acid;
- 4-((1r,3r)-3-(2-chloro-4-((5-cyclopropyl-3-(2,6-dichlorophenyl)isoxazol-4-yl)methoxy)phenyl)-3-hydroxycyclobutyl)benzoic acid;
- 3-((1s,3s)-3-(2-chloro-4-((5-cyclopropyl-3-(2,6-dichlorophenyl)isoxazol-4-yl)methoxy)phenyl)-3-hydroxycyclobutyl)-4-methoxybenzoic acid;
- 3-((1r,3r)-3-(2-chloro-4-((5-cyclopropyl-3-(2,6-dichlorophenyl)isoxazol-4-yl)methoxy)phenyl)-3-hydroxycyclobutyl)-4-methoxybenzoic acid;
- 3-((1s,3s)-3-(2-chloro-4-((5-cyclopropyl-3-(2,6-dichlorophenyl)isoxazol-4-yl)methoxy)phenyl)-3-hydroxycyclobutyl)-4-methylbenzoic acid;
- 3-((1r,3r)-3-(2-chloro-4-((5-cyclopropyl-3-(2,6-dichlorophenyl)isoxazol-4-yl)methoxy)phenyl)-3-hydroxycyclobutyl)-4-methylbenzoic acid;
- 3-((1s,3s)-3-(2-chloro-4-((5-cyclopropyl-3-(2,6-dichlorophenyl)isoxazol-4-yl)methoxy)phenyl)-3-hydroxycyclobutyl)-5-methylbenzoic acid;
- 3-((1r,3r)-3-(2-chloro-4-((5-cyclopropyl-3-(2,6-dichlorophenyl)isoxazol-4-yl)methoxy)phenyl)-3-hydroxycyclobutyl)-5-methylbenzoic acid;
- 3-((1s,3s)-3-(2-chloro-4-((5-cyclopropyl-3-(2,6-dichlorophenyl)isoxazol-4-yl)methoxy)phenyl)-3-hydroxycyclobutyl)-2-methylbenzoic acid;
- 5-((1r,3r)-3-(2-chloro-4-((5-cyclopropyl-3-(2,6-dichlorophenyl)isoxazol-4-yl)methoxy)phenyl)-3-hydroxycyclobutyl)-2-methylbenzoic acid;

3-(3-(2-chloro-4-((5-cyclopropyl-3-(2,6-dichlorophenyl)isoxazol-4-yl)methoxy)phenyl)-3-hydroxyazetidin-1-yl)benzoic acid;

5-(3-(2-chloro-4-((5-cyclopropyl-3-(2,6-dichlorophenyl)isoxazol-4-yl)methoxy)phenyl)-3-hydroxyazetidin-1-yl)nicotinic acid; or 2-(3-(2-chloro-4-((5-cyclopropyl-3-(2,6-dichlorophenyl)isoxazol-4-yl)methoxy)phenyl)-3-hydroxyazetidin-1-yl)isonicotinic acid.

Also disclosed herein are compounds having formula XV,

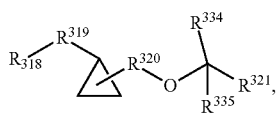

XV wherein $R^{318}$ is selected from the group consisting of $COOR^{322}$, $CONR^{323}R^{324}$, tetrazolyl or H, with $R^{322}$ independently selected from the group consisting of H, or lower alkyl, and $R^{323}$ and $R^{324}$ independently from each other selected from the group consisting of H, lower alkyl, $C_{1-6}$ haloalkyl, $C_{1-6}$ alkylene-$R^{325}$, $SO_2$—$C_{1-6}$ alkyl wherein $R^{325}$ is selected from the group consisting of COOH, OH, or $SO_3H$;

$R^{319}$ is selected from the group consisting of phenyl, pyridyl, pyrazolyl, indolyl, thienyl, benzothienyl, indazolyl, benzisoxazolyl, benzofuranyl, benzothiazolyl, furanyl, benzothiazolyl, thiazolyl, each optionally substituted with one or two groups independently selected from the group consisting of OH, lower alkyl, lower cycloalkyl, or halogen;

$R^{320}$ is selected from the group consisting of phenyl, pyridyl, thiazolyl, thiophenyl, pyrimidyl, each optionally substituted with one or two groups independently selected from the group consisting of lower alkyl, halogen, D or $CF_3$;

$R^{321}$ is

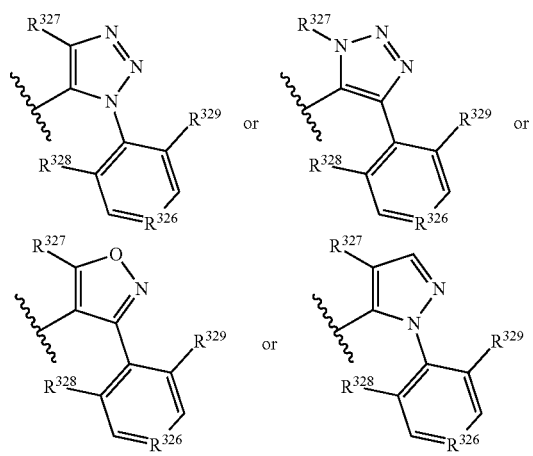

wherein $R^{326}$ is CH, N, NO;

$R_{327}$ is selected from the group consisting of hydrogen, $C_1$-$C_3$ alkyl, $C_3$-$C_6$ cylcoalkyl, $C_4$-$C_5$ alkylcycloalkyl, wherein $C_{1-3}$ alkyl is optionally substituted with 1 to 3 substituents independently selected from halogen, hydroxy or $C_{1-6}$ alkoxy, $R^{328}$ and $R^{329}$ are independently selected from the group consisting of hydrogen, $C_1$-$C_3$ alkyl, $C_1$-$C_3$ haloalkyl, $C_1$-$C_3$ alkoxy, $C_1$-$C_3$ haloalkoxy and halogen.

$R^{334}$ and $R^{335}$ are each independently H or D. In some embodiments, at least one of $R^{334}$ and $R^{335}$ are D.

In some embodiments, $R^{320}$ is substituted with at least one halogen or deuterium.

In some embodiments for compounds having formula XV, $R^{318}$ is selected from the group consisting of $COOR^{322}$, $CONR^{323}R^{324}$, tetrazolyl or H, with $R^{322}$, $R^{323}$ and $R^{324}$ independently selected from the group consisting of H, lower alkyl;

$R^{319}$ is selected from the group consisting of phenyl, pyridyl, indolyl, thienyl, benzothienyl, indazolyl, benzisoxazolyl, benzofuranyl, benzothiazolyl, furanyl, benzothiazolyl, thiazolyl, each optionally substituted with one or two groups independently selected from the group consisting of OH, lower alkyl, lower cycloalkyl;

$R^{320}$ is selected from the group consisting of phenyl, pyridyl, thiazolyl, thiophenyl, pyrimidyl, each optionally substituted with one or two groups independently selected from the group consisting of lower alkyl, halogen, D or $CF_3$;

$R^{321}$ is

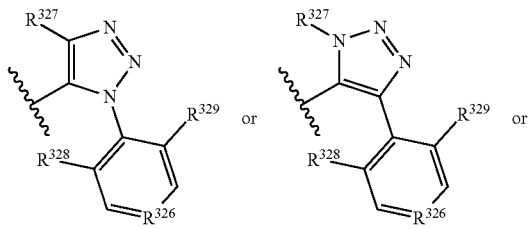

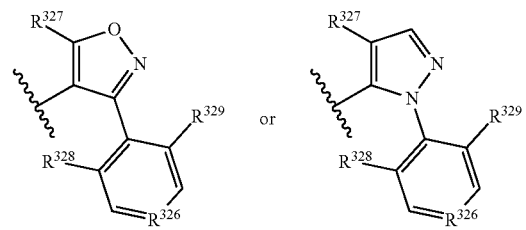

wherein $R^{326}$ is CH, N, NO;

$R^{327}$ is selected from the group consisting of hydrogen, $C_1$-$C_3$ alkyl, $C_1$-$C_3$ haloalkyl, $C_3$-$C_6$ cylcoalkyl, $C_4$-$C_5$ alkylcycloalkyl;

$R^{328}$ and $R^{329}$ are independently selected from the group consisting of hydrogen, $C_1$-$C_3$ alkyl, $C_1$-$C_3$ haloalkyl, $C_1$-$C_3$ alkoxy, $C_1$-$C_3$ haloalkoxy and halogen.

In some embodiments, compounds having formula XV may also have formula XVI

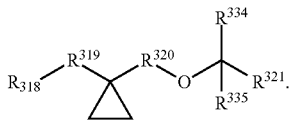

In other embodiments, compounds having formula XV, may also have the formula XVII,

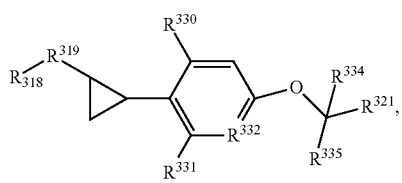

wherein $R^{332}$ is CH, CD or N;

$R^{330}$ and $R^{331}$ are independently selected from the group consisting of H, D, lower alkyl, halogen and $CF_3$;

$R^{318}$-$R^{319}$ is selected from

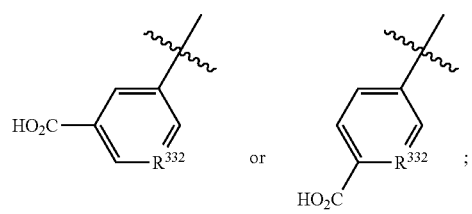

$R^{327}$ is selected from the group consisting of isopropyl, t-butyl and cyclopropyl;

$R^{328}$ and $R^{329}$ are independently selected from the group consisting of halogen, $C_1$-$C_3$ alkyl, methoxy and trifluoromethoxy;

$R^{334}$ and $R^{335}$ are each independently H or D. In some embodiments, at least one of $R^{334}$ and $R^{335}$ are D.

In other embodiments for compounds having the formula XV, XVI or XVII, wherein $R^{319}$ is phenyl;

$R^{320}$ is optionally substituted phenyl, preferably substituted with one substituent, preferably halogen, or two substituents, preferably both halogen or one halogen one deuterium;

$R^{326}$ is CH;

$R^{327}$ is cycloalkyl; and $R^{328}$ and $R^{329}$ each are halogen.

Exemplary compounds having formula XV, XVI or XVII include:

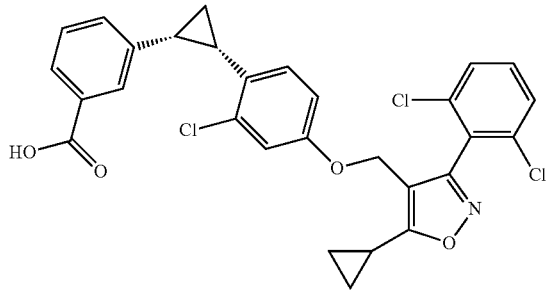

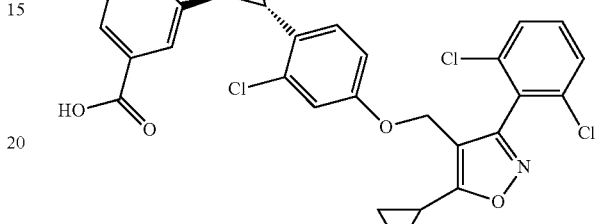

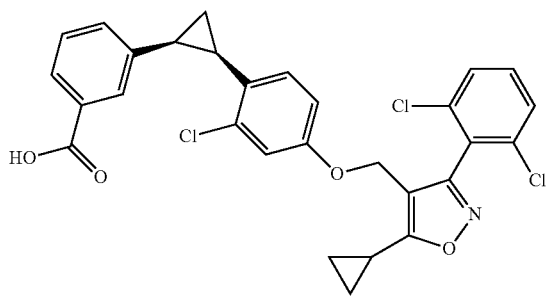

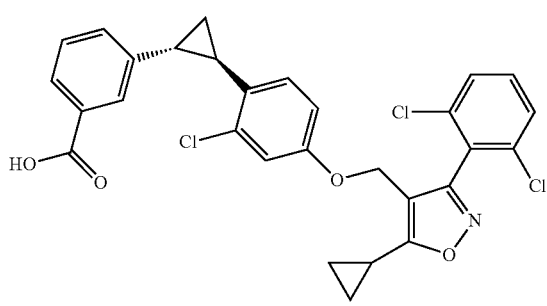

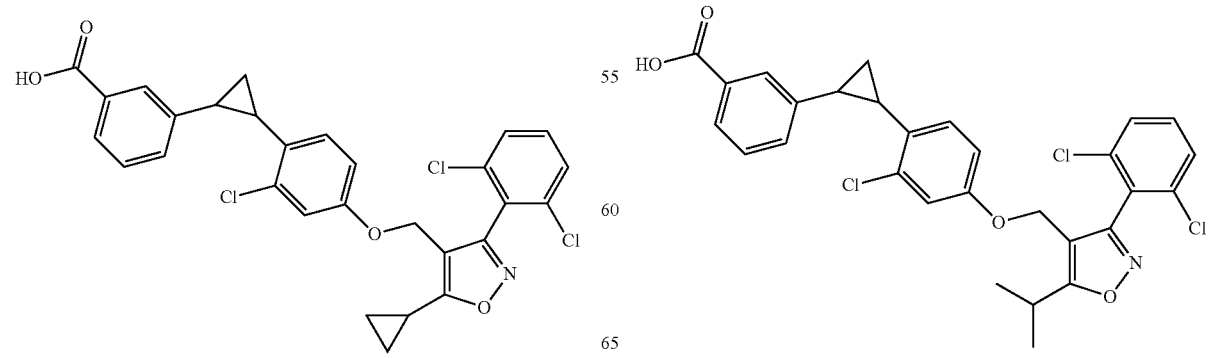

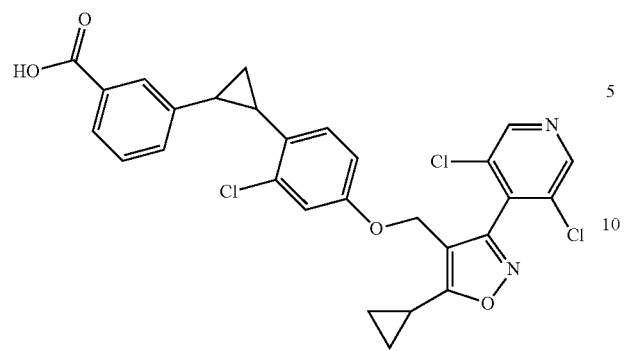
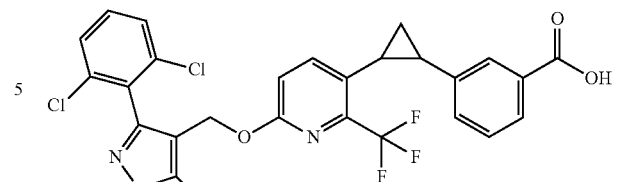
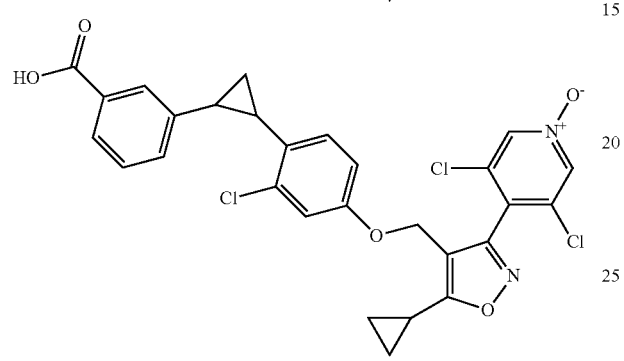
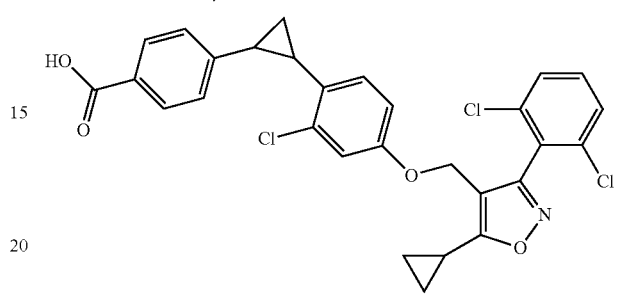
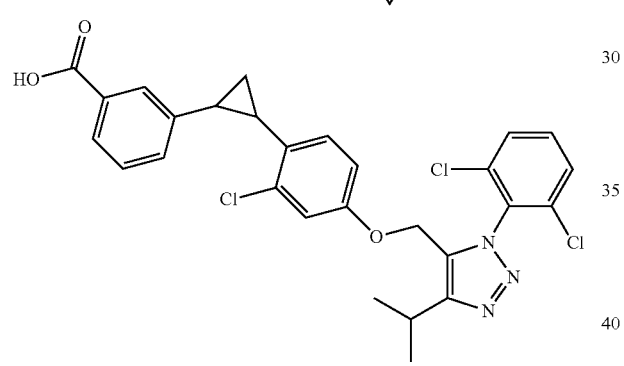
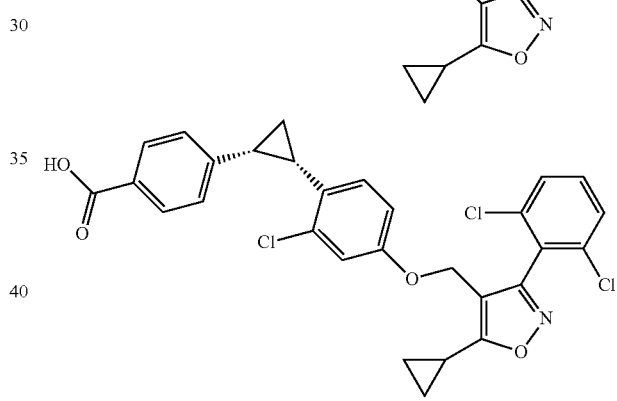
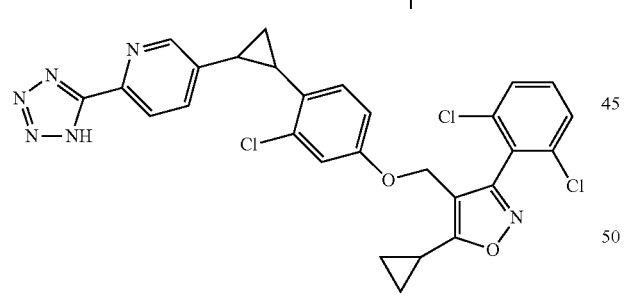
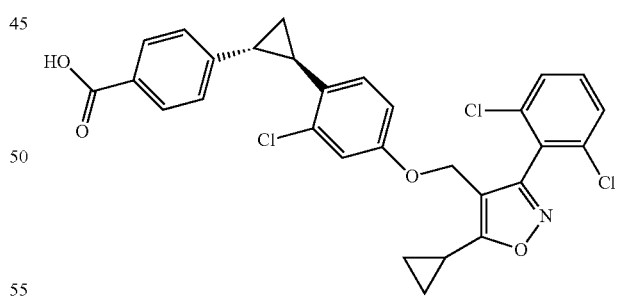
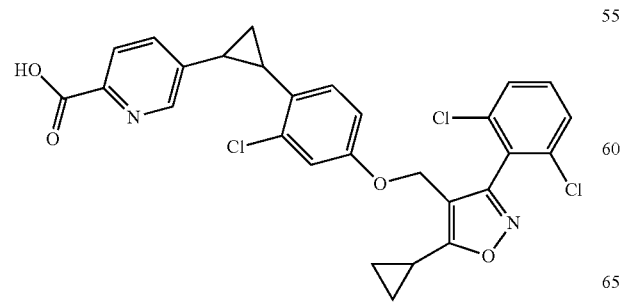
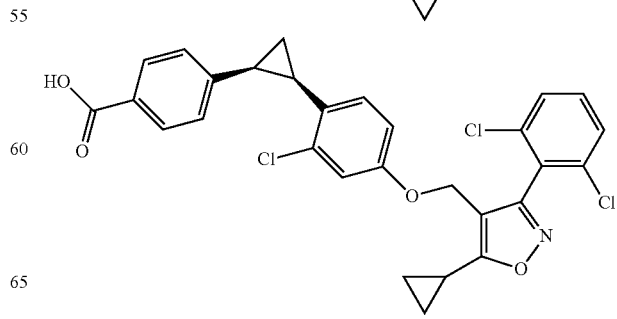

-continued
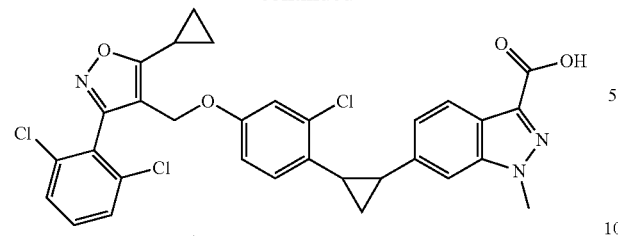
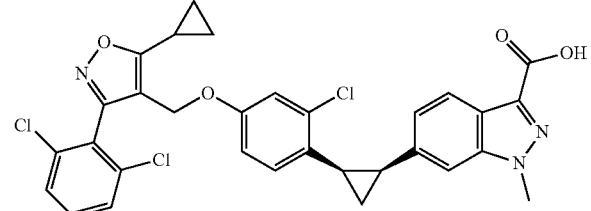
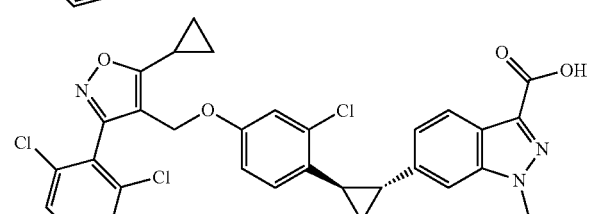
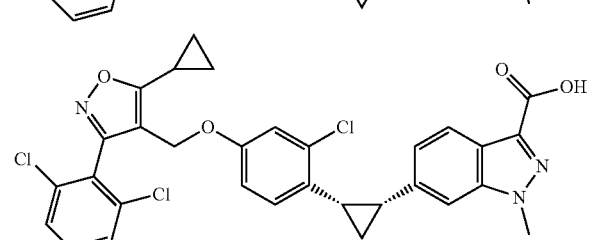
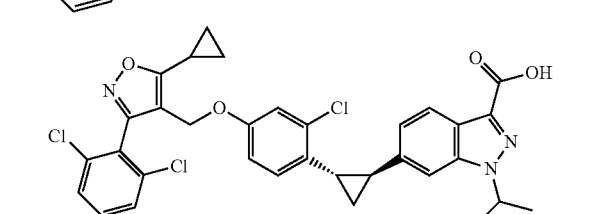
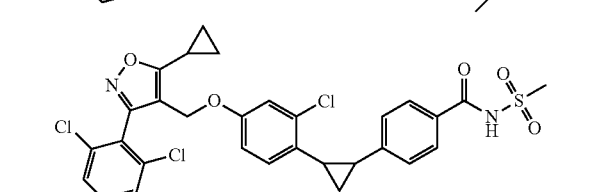
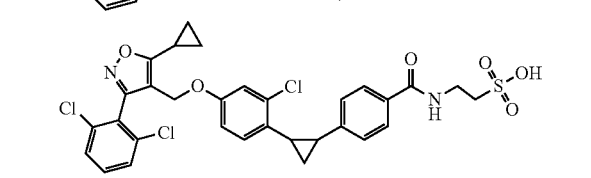
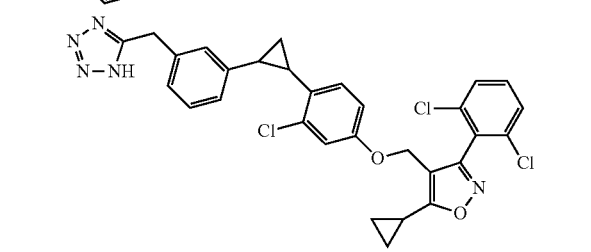
-continued
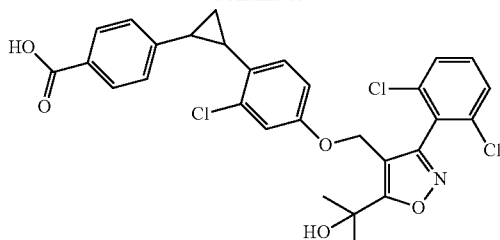
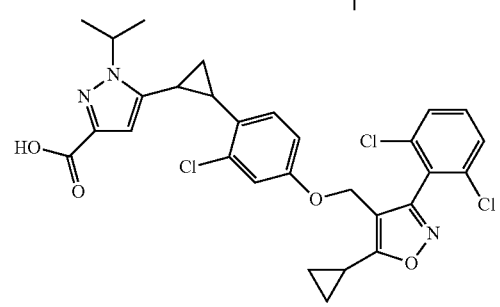
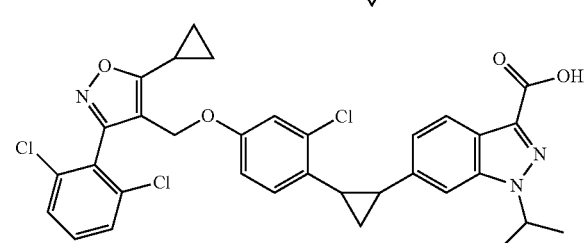
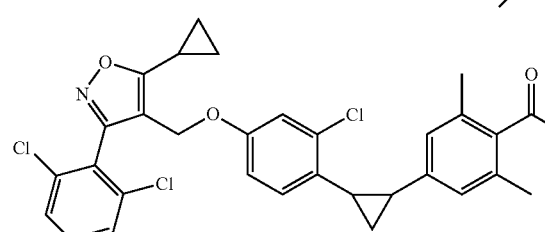
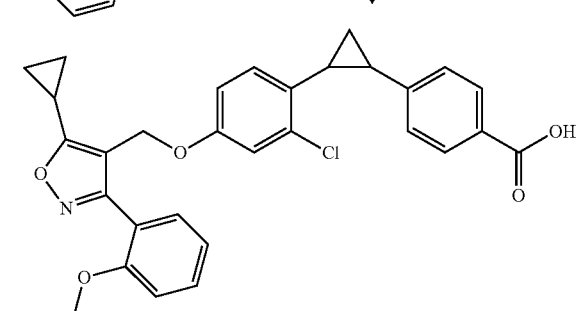
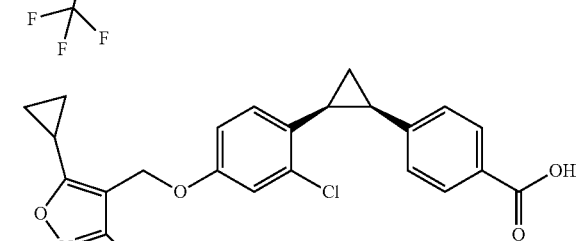
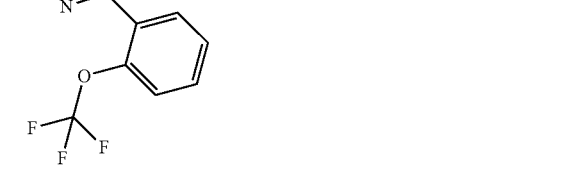

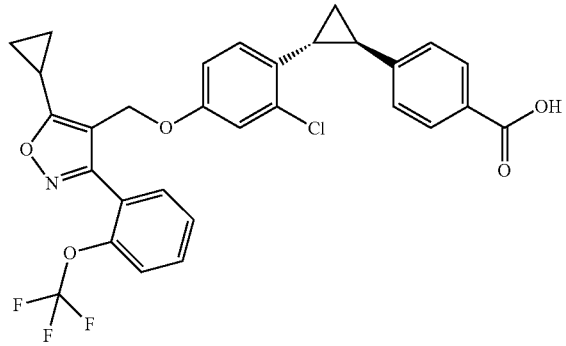
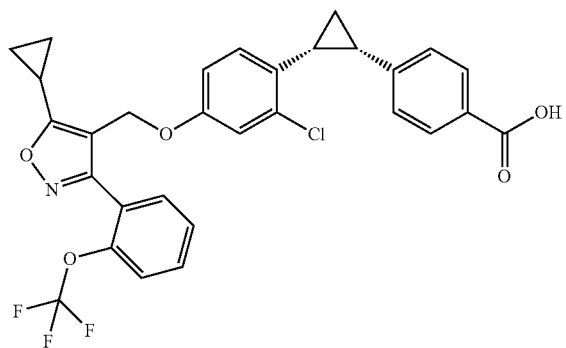
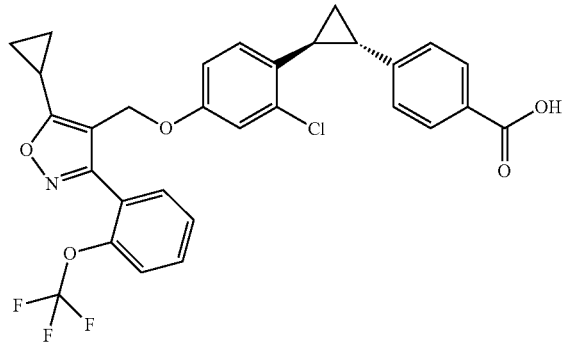
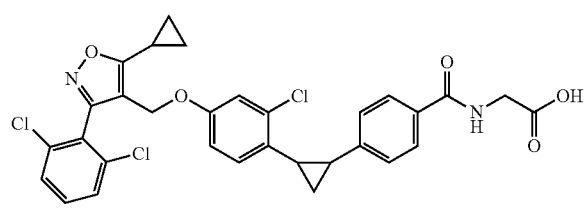
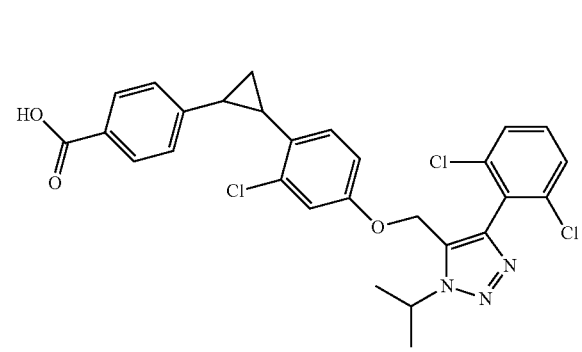
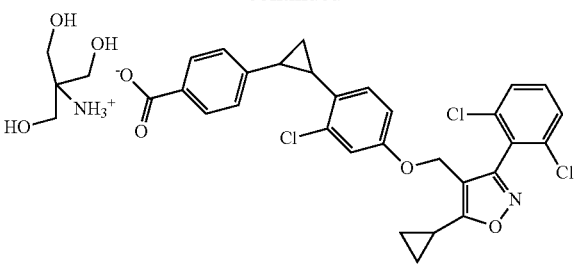
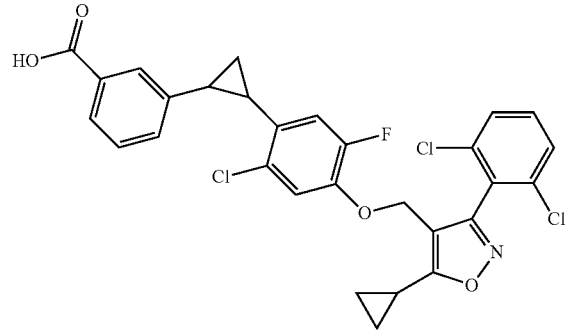
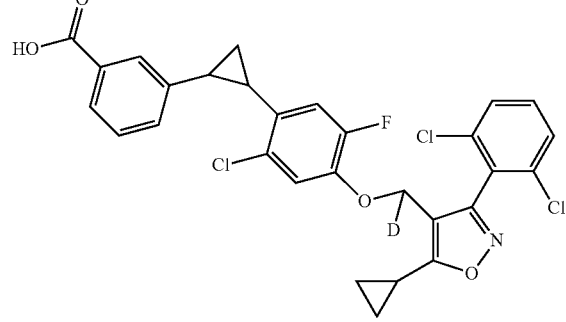
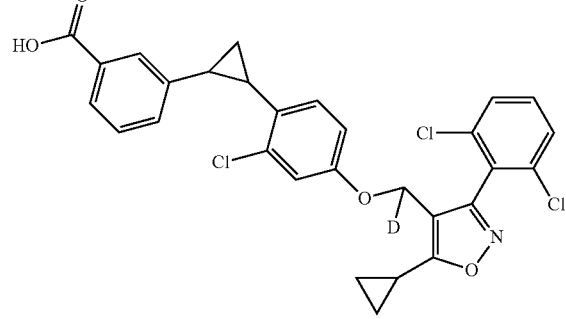
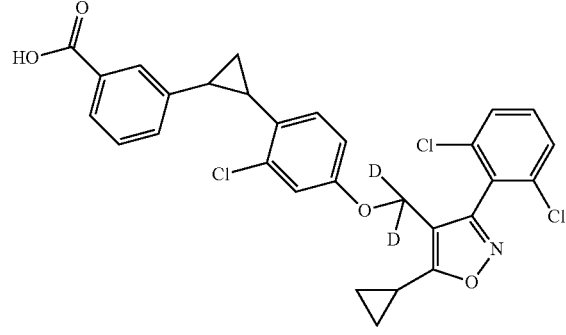

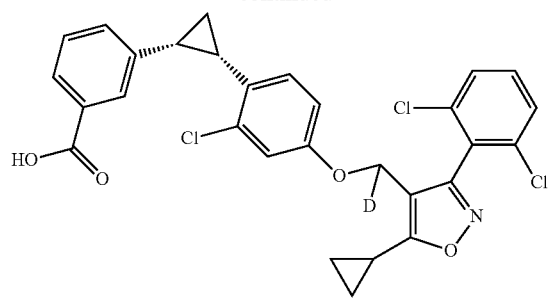
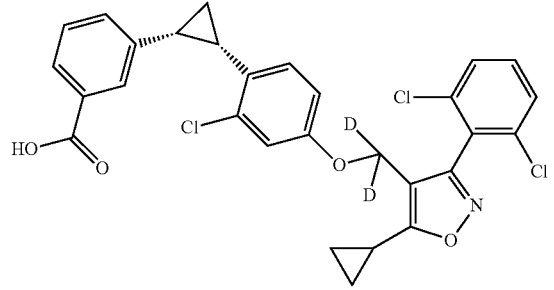
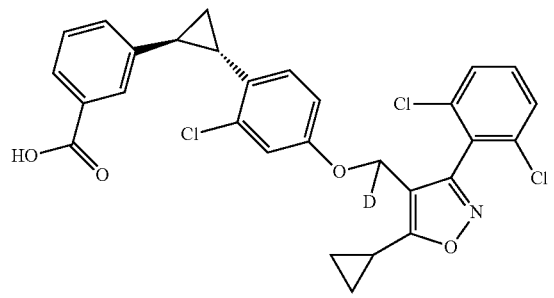
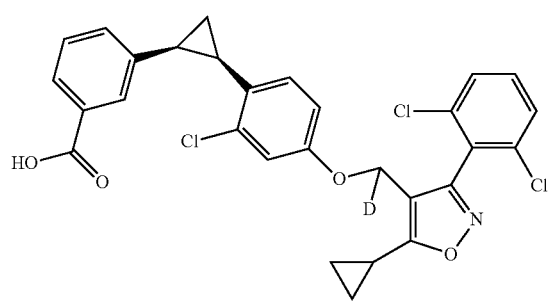
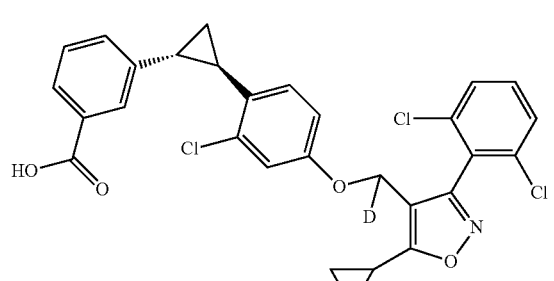
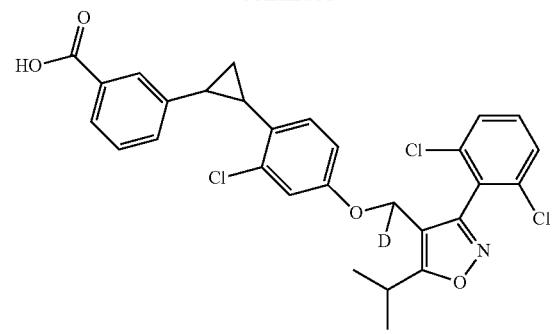
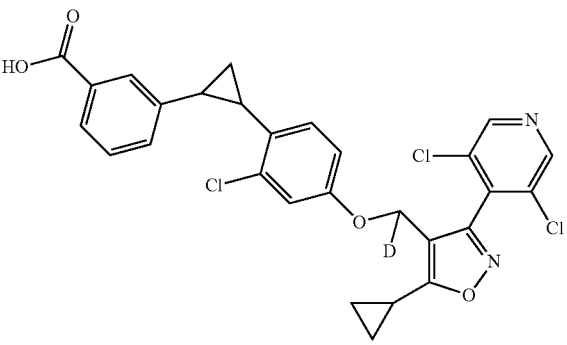
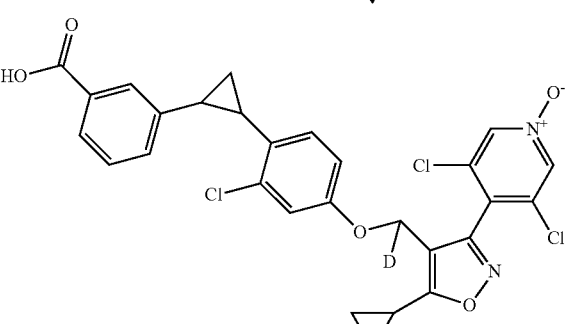
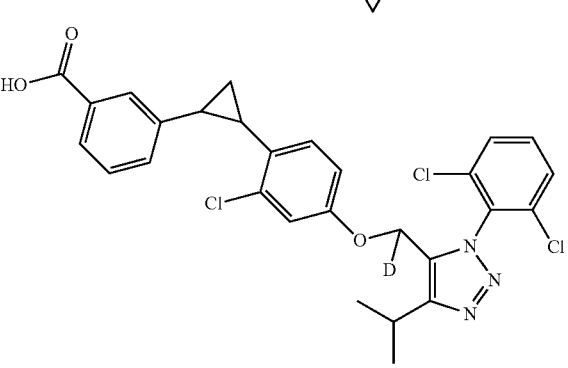
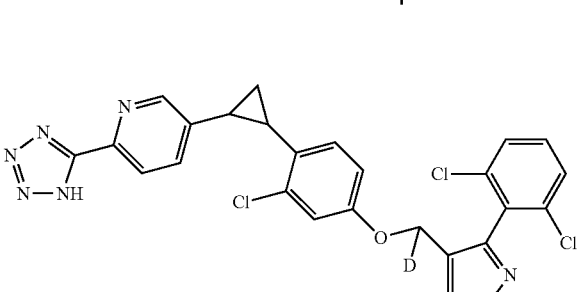

73
-continued
74
-continued
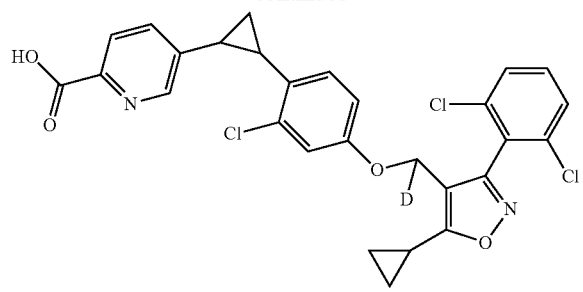
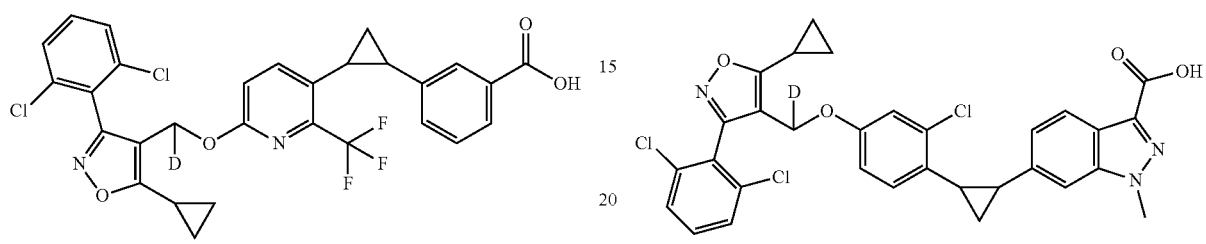
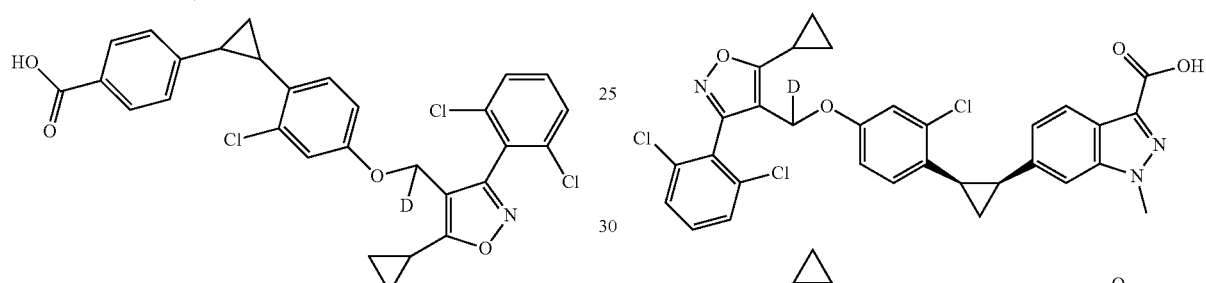
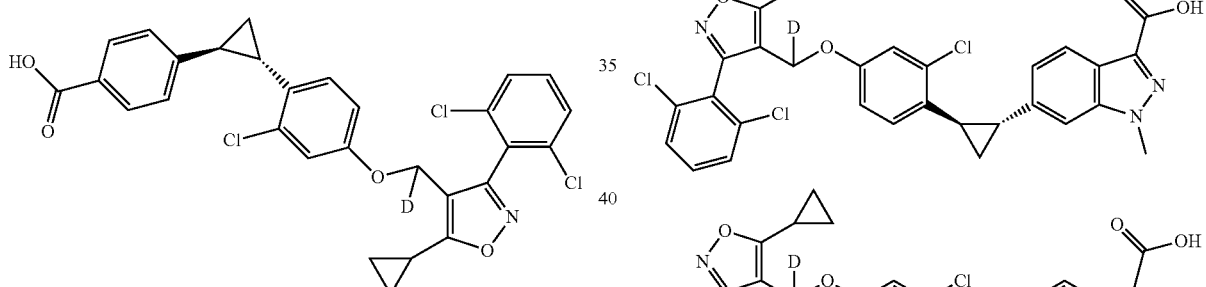
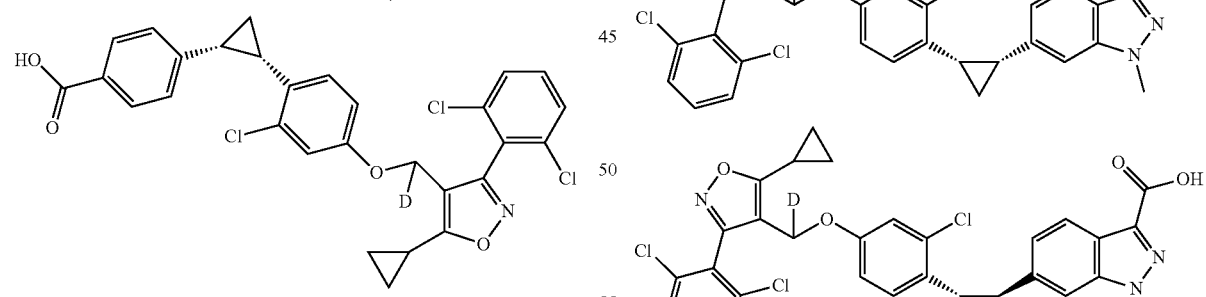
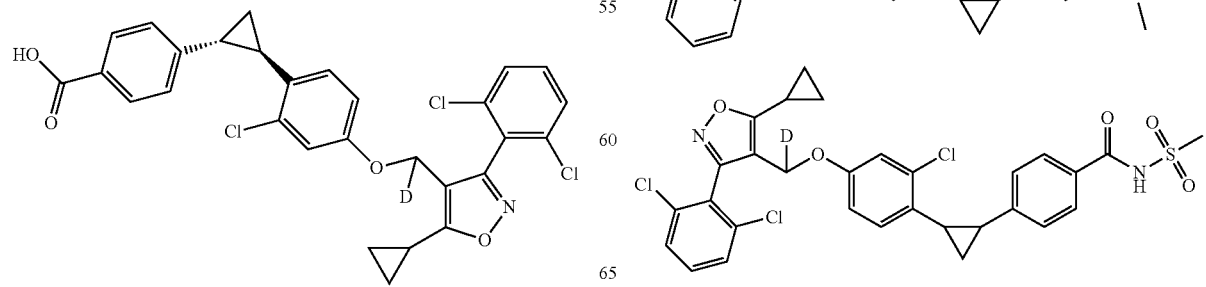

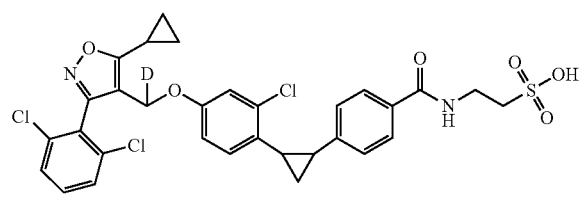
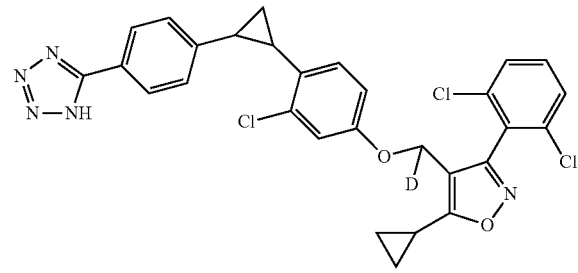
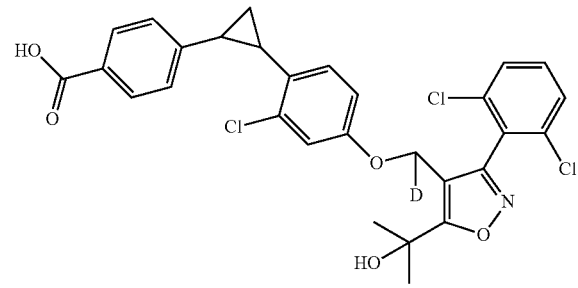
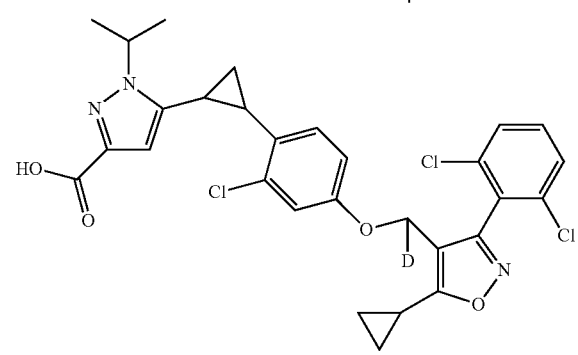
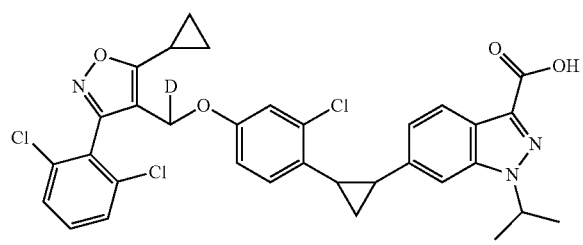
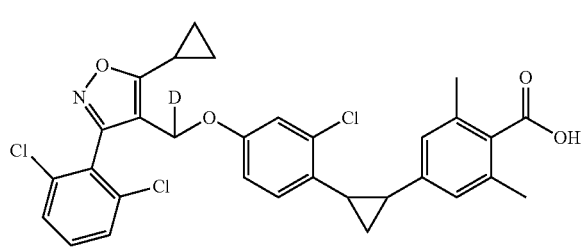
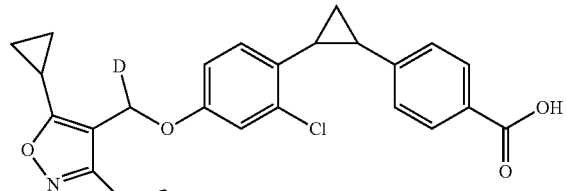
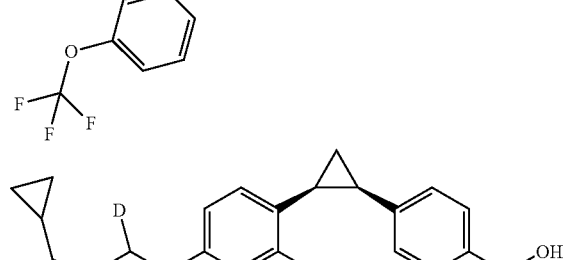
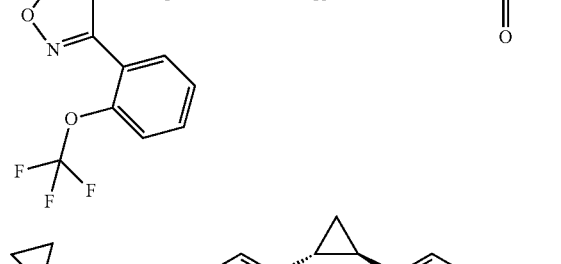
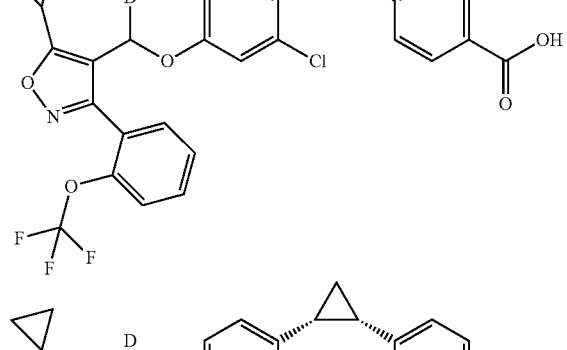
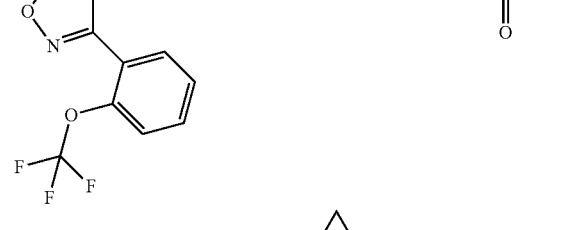
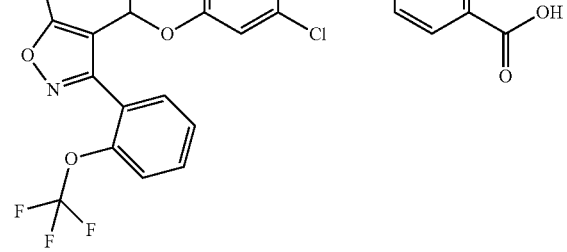

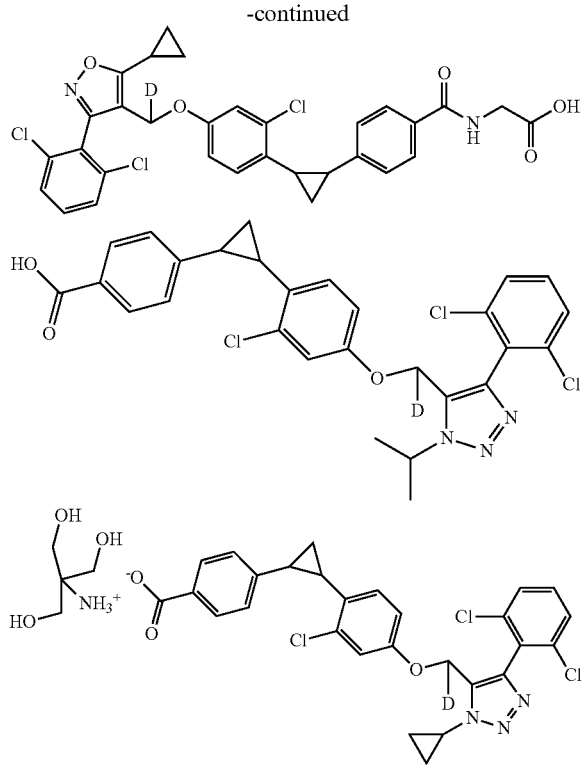

3-(2-(2-chloro-4-((5-cyclopropyl-3-(2,6-dichlorophenyl)isoxazol-4-yl)methoxy)phenyl)cyclopropyl)benzoic acid,
(−)-3-(2-(2-chloro-4-((5-cyclopropyl-3-(2,6-dichlorophenyl)isoxazol-4-yl)methoxy)phenyl)cyclopropyl)benzoic acid,
3-((1R,2R)-2-(2-chloro-4-((5-cyclopropyl-3-(2,6-dichlorophenyl)isoxazol-4-yl)methoxy)phenyl)cyclopropyl)benzoic acid,
3-((1S,2R)-2-(2-chloro-4-((5-cyclopropyl-3-(2,6-dichlorophenyl)isoxazol-4-yl)methoxy)phenyl)cyclopropyl)benzoic acid,
3-((1S,2S)-2-(2-chloro-4-((5-cyclopropyl-3-(2,6-dichlorophenyl)isoxazol-4-yl)methoxy)phenyl)cyclopropyl)benzoic acid,
3-((1R,2S)-2-(2-chloro-4-((5-cyclopropyl-3-(2,6-dichlorophenyl)isoxazol-4-yl)methoxy)phenyl)cyclopropyl)benzoic acid,
(+)-3-(2-(2-chloro-4-((5-cyclopropyl-3-(2,6-dichlorophenyl)isoxazol-4-yl)methoxy)phenyl)cyclopropyl)benzoic acid,
3-(2-(2-chloro-4-((3-(2,6-dichlorophenyl)-5-isopropylisoxazol-4-yl)methoxy)phenyl)cyclopropyl)benzoic acid,
3-(2-(2-chloro-4-((5-cyclopropyl-3-(3,5-dichloropyridin-4-yl)isoxazol-4-yl)methoxy)phenyl)cyclopropyl)benzoic acid,
4-(4-((4-(2-(3-carboxyphenyl)cyclopropyl)-3-chlorophenoxy)methyl)-5-cyclopropylisoxazol-3-yl)-3,5-dichloropyridine 1-oxide,
3-(2-(2-chloro-4-((1-(2,6-dichlorophenyl)-4-isopropyl-1H-1,2,3-triazol-5-yl)methoxy)phenyl)cyclopropyl)benzoic acid,
4-((4-(2-(6-(1H-tetrazol-5-yl)pyridin-3-yl)cyclopropyl)-3-chlorophenoxy)methyl)-5-cyclopropyl-3-(2,6-dichloropheny)isoxazole,
5-(2-(2-chloro-4-((5-cyclopropyl-3-(2,6-dichlorophenyl)isoxazol-4-yl)methoxy)phenyl)cyclopropyl)picolinic acid.

3-(2-(6-((5-cyclopropyl-3-(2,6-dichlorophenyl)isoxazol-4-yl)methoxy)-2-(trifluoromethy)pyridin-3-yl)cyclopropyl)benzoic acid,
4-(2-(2-chloro-4-((5-cyclopropyl-3-(2,6-dichlorophenyl)isoxazol-4-yl)methoxy)phenyl)cyclopropyl)benzoic acid,
1,3-dihydroxy-2-(hydroxymethyl)propan-2-aminium 4-(2-(2-chloro-4-((5-cyclopropyl-3-(2,6-dichlorophenyl)isoxazol-4-yl)methoxy)phenyecyclopropyl)benzoate,
(+)-4-(2-(2-chloro-4-((5-cyclopropyl-3-(2,6-dichlorophenyl)isoxazol-4-yl)methoxy)phenyl)cyclopropyl)benzoic acid,
4-((1S,2R)-2-(2-chloro-4-((5-cyclopropyl-3-(2,6-dichlorophenyl)isoxazol-4-yl)methoxy)phenyl)cyclopropyl)benzoic acid,
4-((1R,2R)-2-(2-chloro-4-((5-cyclopropyl-3-(2,6-dichlorophenyeisoxazol-4-yl)methoxy)phenyl)cyclopropyl)benzoic acid,
4-((1R,2S)-2-(2-chloro-4-((5-cyclopropyl-3-(2,6-dichlorophenyl)isoxazol-4-yl)methoxy)phenyl)cyclopropyl)benzoic acid,
4-((1S,2S)-2-(2-chloro-4-((5-cyclopropyl-3-(2,6-dichlorophenyl)isoxazol-4-yl)methoxy)phenyl)cyclopropyl)benzoic acid,
(−)-4-(2-(2-chloro-4-((5-cyclopropyl-3-(2,6-dichlorophenyl)isoxazol-4-yl)methoxy)phenyl)cyclopropyl)benzoic acid,
6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid,
(+)-6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid,
6-((1S,2R)-2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid,
6-((1R,2R)-2-(2-chloro-4-((5-cyclopropyl-3-(2,6-dichlorophenyeisoxazol-4-yl)methoxy)phenyl)cyclopropyl)-1-methyl-1H-indazole-3-carboxylic acid,
6-((1R,2S)-2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid,
6-((1S,2S)-2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid, (−)-6-(2-(2-chloro-4-((5-cyclopropyl-3-(2,6-dichloropheny)isoxazol-4-yl)methoxy)phenyl)cyclopropyl)-1-methyl-1H-indazole-3-carboxylic acid,
4-(2-(2-chloro-4-((5-cyclopropyl-3-(2,6-dichlorophenyl)isoxazol-4-yl)methoxy)phenyl)cyclopropyl)-N-(methylsulfonyebenzamide,
2-(4-(2-(2-chloro-4-((5-cyclopropyl-3-(2,6-dichlorophenyl)isoxazol-4-yl)methoxy)phenyl)cyclopropyl)benzamido)ethanesulfonic acid,
4-((4-(2-(4-(1H-tetrazol-5-yl)phenyl)cyclopropyl)-3-chlorophenoxy)methyl)-5-cyclopropyl-3-(2,6-dichlorophenyeisoxazole,
4-(2-(2-chloro-4-((3(2,6-dichlorophenyl)-5-(2-hydroxypropan-2-yl)isoxazol-4-yl)methoxy)phenyl)cyclopropyl)benzoic acid,
5-(2-(2-chloro-4-((5-cyclopropyl-3-(2,6-dichlorophenyl)isoxazol-4-yl)methoxy)phenyl)cyclopropyl)-1-isopropyl-1H-pyrazole-3-carboxylic acid,
6-(2-(2-chloro-4-((5-cyclopropyl-3-(2,6-dichlorophenyl)isoxazol-4-yl)methoxy)phenyl)cyclopropyl)-1-isopropyl-1H-indazole-3-carboxylic acid, 4-(2-(2-chloro-4-((5-cyclopropyl-3-(2,6-dichlorophenyl)isoxazol-4-yl)methoxy)phenyl)cyclopropyl)-2,6-dimethylbenzoic acid, 4-(2-(2-chloro-4-((5-cyclopropyl-3-(2-(trifluoromethoxy)phenyl)isoxazol-4-yl)methoxy)phenyl)cyclopropyl)benzoic acid,
(+)-2-(4-(2-(2-chloro-4-((5-cyclopropyl-3-(2,6-dichlorophenyl)isoxazol-4-yl)methoxy)phenyl)cyclopropyl)benzamido)ethanesulfonic acid,
4-((1R,2S)-2-(2-chloro-4-((5-cyclopropyl-3-(2-(trifluoromethoxy)phenyl)isoxazol-4-yl)methoxy)phenyl)cyclopropyl)benzoic acid,
4-((1R,2R)-2-(2-chloro-4-((5-cyclopropyl-3-(2-(trifluoromethoxy)phenyl)isoxazol-4-yl)methoxy)phenyl)cyclopropyl)benzoic acid,
4-((1S,2R)-2-(2-chloro-4-((5-cyclopropyl-3-(2-(trifluoromethoxy)phenyl)isoxazol-4-yl)methoxy)phenyl)cyclopropyl)benzoic acid,
4-((1S,2S)-2-(2-chloro-4-((5-cyclopropyl-3-(2-(trifluoromethoxy)phenyisoxazol-4-yl)methoxy)phenyl)cyclopropyl)benzoic acid,
(−)-2-(4-(2-(2-chloro-4-((5-cyclopropyl-3-(2,6-dichlorophenyl)isoxazol-4-yl)methoxy)phenyl)cyclopropyl)benzamido)ethanesulfonic acid,
2-(4-(2-(2-chloro-4-((5-cyclopropyl-3-(2,6-dichlorophenyl)isoxazol-4-yl)methoxy)phenyl)cyclopropyl)benzamido)acetic acid,
4-(2-(2-chloro-4-((4-(2,6-dichlorophenyl)-1-isopropyl-1H-1,2,3-triazol-5-yl)methoxy)phenyl)cyclopropyl)benzoic acid,
3-(2-(2-chloro-4-((5-cyclopropyl-3-(2,6-dichlorophenyl)isoxazol-4-yl)methoxy)-5-fluorophenyl)cyclopropyl)benzoic acid,
3-(2-(2-chloro-4-((5-cyclopropyl-3-(2,6-dichlorophenyl)isoxazol-4-yl)methoxy-d)-5-fluorophenyl)cyclopropyl)benzoic acid,
3-(2-(2-chloro-4-((5-cyclopropyl-3-(2,6-dichlorophenyl)isoxazol-4-yl)methoxy-d)phenyl)cyclopropyl)benzoic acid,
3-(2-(2-chloro-4-((5-cyclopropyl-3-(2,6-dichlorophenyl)isoxazol-4-yl)methoxy-d2)phenyl)cyclopropyl)benzoic acid,
3-((1R,2S)-2-(2-chloro-4-((5-cyclopropyl-3-(2,6-dichlorophenyl)isoxazol-4-yl)methoxy-d)phenyl)cyclopropyl)benzoic acid,
3-((1R,2S)-2-(2-chloro-4-((5-cyclopropyl-3-(2,6-dichlorophenyl)isoxazol-4-yl)methoxy-d2)phenyl)cyclopropyl)benzoic acid,
3-((1S,2S)-2-(2-chloro-4-((5-cyclopropyl-3-(2,6-dichlorophenyl)isoxazol-4-yl)methoxy-d)phenyl)cyclopropyl)benzoic acid,
3-((1S,2R)-2-(2-chloro-4-((5-cyclopropyl-3-(2,6-dichlorophenyl)isoxazol-4-yl)methoxy-d)phenyl)cyclopropyl)benzoic acid,
3-((1R,2R)-2-(2-chloro-4-((5-cyclopropyl-3-(2,6-dichlorophenyeisoxazol-4-yl)methoxy-d)phenyl)cyclopropyl)benzoic acid,
3-(2-(2-chloro-4-((3-(2,6-dichlorophenyl)-5-isopropylisoxazol-4-yl)methoxy-d)phenyl)cyclopropyl)benzoic acid,
5-(2-(2-chloro-4-((5-cyclopropyl-3-(2,6-dichlorophenyl)isoxazol-4-yl)methoxy-d)phenyl)cyclopropyl)picolinic acid,
3-(2-(6-((5-cyclopropyl-3-(2,6-dichlorophenyl)isoxazol-4-yl)methoxy-d)-2-(trifluoromethyl)pyridin-3-yl)cyclopropyl)benzoic acid,
4-(2-(2-chloro-4-((5-cyclopropyl-3-(2,6-dichlorophenyl)isoxazol-4-yl)methoxy-d)phenyl)cyclopropyl)benzoic acid,
4-((1S,2S)-2-(2-chloro-4-((5-cyclopropyl-3-(2,6-dichlorophenyl)isoxazol-4-yl)methoxy-d)phenyl)cyclopropyl)benzoic acid,
4-((1R,2S)-2-(2-chloro-4-((5-cyclopropyl-3-(2,6-dichlorophenyl)isoxazol-4-yl)methoxy-d)phenyl)cyclopropyl)benzoic acid,
4-((1R,2R)-2-(2-chloro-4-((5-cyclopropyl-3-(2,6-dichlorophenyeisoxazol-4-yl)methoxy-d)phenyl)cyclopropyl)benzoic acid,
4-((1S,2R)-2-(2-chloro-4-((5-cyclopropyl-3-(2,6-dichlorophenyl)isoxazol-4-yl)methoxy-d)phenyl)cyclopropyl)benzoic acid,
6-(2-(2-chloro-4-((5-cyclopropyl-3-(2,6-dichlorophenyl)isoxazol-4-yl)methoxy-d)phenyl)cyclopropyl)-1-methyl-1H-indazole-3-carboxylic acid,
6-((1S,2R)-2-(2-chloro-4-((5-cyclopropyl-3-(2,6-dichlorophenyl)isoxazol-4-yl)methoxy-d)phenyl)cyclopropyl)-1-methyl-1H-indazole-3-carboxylic acid,
6-((1R,2R)-2-(2-chloro-4-((5-cyclopropyl-3-(2,6-dichlorophenyeisoxazol-4-yl)methoxy-d)phenyl)cyclopropyl)-1-methyl-1H-indazole-3-carboxylic acid,
6-((1R,2S)-2-(2-chloro-4-((5-cyclopropyl-3-(2,6-dichlorophenyl)isoxazol-4-yl)methoxy-d)phenyl)cyclopropyl)-1-methyl-1H-indazole-3-carboxylic acid,
6-((1S,2S)-2-(2-chloro-4-((5-cyclopropyl-3-(2,6-dichlorophenyl)isoxazol-4-yl)methoxy-d)phenyl)cyclopropyl)-1-methyl-1H-indazole-3-carboxylic acid,
4-(2-(2-chloro-4-((5-cyclopropyl-3-(2,6-dichlorophenyl)isoxazol-4-yl)methoxy-d)phenyl)cyclopropyl)-N-(methylsulfonyl)benzamide,
2-(4-(2-(2-chloro-4-((5-cyclopropyl-3-(2,6-dichlorophenyl)isoxazol-4-yl)methoxy-d)phenyl)cyclopropyl)benzamido)ethane-1-sulfonic acid,
4-((4-(2-(4-(1H-tetrazol-5-yl)phenyl)cyclopropyl)-3-chlorophenoxy)methyl-d)-5-cyclopropyl-3-(2,6-dichlorophenyeisoxazole,
4-(2-(2-chloro-4-((3-(2,6-dichlorophenyl)-5-(2-hydroxypropan-2-yl)isoxazol-4-yl)methoxy-d)phenyl)cyclopropyl)benzoic acid,
5-(2-(2-chloro-4-((5-cyclopropyl-3-(2,6-dichlorophenyl)isoxazol-4-yl)methoxy-d)phenyl)cyclopropyl)-1-isopropyl-1H-pyrazole-3-carboxylic acid,
6-(2-(2-chloro-4-((5-cyclopropyl-3-(2,6-dichlorophenyl)isoxazol-4-yl)methoxy-d)phenyl)cyclopropyl)-1-isopropyl-1H-indazole-3-carboxylic acid,
4-(2-(2-chloro-4-((5-cyclopropyl-3-(2,6-dichlorophenyl)isoxazol-4-yl)methoxy-d)phenyl)cyclopropyl)-2,6-dimethylbenzoic acid,
4-(2-(2-chloro-4-((5-cyclopropyl-3-(2-(trifluoromethoxy)phenyl)isoxazol-4-yl)methoxy-d)phenyl)cyclopropyl)benzoic acid,
4-((1R,2S)-2-(2-chloro-4-((5-cyclopropyl-3-(2-(trifluoromethoxy)phenyl)isoxazol-4-yl)methoxy-d)phenyl)cyclopropyl)benzoic acid,
4-((1R,2R)-2-(2-chloro-4-((5-cyclopropyl-3-(2-(trifluoromethoxy)phenyl)isoxazol-4-yl)methoxy-d)phenyl)cyclopropyl)benzoic acid,
4-((1S,2R)-2-(2-chloro-4-((5-cyclopropyl-3-(2-(trifluoromethoxy)phenyl)isoxazol-4-yl)methoxy-d)phenyl)cyclopropyl)benzoic acid,
4-((1S,2S)-2-(2-chloro-4-((5-cyclopropyl-3-(2-(trifluoromethoxy)phenyl)isoxazol-4-yl)methoxy-d)phenyl)cyclopropyl)benzoic acid,
(4-(2-(2-chloro-4-((5-cyclopropyl-3-(2,6-dichlorophenyl)isoxazol-4-yl)methoxy-d)phenyl)cyclopropyl)benzoyl)glycine, 4-(2-(2-chloro-4-((4-(2,6-dichlorophenyl)-1-isopropyl-1H-1,2,3-triazol-5-yl)methoxy-d)phenyl)cyclopropyl)benzoic acid, 1,3-dihydroxy-2-(hydroxymethyl)propan-2-aminium 4-(2-(2-chloro-4-((5-cyclopropyl-3-(2,6-dichlorophenyl)isoxazol-4-yl)methoxy-d)phenyl)cyclopropyl)benzoate.

Also provided herein are kits that include any FXR agonist (or composition containing such an agonist) described herein and a device for localized delivery within a region of the intestines, such as the ileum or colon. In certain embodiments, the device is a syringe, bag, or a pressurized container.

IV. Compositions

Also disclosed herein are pharmaceutical compositions comprising at least one compound having formulas I-III. Remington's Pharmaceutical Sciences, by E. W. Martin, Mack Publishing Co., Easton, Pa., 15th Edition, 1975, incorporated herein by reference, describes exemplary formulations (and components thereof) suitable for pharmaceutical delivery of the disclosed compounds. Pharmaceutical compositions comprising at least one of the disclosed compounds can be formulated for use in human or veterinary medicine. Particular formulations of a disclosed pharmaceutical composition may depend, for example, on the mode of administration (e.g., oral). In some embodiments, disclosed pharmaceutical compositions include a pharmaceutically acceptable carrier in addition to at least one or two or more active ingredients, such as a compound or compounds disclosed herein. In other embodiments, other medicinal or pharmaceutical agents, for example, with similar, related or complementary effects on the affliction being treated (such as obesity, dyslipidemia, or diabetes), can also be included as active ingredients in a pharmaceutical composition. For example, one or more of the disclosed compounds can be formulated with one or more of (such as 1, 2, 3, 4, or 5 of) an antibiotic (e.g., metronidazole, vancomycin, and/or fidaxomicin), statin, alpha-glucosidase inhibitor, amylin agonist, dipeptidyl-peptidase 4 (DPP-4) inhibitor (such as sitagliptin, vildagliptin, saxagliptin, linagliptin, anaglptin, teneligliptin, alogliptin, gemiglptin, or dutoglpitin), meglitinide, sulfonylurea, peroxisome proliferator-activated receptor (PPAR)-gamma agonist (e.g., a thiazolidinedione (TZD) [such as ioglitazone, rosiglitazone, rivoglitazone, or troglitazone], aleglitazar, farglitazar, muraglitazar, or tesaglitazar), anti-inflammatory agent (e.g., oral corticosteroid), chemotherapeutic, biologic, radiotherapeutic, nicotinamide ribonucleoside, analogs of nicotinamide ribonucleoside (such as those that promote NAD+ production of which is a substrate for many enzymatic reactions such as p450s which are a target of FXR, for example see Yang et al., *J. Med Chem.* 50: 6458-61, 2007, herein incorporated by reference), and the like.

Pharmaceutically acceptable carriers useful for the disclosed method and composition will depend on the particular mode of administration being employed. For example, for solid compositions (e.g., powder, pill, tablet, or capsule forms), conventional non-toxic solid carriers can include, without limitation, pharmaceutical grades of sugars, such as mannitol or lactose, polysaccharides, such as starch, or salts of organic acids, such as magnesium stearate. In addition to biologically neutral carriers, pharmaceutical compositions can optionally contain amounts of auxiliary substances (e.g., excipients), such as wetting or emulsifying agents, preservatives, and pH buffering agents and the like; for example, sodium acetate or sorbitan monolaurate. Other non-limiting excipients include nonionic solubilizers, such as cremophor, or proteins, such as human serum albumin or plasma preparations. In some embodiments, the pharmaceutical composition comprises a sufficient amount of a disclosed compound to have a desired therapeutic effect. Typically, the disclosed compound constitutes greater than 0% to less than 100% of the pharmaceutical composition, such as 10% or less, 20% or less, 30% or less, 40% or less, 50% or less, 60% or less, 70% or less, 80% or less, 90% or less, or 90% to less than 100% of the pharmaceutical composition.

The disclosed pharmaceutical compositions may be formulated as a pharmaceutically acceptable salt, solvate, hydrate, N-oxide or combination thereof, of a disclosed compound. Additionally, the pharmaceutical composition may comprise one or more polymorph of the disclosed compound. Pharmaceutically acceptable salts are salts of a free base form of a compound that possesses the desired pharmacological activity of the free base. These salts may be derived from inorganic or organic acids. Non-limiting examples of suitable inorganic acids include hydrochloric acid, nitric acid, hydrobromic acid, sulfuric acid, hydriodic acid, and phosphoric acid. Non-limiting examples of suitable organic acids include acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Examples of other suitable pharmaceutically acceptable salts are found in Remington's Pharmaceutical Sciences, 17th Edition, Mack Publishing Company, Easton, Pa., 1985.

In some embodiments, the compounds disclosed herein may be formulated to have a suitable particle size. A suitable particle size may be one which reduces or substantially precludes separation of the components of the composition, e.g., no separation between the drug and any other components of the composition, such as a second drug, a pharmaceutically acceptable excipient, a corticosteroid, an antibiotic or any combination thereof. Additionally, the particle size may be selected to ensure the composition is suitable for delivery, such as oral delivery.

In certain embodiments, the composition further includes an enteric coating. Typically, an enteric coating is a polymer barrier applied to an oral medication to help protect the drug from the acidity and/or enzymes of the stomach, esophagus and/or mouth. In some embodiments, this coating can reduce or substantially prevent systemic delivery of the disclosed compound, thereby allowing substantially selective delivery to the intestines. In some embodiments, the enteric coating will not dissolve in the acid environment of the stomach, which has an acidic, pH of about 3, but will dissolve in the alkaline environments of the small intestine, with, for example, a pH of about 7 to 9. Materials used for enteric coating include, but are not limited to, fatty acids, waxes, shellac, plastics and plant fibers. In some embodiments, the coating may comprise methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, or any combination thereof.

V. Methods of Making the Compounds

A person of ordinary skill in the art will understand how to make the compounds of formulas I-XVII. Additional information concerning the methods for making the disclosed compounds can be found in PCT application publication Nos. WO2003090745, WO2013007387 and WO2011020615, and in the Schemes below.

One exemplary embodiment of a general method of making a compound having formula I is shown in Scheme 1. This method is a modification of the method of Flatt, B. et al., *J. Med. Chem.* 2009, 52, 904-907, which is incorporated herein in its entirety. A person of ordinary skill in the art will appreciate that other suitable methods for making compounds having formula I can be determined.

Scheme 1

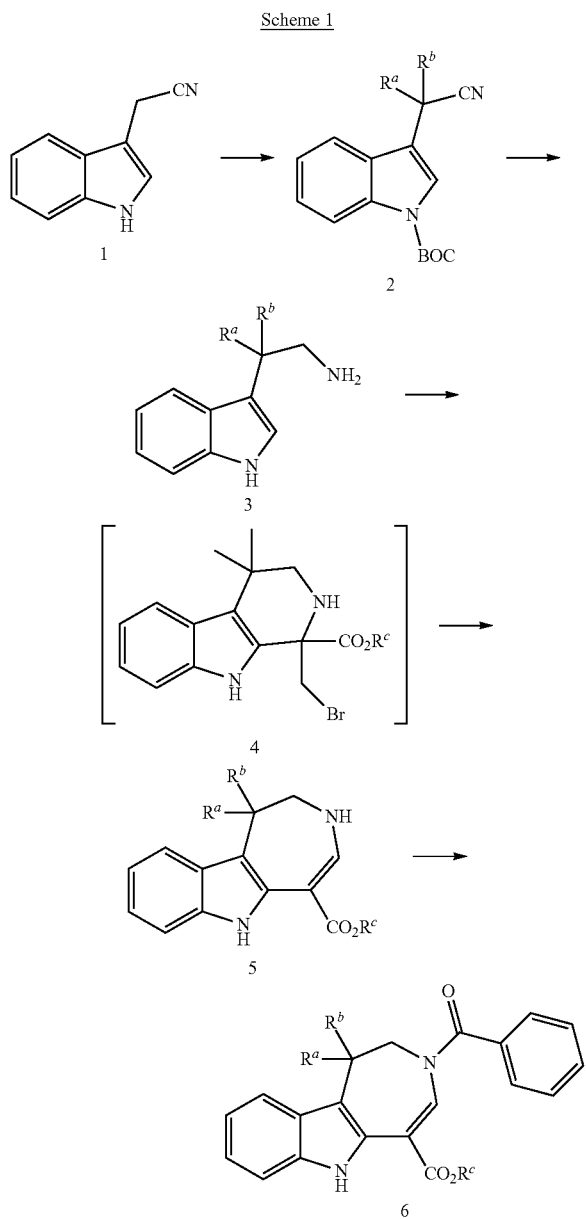

With reference to Scheme 1, an indole acetonitrile 1 is treated with a suitable protecting group. Scheme 1 illustrates using di-tert-butyl dicarbonate, in the presence of a base and in a suitable solvent, to form a BOC-protected indole (not shown). Suitable solvents include, but are not limited to, aprotic solvents, such as dichloromethane, dichloroethane, THF, chloroform, or combinations thereof. Suitable bases include, but are not limited to, triethylamine, 4-dimethylaminopyridine (DMAP), diiospropylethylamine, or combinations thereof. The BOC-protected indole is further reacted with lithium bis(trimethylsilyl)amide (LiHMDS) in a suitable, aprotic solvent such as THF or ether, and at a temperature effective to facilitate a reaction, to form compound 2. In some embodiments, the effective temperature is from about $-100°$ C. to about $-50°$ C., such as from about $-80°$ C. to about $-60°$ C. A suitable alkyl halide is then added to the reaction mixture, and the reaction mixture is warmed, or allowed to warm, to room temperature, such as to from about $20°$ C. to $25°$ C. A person of ordinary skill in the art will appreciate that the alkyl portion of the alkyl halide will correspond to the desired $R^a$ and/or $R^b$ group. For example, if $R^a$ and/or $R^b$ is methyl, a suitable alkyl halide may be methyl iodide. A person of ordinary skill in the art will also appreciate that if both $R^a$ and $R^b$ are alkyl, then an excess of LiHMDS and alkyl halide are used in the reaction, such as about 2.5 equivalents. However, if only one of $R^a$ or $R^b$ is alkyl, and the other is hydrogen, then only 1 equivalent of LiHMDS and alkyl halide is used.

Compound 2 is then deprotected, such as by removal of the BOC group, to form the deprotected indole compound (not shown). Suitable deprotection methods are known to persons of ordinary skill in the art and typically include reacting with an acid or acidic solution, including, but not limited to, trifluoroacetic acid or hydrochloric acid. The cyano group on the deprotected indole compound is then reduced by a suitable reducing agent, such as lithium aluminum hydride (LAH, LiAlH$_4$), at a temperature effective to facilitate a reaction, to form compound 3. Suitable solvents for the reduction reaction include any aprotic solvent that will not react with the reducing agent, such as THF and ethers. In some embodiments, the effective temperature is from about $20°$ C. to greater than $100°$ C., such as from about $40°$ C. to about $80°$ C.

Compound 3 is then reacted with a halopyruvate, such as $R^c$-bromopyruvate, where $R^c$ is the desired ester. The reaction is conducted in the presence of an acid, and in a suitable solvent and at an effective temperature, to form compound 4. Exemplary bromopyruvates include ethyl bromopyruvate and isopropyl bromopyruvate. Suitable acids include aqueous acid such as hydrochloric acid. Suitable solvents include protic solvents, such as alcohols. In some embodiments, ethanol is used as the solvent. Typically, the effective temperature is from about $20°$ C. to greater than $100°$ C., such as from about $50°$ C. to about $80°$ C.

Compound 4 is then reacted with a base at a temperature effective to form compound 5. Suitable bases include, but are not limited to, triethylamine, diisopropylethylamine, pyridine or combinations thereof. In some embodiments, the effective temperature is from about $20°$ C. to greater than $120°$ C., such as from about $50°$ C. to about $110°$ C.

Compound 5 is then reacted with a suitable acid or activated acid derivative, such as an acid chloride, to form the desired compound 6. The reaction is conducted in a suitable solvent, and in the presence of a suitable base. Suitable solvents include, but are not limited to, halogenated solvents such as chloroform, dichloroethane and dichloromethane, aprotic solvents such as DMF, DMSO, THF, acetonitrile, pyridine, toluene, or combinations thereof. Suitable bases include, but are not limited to, triethylamine, diisopropylethylamine, pyridine, potassium carbonate, sodium carbonate or sodium hydrogen carbonate. The reaction is conducted at a temperature effective to facilitate a reaction. In some embodiments, the effective temperature is from greater than 20° C. to greater than 120° C., such as from about 50° C. to about 100° C.

Another exemplary embodiment of a general method of making a compound having formula I is shown in Scheme 2. This method is a modification of the method disclosed by Wang, et al. *Tetrahedron Letters*, 2011, 52, 3295-3297, which is incorporated herein in its entirety.

Scheme 2

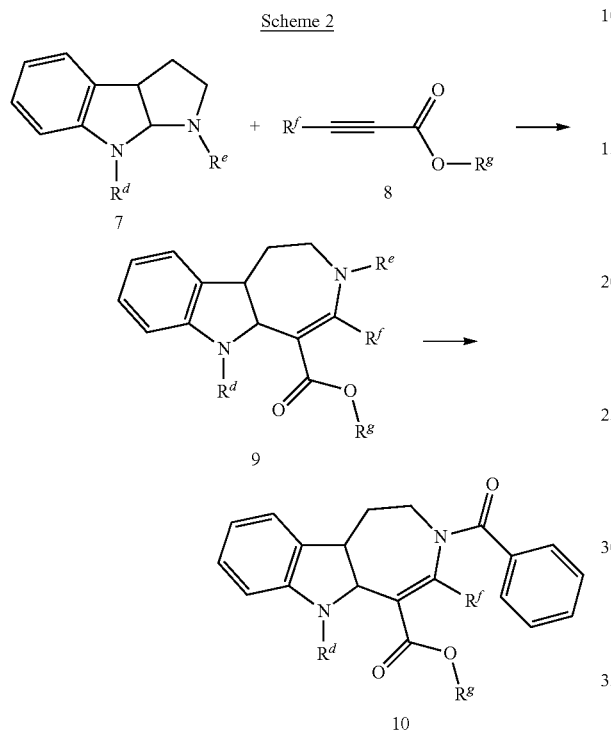

With reference to Scheme 2, a pyrroloindoline 7 is reacted with an acetylene ester 8 in a suitable solvent, and at a temperature effective to facilitate a reaction, to form compound 9. In some embodiments, the reaction is performed under an inert atmosphere, such as nitrogen or argon. Suitable solvents include, but are not limited to, polar, aprotic solvents such as DMF, DMSO or acetonitrile. In some embodiments, the effective temperature is from greater than 0° C. to greater than about 100° C., such as from about 10° C. to about 50° C., or about 20° C. to about 30° C. In some embodiments, the reaction proceeds in the presence of a catalyst. Suitable catalysts include, but are not limited to, copper halides, such as copper iodide, copper bromide, or copper chloride, salts of vitamin C such as sodium salt, potassium salt or lithium salt, or combinations thereof.

With reference to compound 9, $R^c$ can be hydrogen or methyl. In embodiments where $R^c$ is methyl, compound 9 is demethylated prior to acylation (not shown). The demethylation can be performed by any suitable method such as by reacting the tertiary amine with 1-chloroethylchloroformate in a suitable solvent. Solvents suitable for the demethylation include, but are not limited to, halogenated solvents such as dichloromethane, dichloroethane and chloroform, or THF. The reaction mixture is evaporated and then heated with an alcohol such as methanol for a time effective to form the secondary amine. The effective time is from greater than 1 minute to greater than 1 hour, such as from about 10 minutes to about 30 minutes.

Compound 9, or the demethylated compound 9, is then reacted with a suitable acid or activated acid derivative, such as an acid chloride, to form the desired compound 10. The reaction is conducted in a suitable solvent, and in the presence of a suitable base. Suitable solvents include, but are not limited to, halogenated solvents such as chloroform, dichloroethane and dichloromethane, aprotic solvents such as DMF, DMSO, THF, acetonitrile, pyridine, toluene, or combinations thereof. Suitable bases include, but are not limited to, triethylamine, diisopropylethylamine, pyridine, potassium carbonate, sodium carbonate or sodium hydrogen carbonate. The reaction is conducted at a temperature effective to facilitate a reaction. In some embodiments, the effective temperature is from greater than 20° C. to greater than 120° C., such as from about 50° C. to about 100° C.

One exemplary embodiment of a method of making a compound having formula IV is shown in Scheme 3. A person of ordinary skill in the art will appreciate that other suitable methods for making compounds having formula IV can be determined.

Scheme 3

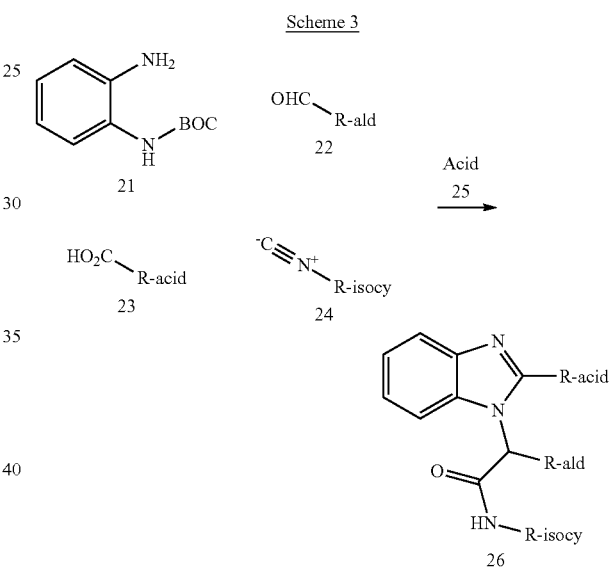

With reference to Scheme 3, a protected diamine 21, such as a BOC-protected diamine, is reacted with an aldehyde 22 in a suitable solvent for from about 10 minutes to greater than 60 minutes, such as from about 20 minutes to about 40 minutes. Suitable solvents include, but are not limited to, alcohols, such as methanol or ethanol, water or polar, aprotic solvents such as DMF or DMSO, or combinations thereof. Acid 23 and isocyanide 24 are then added. After an amount of time effective to allow the reaction to proceed, the resulting product is deprotected, such as by adding a suitable acid 25 for removing the BOC protecting group. The effective amount of time is from about 30 minutes to greater than 12 hours, such as from about 1 hour to about 4 hours. Suitable acids are those known to a person of ordinary skill in the art to remove the protecting group, and include, but are not limited to, hydrochloric acid and trifluoroacetic acid. After the addition of the acid, the reaction mixture is left for an amount of time effective to facilitate a reaction to form compound 26, such as from about 6 hours to greater than 24 hours, such as from about 12 hours to about 20 hours.

Typically, the reaction mixture is agitated, such as by stirring or shaking, for at least some of the reaction time, and in some embodiments, for substantially all of the reaction time. The reaction is conducted at a temperature effective to facilitate a reaction, such as from about 10° C. to greater than about 50° C., typically from about 20° C. to about 40° C.

Another exemplary method of making a compound having formula IV is shown in Scheme 4. The method is a modification of the method disclosed in WO2004087714, which is incorporated herein in its entirety.

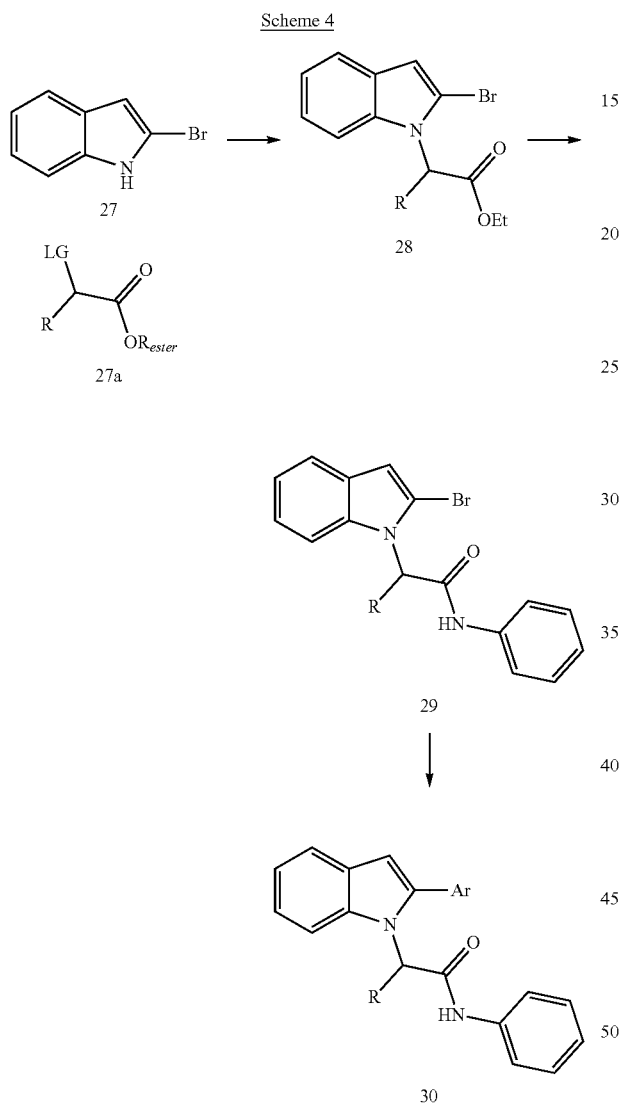

With reference to Scheme 4, a haloindole 27, such as a bromo indole, is reacted with an ester compound 27a, which comprises a desired R group and a leaving group LG, to form compound 28. The leaving group can be any suitable leaving group, such as a halide, triflate, mesalate or tosylate. The reaction is performed in the presence of a base, such as sodium hydride, and in a suitable solvent, such as DMF or THF.

Compound 28 is typically saponified to an acid (not shown) by any suitable method known to a person of ordinary skill in the art, such as by reacting the acid with a hydroxide base, or by treatment with an aqueous acid, such as hydrochloric acid. The acid is then typically activated, such as by forming an acid chloride, and then reacted with aniline to form compound 29. The reaction is conducted in a suitable solvent, and in the presence of a suitable base. Suitable solvents include, but are not limited to, halogenated solvents such as chloroform, dichloroethane and dichloromethane, aprotic solvents such as DMF, DMSO, THF, acetonitrile, pyridine, toluene, or combinations thereof. Suitable bases include, but are not limited to, triethylamine, diisopropylethylamine, pyridine, potassium carbonate, sodium carbonate or sodium hydrogen carbonate. The reaction is conducted at a temperature effective to facilitate a reaction. In some embodiments, the effective temperature is from greater than 20° C. to greater than 120° C., such as from about 50° C. to about 100° C.

Compound 29 is then reacted with a boronic acid (not shown) in a Suzuki-type coupling to form compound 30. In some embodiments, the boronic acid is an aromatic boronic acid. In some embodiments, the coupling is performed in the presence of a catalyst effective to facilitate the coupling reaction, and optionally in the presence of one or more additional compounds. Typical catalysts for a Suzuki coupling are palladium or nickel catalysts, including but not limited to, $NiCl_2(dppf)$, $NiCl_2(dppp)$, $Pd(PPh_3)_4$, $Pd(OAC)_2$ or $PdCl_2(PPh_3)_4$. Typical additional compounds include, but are not limited to, triphenylphosphine ($PPh_3$), and/or bases such as potassium carbonate, sodium carbonate, cesium carbonate, sodium hydroxide, potassium hydroxide, triethylamine, sodium ethoxide, sodium methoxide, tripotassium phosphate or any combination thereof. The coupling reaction is performed in any suitable solvent, such as DMF, ethanol, methanol, isopropanol, propanol, benzene, toluene, THF, dioxane, water or any combination thereof.

One exemplary embodiment of a method of making a compound having formula VII is shown in Scheme 5. A person of ordinary skill in the art will appreciate that other suitable methods for making compounds having formula VII can be determined.

Scheme 5

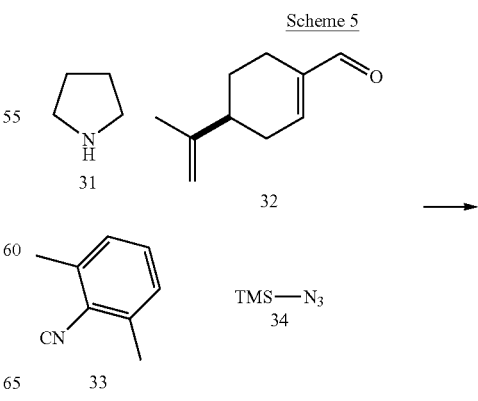

-continued

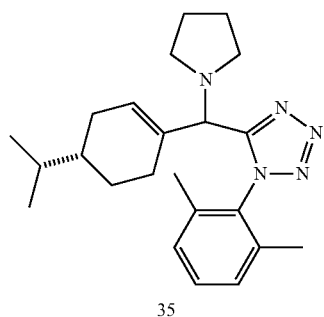
35

With reference to Scheme 5, an amine 31 is reacted with an aldehyde 32. The reaction typically is conducted in a suitable solvent, such as an alcohol, such as methanol or ethanol, water, or polar, aprotic solvents such as DMF or DMSO, or combinations thereof, for from about 10 minutes to greater than 60 minutes, such as from about 20 minutes to about 40 minutes. An isocyanide 33 and a suitable azide 34 are then added, and the reaction mixture is left for an amount of time effective to facilitate a reaction to form compound 35, such as from about 6 hours to greater than 48 hours, such as from about 12 hours to about 24 hours. One possible suitable azide is trimethylsilyl azide.

Without being bound to any particular theory, Scheme 6 provides one possible reaction mechanism for the reaction described in Scheme 5.

Scheme 6

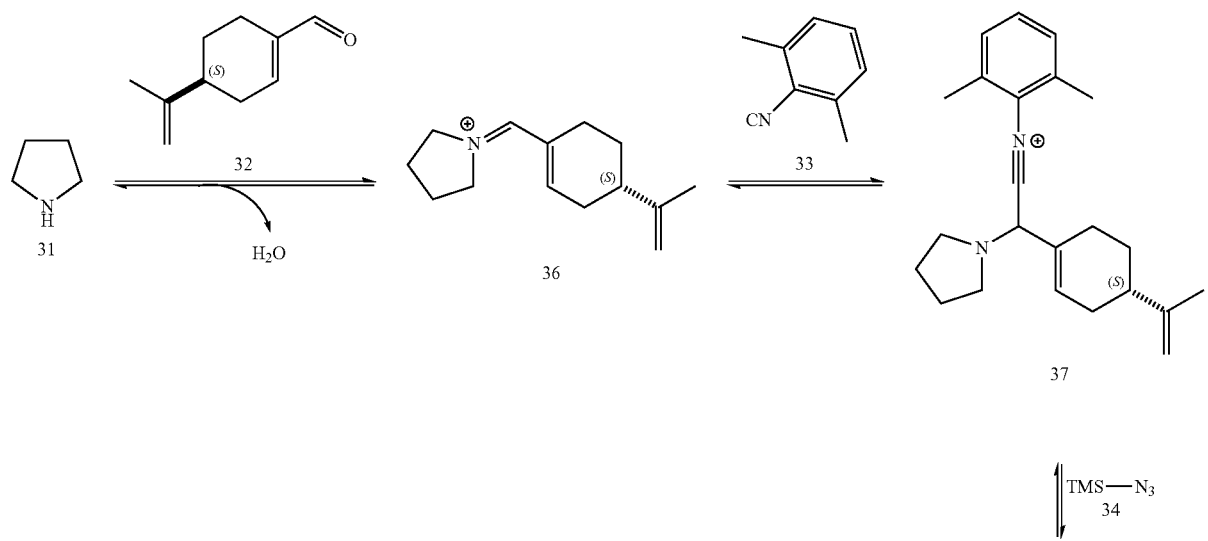

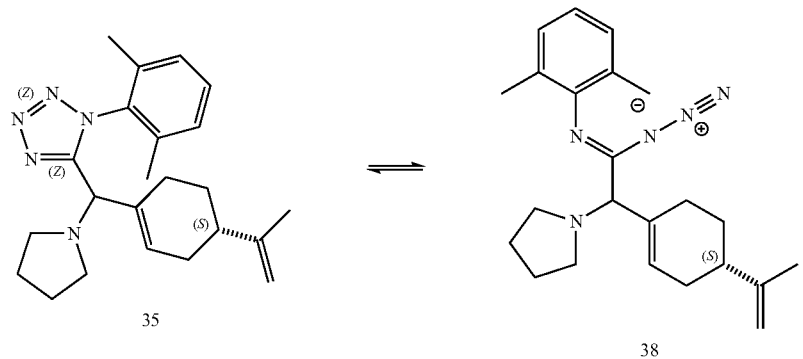

With reference to Scheme 6, the amine 31 reacts with the aldehyde 32 with the loss of water, to form an imine 36. The imine 36 then reacts with the isocyanide 33 to form an intermediate 37, which then reacts with the azide compound 34, to form an intermediate 38. The intermediate 38 then cyclizes to form the desired compound 35.

Another exemplary embodiment of a method of making a compound having formula VII is shown in Scheme 7. The method is a modification of the method disclosed by Chen, et al. Synthesis, 2010, No. 9, 1505-1511, which is incorporated herein in its entirety.

Scheme 7

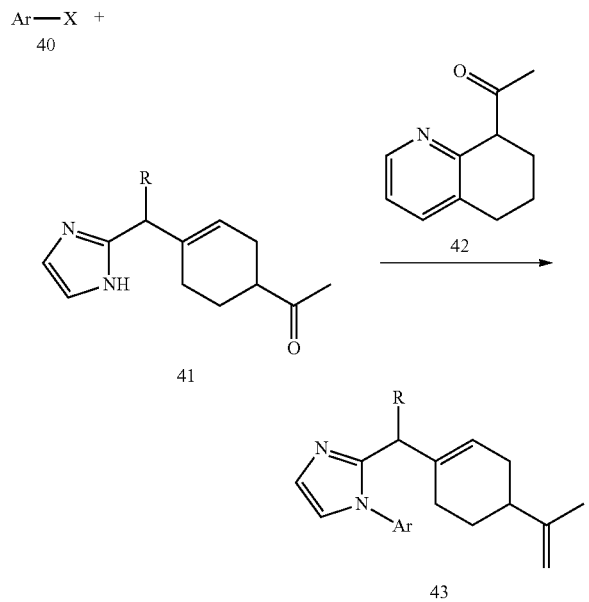

With reference to Scheme 7, an aromatic halide compound 40 is reacted with an imidazole compound 41 in the presence of a copper catalyst, such as copper (I) bromide and an additional compound 42. The reaction is performed in a suitable solvent and in the presence of a suitable base. Suitable solvents include aprotic solvents such as DMSO or DMF. Suitable bases include any base that will facilitate the reaction, such as sodium carbonate, potassium carbonate, lithium carbonate or cesium carbonate. The reaction is conducted at a temperature effective to facilitate a reaction. In some embodiments, the effective temperature is from greater than 20° C. to greater than 120° C., such as from about 50° C. to about 80° C.

VI. Methods of Using the Compounds/Compositions

Orally delivered fexaramine (Fex) (Downes et al., *Mol Cell* 11: 1079-1092, 2003) is poorly absorbed, resulting in intestinally-restricted FXR activation. It is shown herein that despite this restricted activation, Fex treatment of diet-induced obesity (DIO) mice produces a novel metabolic profile that includes reduced weight gain, decreased inflammation, browning of white adipose tissue and increased insulin sensitization. The beneficial systemic efficacy achieved with Fex suggests intestinal FXR therapy as a potentially safer approach in the treatment of insulin resistance and metabolic syndrome.

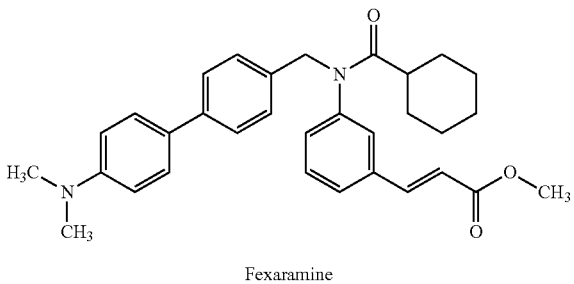

Fexaramine

It is shown herein that the gut-biased FXR agonist fexaramine has profound metabolic benefits in a mouse model of obesity. Fex protects against diet-induced weight gain by promoting the expression of genes involved in thermogenesis, mitochondrial biogenesis, and fatty acid oxidation. Linked to the unexpected browning of white adipose, Fex lowers inflammatory cytokine levels while up-regulating β-adrenergic signaling. These changes appear to be mediated in part by a change in bile acid levels and composition. In addition, intestinal-specific FXR activation corrected numerous obesity-related defects, enhanced glucose tolerance, and lowered hepatic glucose production. Notably, these physiologic changes are dependent on FXR expression and result in hepatic insulin sensitization and BAT activation, properties not formerly associated with this class of drug.

The initial event triggering systemic metabolic activation is likely coordinated by FGF15, a key regulator of energy expenditure reported to increase metabolic rate, and improve glucose and lipid homeostasis without significant changes in food intake (Fu et al., *Endocrinology* 145:2594-2603, 2004; Bhatnagar et al., *J Biol Chem* 284:10023-10033, 2009). The absence of a change in food intake is significant as failure of appetite control is a major reason for weight gain (Foster-Schubert & Cummings, *Endocr Rev* 27:779-793, 2006). Thus, systemic increases in energy expenditure, as seen in Fex-treated mice, may offer a viable alternative for obesity treatments. However, this explanation alone is not sufficient as systemic FXR agonists, while robustly inducing FGF15, do not display many of the benefits of gut-biased FXR activation.

One major difference between gut-biased and systemic FXR activation is the impact on serum bile acids, which for Fex includes a marked change in the relative composition of circulating BAs. A reduction in hepatic CYP7A1 accompanied by an increase in CYP7B1 expression shifts BA synthesis away from cholic acid towards chenodeoxycholic acid derivatives, most notably lithocholic acid. While the absolute amount of lithocholic acid did not change following Fex the relative amount increased dramatically. Lithocholic acid is a hydrophobic secondary bile acid and the most potent endogenous ligand for the G protein-coupled bile acid receptor TGR5 (Ullmer et al., *Br. J. Pharmacol.* 169:671-684, 2013). Interestingly, Fex treatment induces metabolic changes similar to those observed with systemic administration of a synthetic TGR5 agonist (Ullmer et al., *Br. J. Pharmacol.* 169:671-684, 2013). Also, induction of DIO2, a downstream target of TGR5 (Watanabe et al., *Nature* 439: 484-489, 2006), in BAT with oral Fex implicates this pathway in the observed increased energy expenditure. Indeed, the metabolic improvements attributed to Fex treatment were tempered in TGR5$^{-/-}$ mice, indicating that TGR5 activation is important in meditating some of the actions of Fex. Furthermore, the coordinate "browning" of the WAT depot provides an independent yet complementary contribution to increased thermogenic capacity.

These results uncover a new therapeutic avenue to manipulate energy expenditure without appetite changes through intestinally-biased activation of the nuclear receptor FXR. While contrary indications have been recently reported, the integral role of FXR in gut homeostasis confounds these studies (Kim et al., *J Lipid Res* 48:2664-2672, 2007; Li, et al., *Nat Commun* 4:2384, 2013). Gut-restricted drugs such as Fex inherently offer improved safety profiles, achieving systemic efficacy while avoiding systemic toxicity. In support of the remarkable metabolic improvements achieved via oral Fex treatment, intestinal FXR has been recently identified as a molecular target of vertical sleeve gastrectomy (Ryan et al., *Nature* 509:183-188, 2014), indicating that Fex may offer a non-surgical alternative for the control of metabolic disease.

A. Treatment or Prevention of Metabolic Disorders

Treatment of subjects, including diet-induced obesity (DIO) subjects, with one or more of the disclosed FXR agonists (such as two or more, three or more, four or more, or five or more of the disclosed FXR agonists, such as 2, 3, 4, or 5 of the disclosed FXR agonists) may produce beneficial body-wide metabolic effects such as reduced weight gain, decreased inflammation, browning of white adipose tissue, activation of BAT, improved insulin sensitization, or combinations thereof. Thus, intestinally-restricted FXR administration is superior to systemic FXR therapy for body-wide metabolic disorders including obesity and metabolic syndrome. One or more of the FXR agonists disclosed herein may be administered to a gastrointestinal (GI) tract of the subject to activate FXR receptors in the intestines, and thereby treat or prevent a metabolic disorder in the subject. Thus, the FXR agonist(s) can be administered to, without limitation, the mouth (such as by injection or by ingestion by the subject), the esophagus, the stomach or the intestines themselves.

Orally delivered, these agonists may in some examples be ineffectively absorbed, resulting in intestinally-restricted FXR activation. In some embodiments, FXR activation is completely limited to the intestine. In some embodiments, administration of one or more of the disclosed agonists does not result in significant activation in the liver or kidney. In other embodiments, some measurable extra-intestinal FXR activation occurs, however the FXR activation is considerably greater in the intestines than in other locations in the body, such as in the liver or kidney. In some embodiments, the FXR agonist is minimally absorbed. In some embodiments, the FXR agonist is directly administered to the intestines (such as to the distal ileum) of an individual in need thereof. In some embodiments, the FXR agonist is directly administered to the colon or the rectum of an individual in need thereof. In some embodiments, the FXR agonist is administered orally, and less than 50%, less than 40%, less than 30%, less than 20%, less than 10%, less than 9%, less than 8%, less than 7%, less than 6%, less than 5%, less than 4%, less than 3%, less than 2%, or less than 1% of the FXR agonist is systemically absorbed.

In some examples, the subject to be treated is one who is diabetic (for example has type II diabetes), is hyperglycemic, and/or is insulin resistant. In some examples, the subject is obese, for example has a body mass index (BMI) of 25 of higher, 30 or greater, 35 or greater, 40 or greater, such as a BMI of 25 to 29, 30 to 34, or 35 to 40.

In some examples, the disclosed methods may reduce weight gain in a subject (such as a human), such as diet-induced weight gain. In some examples, such methods reduce weight gain in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies. Similarly, in some examples, the disclosed methods reduce the BMI of a subject (such as a human). In some examples, such methods reduce the BMI of a subject by at least 5%, at least 10%, at least 15%, at least 20%, or at least 30% (such as 5% to 30%, 5% to 25%, 10% to 20%, or 10% to 30%), for example relative to a subject not treated with the disclosed therapies.

In some examples, the disclosed methods may increase browning of white adipose tissue in a subject (such as a human). In some examples, such methods increase browning of white adipose tissue in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

In some embodiments, the method may reduce or prevent diet-induced weight gain, for example in a mammalian subject, such as a human. In some embodiments, the one or more FXR agonists are administered to an obese subject whose obesity is diet-related (i.e., diet-induced obesity). In other embodiments, the one or more FXR agonists can be administered to an obese subject whose obesity is not diet-related (such as an individual with familial/genetic obesity or obesity resulting from medication use). In other embodiments, the one or more FXR agonists can be administered to a subject who is overweight (but not obese) or a subject that is neither overweight nor obese. Thus, in some embodiments, the one or more FXR agonists can be used to prevent obesity from developing. In some embodiments, the targeting of the therapy to the intestines reduces the chance of side effects which can result from systemic action, thus improving the safety profile of the therapy.

In some embodiments, the one or more FXR agonists are administered to an obese or non-obese subject for a metabolic disorder or condition other than obesity or weight gain. In certain embodiments, the metabolic disorder is insulin resistance, including non-insulin-dependent diabetes mellitus (NIDDM) (i.e., type II diabetes). The administration of the one or more FXR agonists can result in increased insulin sensitivity to insulin in the liver, leading to increased uptake of glucose into hepatic cells. In certain embodiments, the metabolic disorder is dyslipidemia, including hyperlipidemia (elevated LDL, VLDL or triglycerides) or low HDL levels. Thus, in certain embodiments, administration of one or more FXR agonists can result in improved glucose and/or lipid homeostasis in the subject. In some embodiments, administration of the one or more FXR agonists results in a decrease in the amount of serum lipids and/or triglycerides, decrease liver free fatty acids, decrease liver cholesterol, increase liver glycogen, decrease muscle free fatty acids, decrease muscle cholesterol, or combinations thereof, in the subject. Thus, in some examples, the disclosed methods decrease the amount of serum lipids and/or triglycerides in a subject (such as a human). In some examples, such methods decrease serum lipids and/or triglycerides in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to levels observed in a subject not treated with the disclosed therapies. In some examples, such methods decrease liver free fatty acids in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to levels observed in a subject not treated with the disclosed therapies. In some examples, such methods decrease liver cholesterol in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to levels observed in a subject not treated with the disclosed therapies. In some examples, such methods increase liver glycogen in the subject by at least 5%, at least 10%, at least 15%, at least 20%, at least 30%, at least 50%, at least 75%, at least 90%, at least 100%, or at least 200% (such as 5% to 50%, 5% to 25%, 100% to 200%, 10% to 100%, or 10% to 200%), for example relative to levels observed in a subject not treated with the disclosed therapies. In some examples, such methods decrease muscle free fatty acids in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to levels observed in a subject not treated with the disclosed therapies. In some examples, such methods decrease muscle cholesterol in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to levels observed in a subject not treated with the disclosed therapies. In some examples, the disclosed embodiments may increase insulin sensitivity to insulin in the liver of a subject (such as a human). In some examples, such methods increase insulin sensitivity to insulin in the liver of the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

In some embodiments, administration of the one or more FXR agonists results in no substantial change in food intake and/or fat consumption in the subject. In other embodiments, food intake and/or fat consumption is reduced minimally, such as by less than 15%, less than 10%, or less than 5%. In some embodiments, no substantial change in appetite in the subject results. In other embodiments, reduction in appetite is minimal as reported by the subject.

In some embodiments, administration of the one or more FXR agonists results in an increase in the metabolic rate in the subject. Thus, in some examples, the disclosed methods may increase the metabolic rate in a subject (such as a human). In some examples, such methods increase the metabolic rate in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to a subject not treated with the disclosed therapies.

In some embodiments, this increase in metabolism results from enhanced oxidative phosphorylation in the subject, which in turn can lead to increased energy expenditure in tissues (such as BAT). Thus, in some examples, the disclosed methods may increase BAT activity in a subject (such as a human). In some examples, such methods increase BAT activity in a subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to a subject not treated with the disclosed therapies.

In some embodiments, administration of the one or more FXR agonists results in a decrease in the amount of serum insulin in the subject. Thus, in some examples, the disclosed methods decrease the amount of serum insulin in a subject (such as a human) In some examples, such methods decrease serum insulin in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to levels observed in a subject not treated with the disclosed therapies.

In some embodiments, administration of the one or more FXR agonists results in a decrease in the amount of serum glucose in the subject. Thus, in some examples, the disclosed methods decrease the amount of serum glucose in a subject (such as a human). In some examples, such methods decrease serum glucose in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to levels observed in a subject not treated with the disclosed therapies. Embodiments of a method are provided for lowering elevations in blood glucose resulting from food intake in a subject. Thus, in some examples, such methods decrease blood glucose in a subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to a subject not treated with the disclosed therapies. Such methods can include orally administering to the subject a therapeutically effective amount of one of the disclosed minimally absorbed FXR agonists. In some embodiments, a method for lowering elevated body weight in a subject is provided, wherein the method includes orally administering to said subject a therapeutically effective amount of one of the disclosed minimally absorbed FXR agonists. Thus, in some examples, such methods decrease the body weight of a subject by at least 5%, at least 10%, at least 15%, at least 20%, at least 30%, or at least 50% (such as 5% to 50%, 5% to 25%, 5% to 20%, 10% to 20%, 10% to 70%, or 10% to 30%), for example relative to a subject not treated with the disclosed therapies. In some embodiments, the elevated body weight and/or elevated glucose levels resulted from a particular pattern of food intake, such as a high fat diet and/or a high calorie diet.

In some embodiments, the one or more FXR agonists are co-administered with one or more additional compounds or therapies, for treatment or prevention of a metabolic disorder. For example, one or more FXR agonists can be administered with an insulin sensitizing drug, an insulin secretagogue, an alpha-glucosidase inhibitor, a glucagon-like peptide (GLP) agonist, a DPP-4 inhibitor (such as sitagliptin, vildagliptin, saxagliptin, linagliptin, anagliptin, teneligliptin, alogliptin, gemigliptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as ioglitazone, rosiglitazone, rivoglitazone, or troglitazone], aleglitazar, farglitazar, muraglitazar, or tesaglitazar), or a combination thereof. Likewise, one or more FXR agonists can be administered with a statin, HMG-CoA reductase inhibitor, fish oil, fibrate, niacin or other treatment for dyslipidemia. In some embodiments, provided herein is a method for treating a metabolic disorder in a subject, such as lowering elevated body weight and/or lowering elevated blood glucose from food intake, comprising orally co-administering to said subject a therapeutically effective amount of a disclosed minimally absorbed FXR agonist and retinoic acid. 9 cis-retinoic acid is the ligand for retinoic acid receptor (RXR), the heterodimeric partner of FXR. In some examples, the method includes also administering nicotinamide ribonucleoside and/or an analog of nicotinamide ribonucleoside (such as those that promote NAD+ production of which is a substrate for many enzymatic reactions such as p450s which are a target of FXR, for example see Yang et al., *J. Med Chem.* 50:6458-61, 2007, herein incorporated by reference).

Glucagon-like peptide-1 (GLP-1) is an incretin derived from the transcription product of the proglucagon gene. The major source of GLP-1 in the body is the intestinal L cell that secretes GLP-1 as a gut hormone. The biologically active forms of GLP-1 include GLP-1-(7-37) and GLP-1-(7-36) $NH_2$ (HAEGTFTSDVSSYLEGQAAKEFIAWLVKGR; SEQ ID NO: 1), which result from selective cleavage of the proglucagon molecule. GLP-2 is a 33 amino acid peptide (HADGSFSDEMNTILDNLAARDFINWLIQTKITD; SEQ ID NO: 2) in humans. GLP-2 is created by specific post-translational proteolytic cleavage of proglucagon in a process that also liberates GLP-1. GLP agonists are a class of drugs ("incretin mimetics") that can be used to treattype 2 diabetes. Examples include, but are not limited to: exenatide (Byetta/Bydureon), liraglutide (Victoza), lixisenatide (Lyxumia), and albiglutide (Tanzeum).

In certain embodiments, the FXR agonist enhances the secretion of glucagon-like peptide-1 (GLP-1) and/or glucagon-like peptide-2 (GLP-2). In some embodiments, the FXR agonist enhances the secretion of a pancreatic polypeptide-fold such as peptide YY (PYY). In certain embodiments, the FXR agonist enhances the activity of FGF15 or FGF19. In certain embodiments, the FXR agonist enhances secretion of an enteroendocrine peptide and/or is administered in combination with an agent that enhances secretion or activity of an enteroendocrine peptide. Thus, in some examples, the disclosed methods may increase the secretion of one or more of GLP-1, GLP-2, and PYY in a subject (such as a human). In some examples, such methods increase the secretion of one or more of GLP-1, GLP-2, and PYY in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to a subject not treated with the disclosed therapies. Furthermore, in some examples, the disclosed methods increase the secretion of one or more of GLP-1, GLP-2, and PYY in a subject (such as a human) In some examples, such methods increase the activity of one or more of FGF15 and FGF19 in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to a subject not treated with the disclosed therapies.

The gut-biased FXR agonists disclosed herein can have profound metabolic benefits with respect to obesity. The gut-biased FXR agonists can protect against diet-induced weight gain by, for example, promoting the expression of genes involved in thermogenesis, mitochondrial biogenesis, and/or fatty acid oxidation. In some embodiments, linked to the unexpected browning of white adipose, the disclosed gut-biased FXR agonists can lower inflammatory cytokine levels while up-regulating β-adrenergic signaling. These changes can be mediated, at least in part, by a change in bile acid levels and composition. In various embodiments, a prandial activation of intestinal FXR is triggered by administering to a subject one of the FXR agonists disclosed herein, such as synthetic FXR agonist fexaramine (Fex). The intestinal-specific FXR activation disclosed herein can be utilized to enhance glucose tolerance and lower hepatic glucose production. Thus, in some examples, such methods may decrease hepatic glucose production in a subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to a subject not treated with the disclosed therapies. These physiologic changes can result in hepatic insulin sensitization and/or BAT activation—properties not previously associated with FXR agonists.

In contrast to the effects of system-wide drugs (including systemic FXR agonists), selective activation of intestinal FXR as disclosed herein can mimic the restricted bile acid response linked to feeding. The FXR agonists disclosed herein may be gut-specific and robustly induce enteral FGF15, leading to alterations in bile acid composition without activating hepatic FXR target genes. Unlike systemic drugs, these gut-specific FXR agonists may protect against diet-induced weight gain, reduce body-wide inflammation, enhance thermogenesis, promote browning of white adipose tissue, promote activation of BAT, and suppress hepatic glucose production.

In some embodiments, the initial event triggering systemic metabolic activation is coordinated by FGF15 (the mouse equivalent of human FGF19) or FGF19. In an embodiment, administration of the FXR agonist results in activation of FGF15 or FGF19 (such as an increase in FGF15 or FGF19 activity of at least 25%, at least 50%, at least 75%, at least 90%, or at least 95%, relative to no treatment with an FXR agonist), which in turn can regulate energy expenditure, such as by increasing metabolic rate, improving glucose homeostasis (such as by improving insulin sensitivity), and/or improving lipid homeostasis without requiring significant changes in food intake. The absence of a required or resulting change in food intake can be expected to increase effectiveness, as failure of appetite control is a major reason for weight gain and difficulty in losing weight. Thus, systemic increases in energy expenditure, as seen in Fex-treated mice, can form the basis for an obesity treatment.

In some embodiments, treatment with one or more of the disclosed FXR agonists can produce a change in the bile acid pool, such as a dramatic increase in the level of deoxycholic acid (such as an increase of at least 25%, at least 50%, at least 75%, at least 90%, or at least 100%, relative to no treatment with an FXR agonist), a potent ligand for the G protein-coupled bile acid receptor TGR5. Fex treatment was observed to induce D102, a downstream target of TGR5, in brown adipose tissue (BAT), thus implicating this additional pathway in the observed increase in energy expenditure. Furthermore, the coordinate "browning" of white adipose tissue provides an independent yet complementary contribution to increased thermogenic capacity.

Thus, a new therapeutic avenue exists to manipulate energy expenditure without appetite changes through intestinally-biased activation of the nuclear receptor FXR. Furthermore, gut-restricted FXR agonists such as Fex can offer improved safety profiles with limited circulation in the serum, thus reducing the risks of off-target effects and toxicity. The remarkable metabolic improvements achieved with Fex treatment provide a new role for intestinal targeting in the control of metabolic disease.

B. Treatment or Prevention of Inflammation

Also provided herein are embodiments of a method for treating or preventing an inflammatory intestinal condition. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists).

Thus, in some examples, the disclosed embodiments may reduce inflammation in a subject (such as a human), such as inflammation in the intestine. In some examples, such embodiments may reduce inflammation (such as intestinal inflammation) in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

In various embodiments, the inflammatory condition can be necrotizing enterocolitis (NEC), gastritis, ulcerative colitis, inflammatory bowel disease, irritable bowel syndrome, pseudomembranous colitis, gastroenteritis, radiation induced enteritis, chemotherapy induced enteritis, gastroesophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection. In some embodiments, the inflammatory condition is NEC and the subject is a newborn or prematurely born infant. In some embodiments, the subject is enterally-fed infant or formula-fed infant.

In some embodiments, the one or more FXR agonists are co-administered with one or more additional compounds or therapies, for treatment or prevention of an inflammatory intestinal condition. In some embodiments, the one or more FXR agonists are co-administered with an oral corticosteroid and/or other anti-inflammatory or immuno-modulatory therapy. In some embodiments, the FXR agonist can be administered to the subject in conjunction with one or more antibiotics (e.g., metronidazole, vancomycin, and/or fidaxomicin) to treat or prevent the inflammatory condition. In some embodiments, the FXR agonist can be administered to the subject in conjunction with or following antibiotic therapy to treat or prevent pseudomembranous colitis associated with bacterial overgrowth (such as *C. dificile* overgrowth) in the subject. In some embodiments, the FXR agonist can be administered to the subject in conjunction with metronidazole or other indicated therapy to treat inflammation associated with bacterial overgrowth in an intestinal area. In some embodiments, the FXR agonist can be administered to the subject in conjunction with the ingestion of foods or other substances predicted to induce inflammation in the gastro-intestinal system of the subject (such as in a subject with celiac disease). In some examples, the method includes also administering nicotinamide ribonucleoside and/or an analog of nicotinamide ribonucleoside (such as those that promote NAD+ production of which is a substrate for many enzymatic reactions such as p450s which are a target of FXR, for example see Yang et al., *J. Med Chem.* 50:6458-61, 2007, herein incorporated by reference).

C. Prevention and/or Treatment of Cell Proliferation Diseases

Disclosed herein are embodiments of a method for preventing and/or treating cell proliferation diseases, such as certain types of cancer. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists).

In some embodiments, the compounds disclosed herein may be used in the prevention or treatment of adenocarcinomas, i.e. carcinoma derived from glandular tissue or in which the tumor cells form recognizable glandular structures. Adenocarcinomas can be classified according to the predominant pattern of cell arrangement, as papillary, alveolar, etc., or according to a particular product of the cells, as mucinous adenocarcinoma. Adenocarcinomas arise in several tissues, including the colon, kidney, breast, cervix, esophagus, gastric, pancreas, prostate and lung.

In certain embodiments, the compounds disclosed herein may be used in the prevention or treatment of a cancer of the intestine, such as colon cancer, i.e. cancer that forms in the tissues of the colon (the longest part of the large intestine), or a cancer of another part of the intestine, such as the jejunum, and/or ileum. Colon cancer is also referred to as "colorectal cancer." Most colon cancers are adenocarcinomas (cancers that begin in cells that may line internal organs and have gland-like properties). Cancer progression is characterized by stages, or the extent of cancer in the body. Staging is usually based on the size of the tumor, whether lymph nodes contain cancer, and whether the cancer has spread from the original site to other parts of the body. Stages of colon cancer include stage I, stage II, stage III and stage IV. In some embodiments herein, the colon adenocarcinoma is from any stage. In other embodiments, the colon adenocarcinoma is a stage I cancer, a stage II cancer or a stage III cancer.

Thus, in some examples, the disclosed embodiments reduce tumor burden in a subject (such as a human). In some examples, disclosed embodiments reduce tumor burden (such as colon tumor burden) in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments reduce tumor size and/or volume in a subject (such as a human) In some examples, disclosed embodiments reduce tumor size and/or volume (such as a colon tumor) in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments reduce effects of cachexia due to a tumor in a subject (such as a human). In some examples, disclosed embodiments reduce effects of cachexia (such as due to a colon tumor) in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments increase survival rates of a subject (such as a human) with a tumor. In some examples, disclosed embodiments increase survival rates of a subject (such as a human) with a tumor (such as a colon cancer) in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

In some embodiments, the compounds disclosed herein may be administered in combination with one or more additional anticancer therapies (such as a biologic [e.g., antibody, for example bevacizumab, cetuximab, or panitumumab], chemotherapeutic, or radiologic, for example FOLFOX, FOLFIRI, CapeOX, 5-FU, leucovorin, regorafenib, irinotecan, and oxaliplatin), to prevent or treat a cell proliferation disease. In some examples, the method includes also administering nicotinamide ribonucleoside and/or an analog of nicotinamide ribonucleoside (such as those that promote NAD+ production of which is a substrate for many enzymatic reactions such as p450s which are a target of FXR, for example see Yang et al., *J. Med Chem.* 50:6458-61, 2007, herein incorporated by reference).

D. Prevention and/or Treatment of Alcoholic and Non-Alcoholic Liver Disease

Disclosed herein are embodiments of a method for preventing and/or treating alcoholic or non-alcoholic liver diseases, such as steatosis, cirrhosis, alcoholic hepatitis, NASH and NAFLD. In some embodiments, the compounds disclosed herein may be used in the prevention or treatment of alcoholic liver diseases. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists).

Thus, in some examples, the disclosed embodiments reduce fatty liver (steatosis) in a subject (such as a human). In some examples, disclosed embodiments reduce steatosis in the subject (such as in an alcoholic) by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments reduce cirrhosis in a subject (such as a human). In some examples, disclosed embodiments reduce cirrhosis in the subject (such as in an alcoholic) by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies. Thus the disclosed embodiments can reduce liver inflammation and/or fibrosis, for example by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments reduce alcoholic hepatitis in a subject (such as a human). In some examples, disclosed embodiments reduce alcoholic hepatitis in the subject (such as in an alcoholic) by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies. Thus the disclosed embodiments can reduce inflammation of hepatocytes, for example by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments reduce liver enzymes in a subject (such as a human). In some examples, disclosed embodiments reduce liver enzymes (e.g., serum ALT and/or AST levels) in the subject (such as in an alcoholic) by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments reduce liver triglycerides in a subject (such as a human). In some examples, disclosed embodiments reduce liver triglycerides in the subject (such as in an alcoholic) by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

In some embodiments, the compounds disclosed herein may be administered in combination with one or more additional therapies for treating alcoholic or non-alcoholic liver disease (such as antioxidants, corticosteroids, and/or anti-TNF), to prevent or treat alcoholic or non-alcoholic liver disease. In one example, nicotinamide ribonucleoside and/or analogs of nicotinamide ribonucleoside that promotes NAD+ production of which is a substrate for many enzymatic reactions such as p450s which are a target of FXR (e.g., see Yang et al., *J. Med. Chem.* 50:6458-61, 2007), are also administered.

E. Prevention and/or Treatment of Other Diseases

Disclosed herein are embodiments of a method for preventing and/or treating cholestatic disorders, such primary biliary cirrhosis (PBC), primary sclerosing cholangitis (PSC), overlap syndrome (PBC plus autoimmune hepatitis), cholestasis resulting from a drug (e.g., one or more of androgen, birth control pills, gold salts, nitrofurantoin, anabolic steroids, chlorpromazine, prochlorperazine, sulindac, cimetidine, estrogen, statins, and antibiotics such as TMP/SMX, flucoxacillin and erythromycin), drug-induced cholestatic hepatitis, total parenteral nutrition (TPN)-induced cholestasis, ICU/sepsis-related cholestasis, obstetric cholestasis, graft vs. host disease, prolonged cholestasis due to hepatitis A, B or C infection, cholestasis due to cystic fibrosis, alcoholic hepatitis, progressive familial intrahepatic cholestasis (PFIC) syndromes, Alagille syndrome, biliary atresia, or any combination thereof. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists). Thus, in some examples, the disclosed embodiments increase bile flow in a subject (such as a human) by at least 5%, at least 10%, at least 15%, at least 20%, at least 30%, at least 40%, at last 50%, at least 60%, at least 70%, at least 80%, at least 90%, at least 100%, or even at least 200% (such as 5% to 50%, 5% to 25%, 50% to 75%, or 75% to 200%), for example relative to a subject not treated with the disclosed therapies.

Disclosed herein are embodiments of a method for preventing and/or treating an intestinal permeability condition, such as Crohn's disease, ulcerative colitis, infectious colitis, celiac disease, type 1 diabetes, inflammatory bowel disease, irritable bowel syndrome, or any combination thereof. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists). In some examples, disclosed embodiments reduce undesired intestinal permeability in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Disclosed herein are embodiments of a method for preventing and/or treating a disorder that causes or results from an altered intestinal microbiome, such as celiac disease, the intestinal permeability conditions described herein, the intestinal inflammation disorders described herein, alcoholic hepatitis, necrotizing enterocolitis, Crohn's disease, ulcerative colitis, intestinal lesions (such as those in a cystic fibrosis patient), cirrhosis, or any combination thereof. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists). In some examples, disclosed embodiments bring the intestinal microbiome closer to normal levels in the subject, for example within 20%, with in 10% or within 5% of normal for example relative to a subject not treated with the disclosed therapies.

Disclosed herein are embodiments of a method for treating an inborn error of metabolism, such as cerebrotendinous xanthomatosis. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists). In some examples, disclosed embodiments reduce plasma cholesterol levels in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Disclosed herein are embodiments of a method for treating a bile disorder, such as benign biliary stricture, malignant biliary obstruction, bile acid diarrhea, or any combination thereof. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists). In some examples, disclosed embodiments reduce production of bile acids in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies. In some examples, disclosed embodiments increase intestinal absorption of bile acids in the subject by at least 5%, at least 10%, at least 10%, at least 15%, at least 20%, at least 30%, at least 40%, at last 50%, at least 60%, at least 70%, at least 80%, at least 90%, at least 100%, or even at least 200% (such as 5% to 50%, 5% to 25%, 50% to 75%, or 75% to 200%), for example relative to a subject not treated with the disclosed therapies.

Disclosed herein are embodiments of a method for treating or preventing a malabsorption disorder (e.g., intestinal malabsorption), such as short bowel syndrome (or symptoms arising from such, such as diarrhea, steatorhea, malnutrition, fatigue, vitamin deficiency), environmental enteropathy, or tropical sprue. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists). In some examples, disclosed embodiments increase bowel absorption in the subject by at least 5%, at least 10%, at least 10%, at least 15%, at least 20%, at least 30%, at least 40%, at last 50%, at least 60%, at least 70%, at least 80%, at least 90%, at least 100%, or even at least 200% (such as 5% to 50%, 5% to 25%, 50% to 75%, or 75% to 200%), for example relative to a subject not treated with the disclosed therapies.

F. Administration

The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly or monthly etc.) doses over a period of a few days to months, or even years. For example, a therapeutically effective amount of one or more compounds disclosed herein can be administered in a single dose, twice daily, weekly, or in several doses, for example daily, or during a course of treatment. In a particular non-limiting example, treatment involves once daily dose or twice daily dose.

In some embodiments, the FXR agonist(s) is administered orally. In some embodiments, the FXR agonist is administered as an ileal-pH sensitive release formulation that delivers the FXR agonist to the intestines, such as to the ileum of an individual. In some embodiments, the FXR agonist is administered as an enterically coated formulation. In some embodiments, oral delivery of an FXR agonist provided herein can include formulations, as are well known in the art, to provide prolonged or sustained delivery of the drug to the gastrointestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. The intended effect is to extend the time period over which the active drug molecule is delivered to the site of action (e.g., the intestines) by manipulation of the dosage form. Thus, enteric-coated and enteric-coated controlled release formulations are within the scope of the present disclosure. Suitable enteric coatings include cellulose acetate phthalate, polyvinylacetate phthalate, hydroxypropylmethylcellulose phthalate and anionic polymers of methacrylic acid and methacrylic acid methyl ester.

In some embodiments, the FXR agonist is administered before ingestion of food, such as at least 10 minutes, at least 15 minutes, at least 20 minutes, or at least 30 minutes before ingestion of food (such as 10-60 minutes or 10-30 minutes before ingesting food). In some embodiments of the methods described herein, the FXR agonist is administered less than about 60 minutes before ingestion of food. In some embodiments of the methods described above, the FXR agonist is administered less than about 30 minutes before ingestion of food. In some embodiments of the methods described herein, the FXR agonist is administered after ingestion of food. In some embodiments, the methods further comprise administration of a DPP-IV inhibitor, a TGR5 agonist, a biguanide, an incretin mimetic, or GLP-1 or an analog thereof. In some embodiments, the methods further comprise administration of a steroid or other anti-inflammatory compound which may have an effect in the gut. In some embodiments, the methods further include co-administration of an antibiotic therapy, and the FXR agonist treats or prevents inflammation, such as inflammation associated with antibiotic-induced colitis.

The composition administered can include at least one of a spreading agent or a wetting agent. In some embodiments, the absorption inhibitor is a mucoadhesive agent (e.g., a mucoadhesive polymer). In some embodiments, the mucoadhesive agent is selected from methyl cellulose, polycarbophil, polyvinylpyrrolidone, sodium carboxymethyl cellulose, and a combination thereof. In some embodiments, a pharmaceutical composition administered further includes an enteroendocrine peptide and/or an agent that enhances secretion or activity of an enteroendocrine peptide.

The pharmaceutical compositions that comprise one or more compounds disclosed herein can be formulated in unit dosage form, suitable for individual administration of precise dosages. In one non-limiting example, a unit dosage contains from about 1 mg to about 50 g of one or more compounds disclosed herein, such as about 10 mg to about 10 g, about 100 mg to about 10 g, about 100 mg to about 1 g, about 500 mg to about 5 g, or about 500 mg to about 1 g. In other examples, a therapeutically effective amount of one or more compounds disclosed herein is from about 0.01 mg/kg to about 500 mg/kg, for example, about 0.5 mg/kg to about 500 mg/kg, about 5 mg/kg to about 250 mg/kg, or about 50 mg/kg to about 100 mg/kg. In other examples, a therapeutically effective amount of one or more compounds disclosed herein is from about 50 mg/kg to about 250 mg/kg, for example about 100 mg/kg.

VII. Working Examples

Example 1

Activity of Orally-Administered Fexaramine is Restricted to the Intestine

Figure 1A:
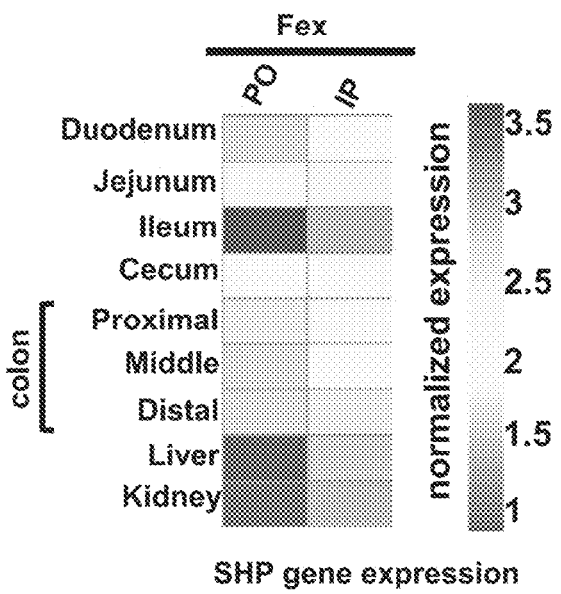
FIGS. 1A-1C are a comparative expression chart and two bar charts, respectively, illustrating increased levels of FXR target gene expression in the intestine relative to expression in the liver and kidney. 8 week-old C57BL/6J mice were treated with vehicle or fexaramine (100 mg/kg) via oral (PO) or intraperitoneal (IP) injection for three days (FIGS. 1A-1B) or five days (FIG. 1C).
Figure 1B:
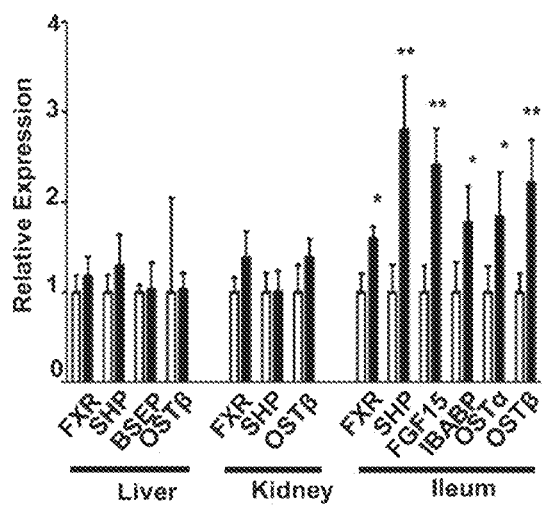
Figure 1C:
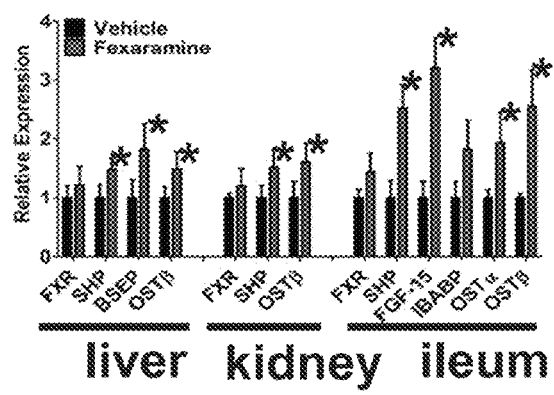
Figure 1D:
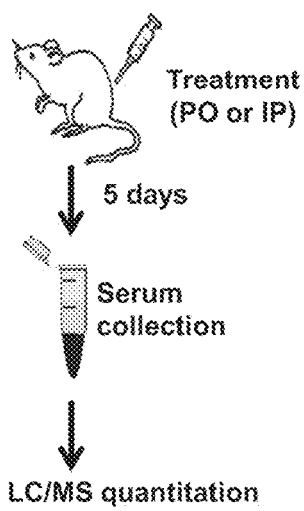
FIG. 1D is a schematic diagram illustrating an experimental procedure used to evaluate fexaramine, where mice were treated with vehicle or fexaramine (100 mg/kg) via PO or IP injection, and LC/MS quantification of serum fexaramine was conducted five days later.
Figure 1E:
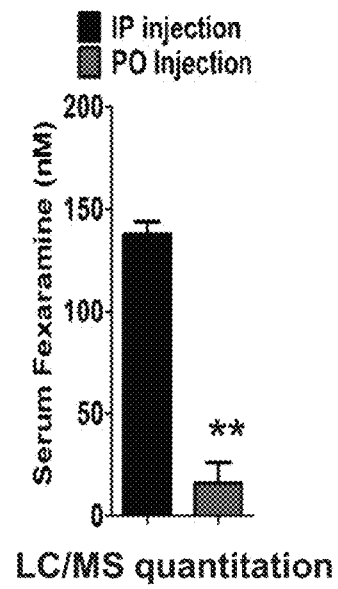
FIG. 1E is a bar chart illustrating serum fexaramine concentrations after administration as described in FIG. 1D. Data represent mean values±STD. Statistical analysis was performed with the Student's t test (*p<0.05, **p<0.01).
Figure 1F:
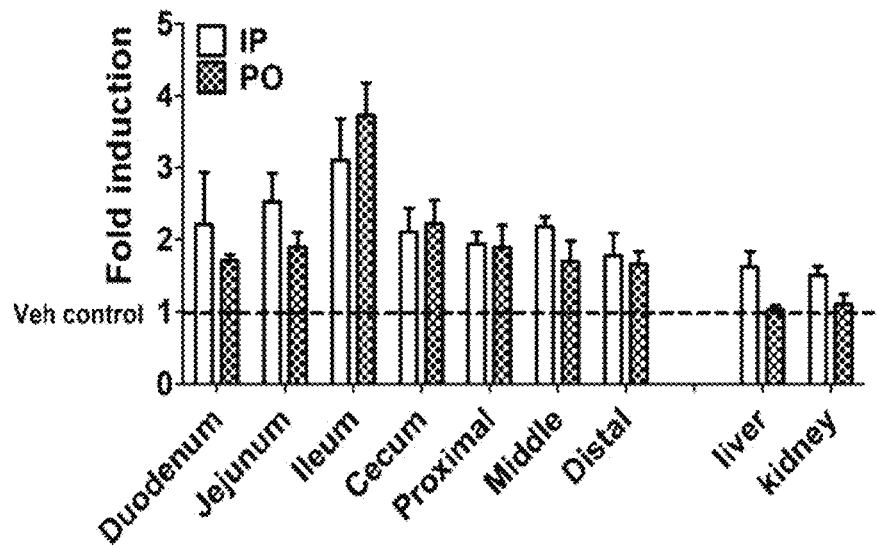
FIG. 1F is a bar chart illustrating that orally delivered fexaramine is intestinally-restricted. Mice received vehicle or Fexaramine (100 mg/kg) via per os (PO) or intraperitoneal (IP) injection for 5 days. Expression of the FXR target gene SHP after PO or IP injection in selected tissues is shown.

Upon exploration of the in vivo effects of fexaramine (Fex) administration, it was discovered that due to ineffectual absorption, oral (PO) and intraperitoneal (IP) drug delivery produced very different effects (FIGS. 1D and 1E). While robust induction of the FXR target gene SHP was seen throughout the intestine with both acute PO and IP Fex treatment (100 mg/kg for five days), induction of SHP was only seen in liver and kidney after IP treatment (FIG. 1A). Consistent with this notion, PO Fex treatment induced multiple FXR target genes in the intestine including IBABP, OST$\alpha$ and FGF15, but failed to affect the expression of these genes in liver or kidney (FIGS. 1B, 1C, and 1F). Quantification of serum Fex levels revealed an order of magnitude lower drug levels after acute PO-compared to IP-treatment (~10% of IP levels) (FIGS. 1D and 1E). Notably, the serum levels of Fex after PO administration were below the 25 nM $EC_{50}$ of Fex, consistent with the lack of target gene activation in the kidney and liver.

Example 2

Fexaramine Prevents Diet-Induced Obesity Weight Gain

To investigate the physiological effects of intestinal FXR activation by fexaramine, mice were subjected to chronic fexaramine (100 mg/kg Fex) PO treatment for 5 weeks. Chronically treated chow-fed mice were indistinguishable from vehicle-treated mice in terms of weight gain, basal metabolic activity and glucose tolerance (FIGS. 3A-3D).

Figure 2E:
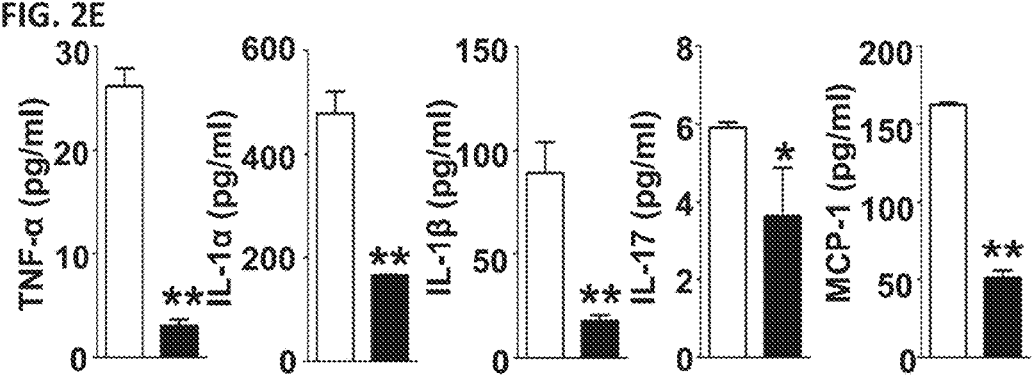
Figure 4A:
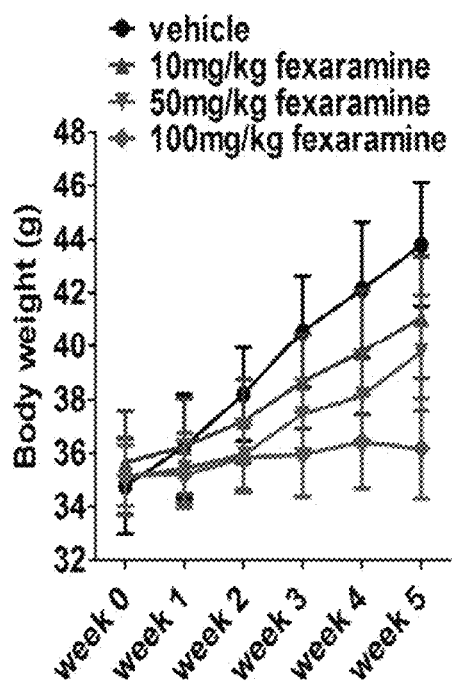
FIG. 4A is a line graph showing the effects of fexaramine at various dosage levels on the body weight of mice fed a HFD for 14 weeks and then administered daily oral injections of vehicle or fexaramine (10, 50 or 100 mg/kg) for 5 weeks with HFD. Data represent the mean±STD. Statistical analysis was performed with the Student's t test (*p<0.05, **p<0.01).
Figure 4B:
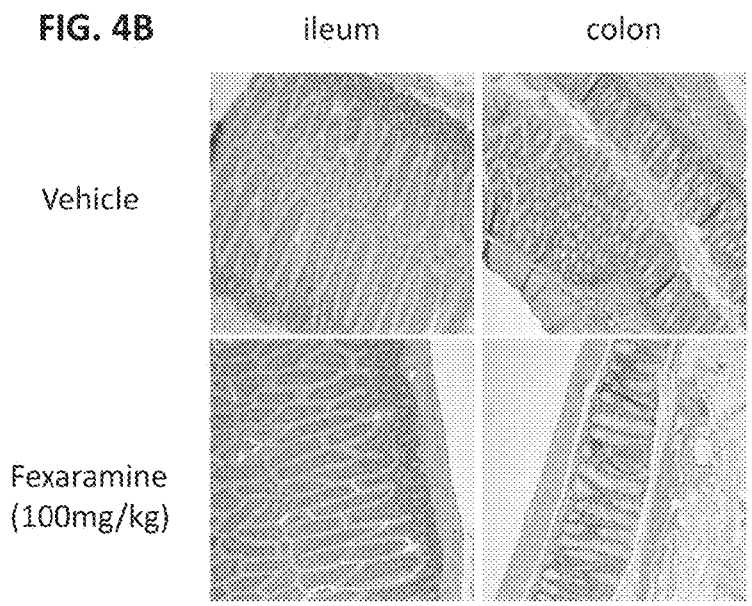
FIG. 4B is a set of digital images showing histological analysis of the ileum and colon following treatment with fexaramine or vehicle. Mice were fed on HFD for 14 weeks, and then administered daily oral injections of vehicle or fexaramine (100 mg/kg) for 5 weeks with HFD.
Figure 5E:
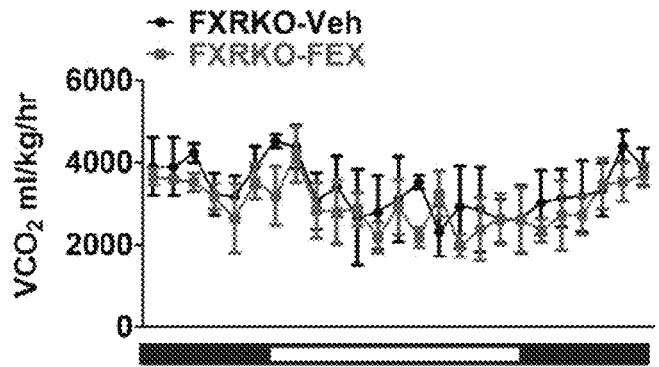
Figure 5F:
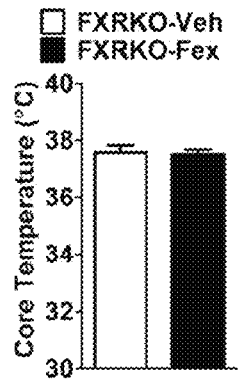
Figure 5G:
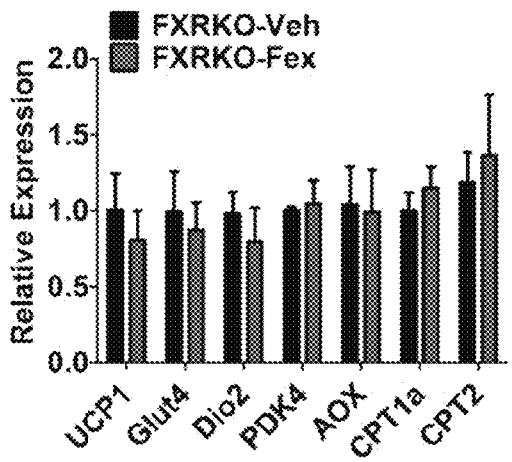
Figure 5H:
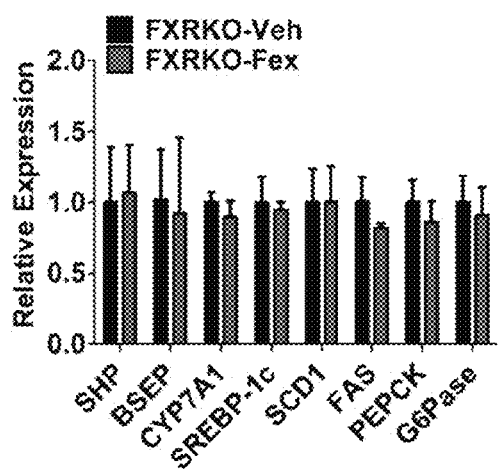
Figure 5I:
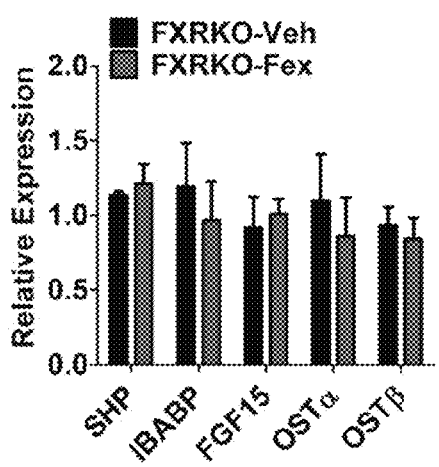

The physiological effects of fexaramine in established obesity (diet-induced obesity, DIO) models were evaluated. C57BL/6J mice were fed a diet of 60% fat for 14 weeks and then treated PO with vehicle or fexaramine (100 mg/kg) for 5 weeks. Surprisingly, chronic fexaramine oral administration prevented weight gain in DIO mice (FIG. 2A). Prevention of weight gain by fexaramine occurred in a dose-dependent manner (FIG. 4A) with no signs of intestinal toxicity (FIG. 4B). At the highest dose weight gain was almost completely abrogated. The reduction in weight gain of Fex-treated mice was largely attributed to reduced overall fat mass (as analyzed by MRI), with significant reductions in wet weights of both subcutaneous (inguinal) and visceral (gonadal and mesenteric) adipose depots (FIGS. 2B and 2C). Consistent with reduced adiposity, Fex-treated mice showed significant improvements in their endocrine and metabolic profiles including reduced glucose, insulin, leptin, cholesterol, and resistin levels Analyses of serum metabolic parameters including leptin, insulin, cholesterol, and resistin reflected that fexaramine-mediated weight gain resistance is accompanied by improved endocrine and metabolic profiles (FIGS. 2D and 4D).

Figure 2F:
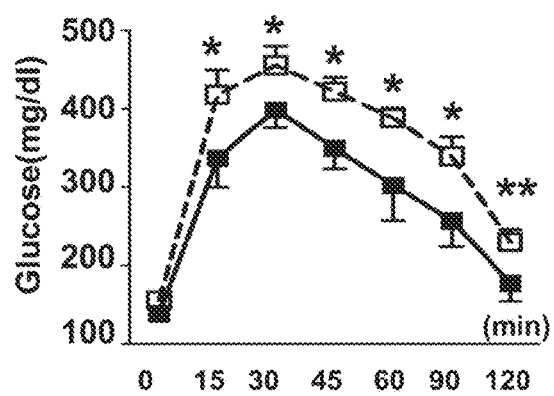
Figure 2G:
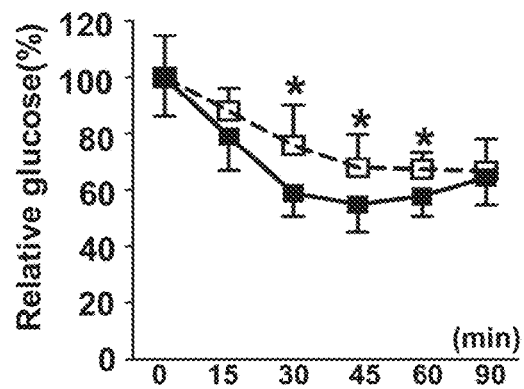
Figure 3A:
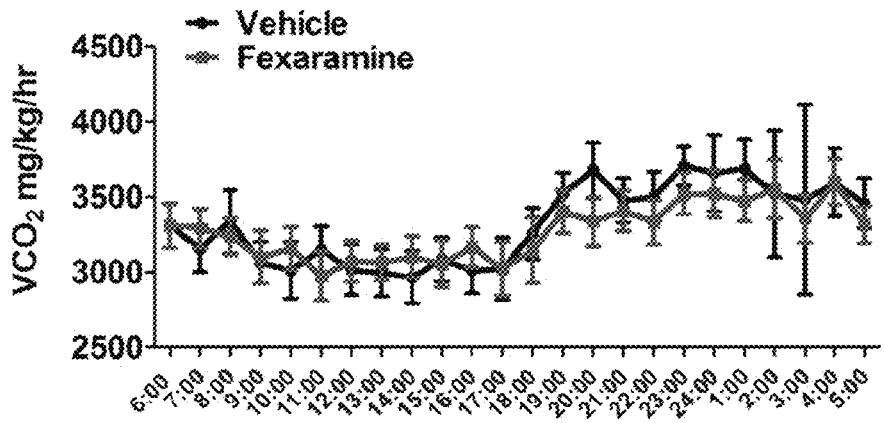
FIGS. 3A-3D are line graphs and a bar graph showing the effects of fexaramine administration in normal chow-fed mice. The mice were treated with vehicle (left bar) or fexaramine (100 mg/kg) (right bar) via PO for 5 weeks. Data represent the mean±STD. Statistical analysis as performed with the Student's t test (*p<0.05, **p<0.01).
Figure 3B:
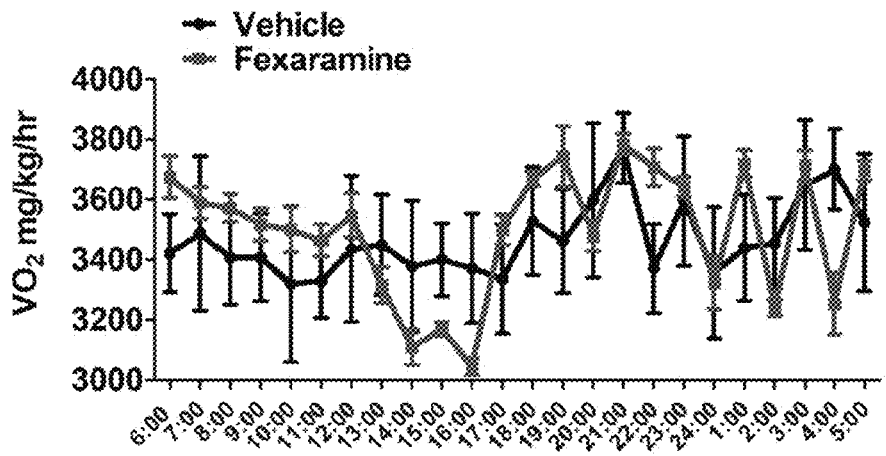
Figure 3C:
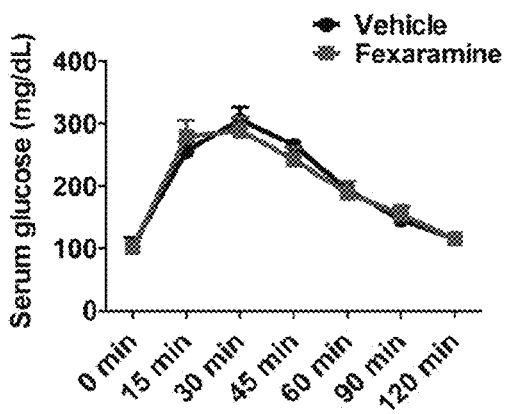
Figure 3D:
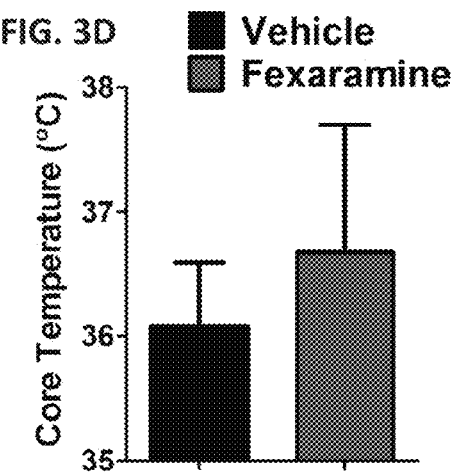

Obesity and its metabolic complications are associated with chronic low-grade inflammation, reflected by elevated serum levels of inflammatory cytokines. Serum levels of inflammatory cytokines TNF$\alpha$, IL-1$\alpha$, IL-1$\beta$, IL-17 and MCP-1 were markedly decreased by fexaramine (FIG. 2E) (such as reductions of at least 50%, at least 75%, at least 80%, or even at least 90%), indicating that fexaramine-induced weight gain resistance reduced systemic inflammation. The reduction in fasting insulin levels also suggested improved glucose tolerance and insulin sensitivity in fexaramine-treated DIO mice. Therefore, glucose tolerance tests (GTTs) and insulin tolerance tests (ITTs) were performed to determine if glucose homeostasis was improved in fexaramine-treated DIO mice. Fex treatment induced dose-dependent improvements in glucose tolerance and insulin sensitivity in DIO mice (measured by glucose and insulin tolerance tests) (FIGS. 2F and 2G and 4C). In addition, while fexaramine improved glucose homeostasis in a dose-dependent manner in DIO mice, there were no effects observed in normal chow-fed mice across a range of doses. Notably, these Fex-induced changes in gene expression and improvements in metabolic homeostasis were abrogated in Fex-treated FXR null mice, establishing the FXR dependence of the observed effects (FIGS. 5A-5I).

Example 3

Fexaramine Enhances Energy Expenditure in Brown Adipose Tissue

As the differential weight effect was not attributable to difference in food intake between vehicle-treated control mice and Fex-treated mice (FIG. 6A), the metabolic rates of weight-matched mice were compared. Fex-treated DIO mice had consistently higher oxygen consumption ($VO_2$) and exhaled more carbon dioxide ($VCO_2$) than vehicle-treated controls (FIGS. 6B-6C), but displayed similar respiratory exchange ratios, suggesting enhanced metabolism of both sugar and fat (FIG. 6M). Based on ambulatory counts, Fex-treated mice were more active than control mice, which can be a result of lower body weights supporting increased energy expenditure in treated mice (FIG. 6D).

Figure 6F:
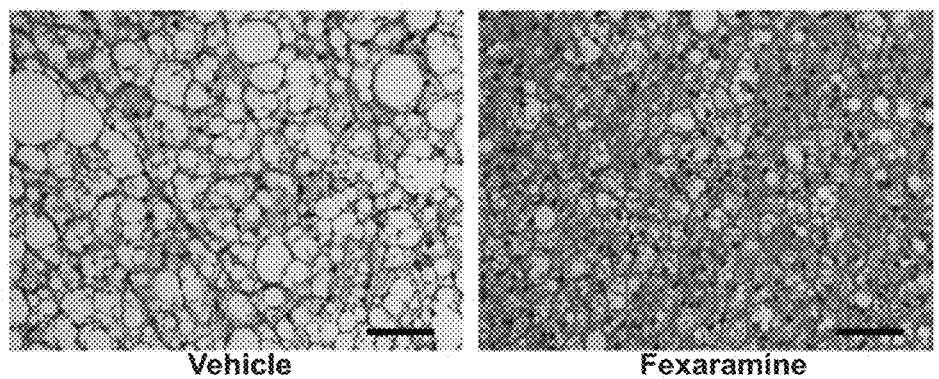
Figure 6G:
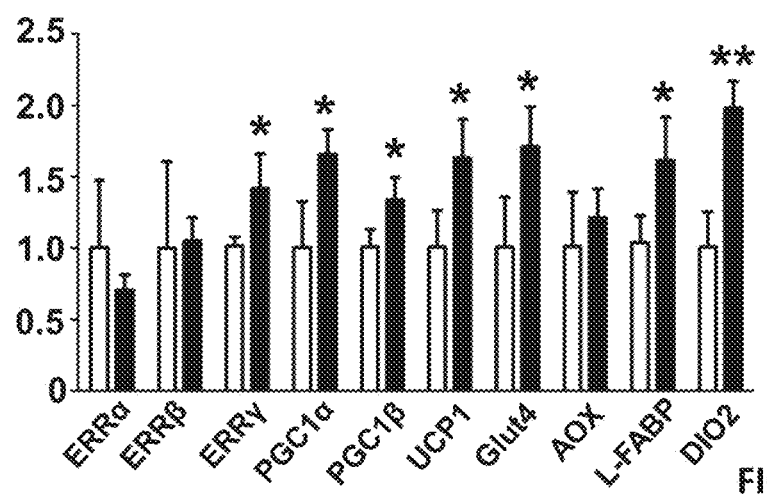
Figure 6H:
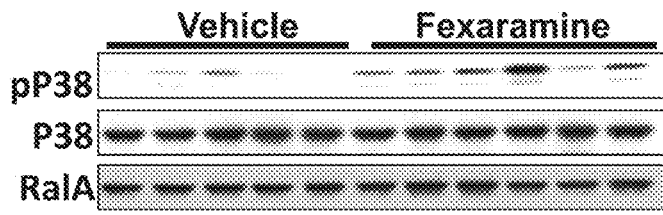
Figure 6I:
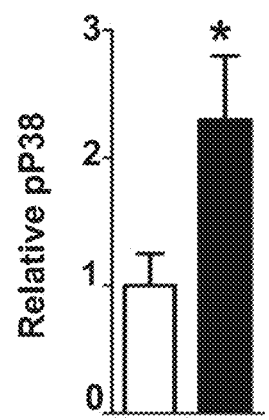

Consistent with increased energy expenditure, Fex treatment increased the core body temperature approximately 1.5° C. (FIG. 6E). In addition, the prominent accumulation of lipid vesicles in brown adipose tissue (BAT) of vehicle-treated DIO mice was markedly reduced in Fex-treated mice (FIG. 6F). Gene expression analysis confirmed the induction of ERR$\gamma$, PGC-1$\alpha$, and PGC-1$\beta$, as well as a number of their target genes involved in thermogenesis, mitochondrial biogenesis, and fatty acid oxidation in BAT (FIG. 6G). Moreover, Fex treatment increased the phosphorylation level of p38 (FIGS. 6H and 6I), previously shown to stabilize PGC-1$\alpha$, a key coactivator of the thermogenic transcriptional program in BAT. A comparison of the transcriptional changes induced by Fex in inguinal, gonadal and brown adipose depots revealed coordinated changes that selectively enhance OXPHOS activity only in BAT, indicating that BAT is a key contributor to the increased energy expenditure and thermogenesis (FIG. 6J). Consistent with this conclusion, KEGG pathway analysis of Fex-induced transcriptional changes from RNA-sequence analysis in BAT identified oxidative phosphorylation as significantly changed (Table 1), and increased PKA activity was seen in Fex-treated mice (FIG. 6L).

TABLE 1

| KEGG pathway Term | p-value |
|---|---|
| Oxidative phosphorylation | 8.12E−07 |
| Chemokine signaling pathway | 2.21E−03 |
| Cytokine-cytokine receptor interaction | 4.40E−03 |
| Biosynthesis of unsaturated fatty acids | 7.04E−03 |
| PPAR signaling pathway | 7.53E−03 |

Furthermore, serum lactate levels were significantly reduced in Fex-treated DIO mice, suggesting that body-wide energy metabolism is shifted towards a more oxidative state (FIG. 6N). Thus, the marked reduction in lipids, increased PKA activity and p38 phosphorylation, and increased core body temperature indicate a coordinated activation of thermogenesis in BAT in Fex-treated DIO mice.

Example 4

Fexaramine Induces FGF15 and Alters Bile Acid Composition

RNA-Seq of intestinal tissues was used to explore the mechanisms through which Fex might contribute to systemic changes in energy expenditure and metabolic rate. Mice were fed on HFD for 14 weeks, and then subjected to daily oral injection of vehicle or fexaramine (100 mg/kg) for 5 weeks with HFD. KEGG pathway analysis revealed the induction of multiple cellular metabolic pathways including PPAR and adipocytokine signaling in both ileum and colon (Tables 2 and 3).

TABLE 2

| KEGG pathway (ileum) | |
|---|---|
| KEGG pathway Term | p-value |
| PPAR signaling pathway | 1.86E−05 |
| Adipocytokine signaling pathway | 2.91E−03 |
| Retinol metabolism | 3.03E−03 |
| Drug metabolism | 4.01E−03 |
| Arachidonic acid metabolism | 5.33E−03 |

TABLE 3

| KEGG pathway (colon) | |
|---|---|
| KEGG pathway Term | p-value |
| PPAR signaling pathway | 3.52E−11 |
| Adipocytokine signaling pathway | 8.90E−03 |
| Retinol metabolism | 7.06E−02 |

Overlap of Fex-induced expression changes with previously identified intestinal FXR binding sites identified a subset of genes as potential direct FXR target genes (FIG. 7A). Within this subset, FGF15 (corresponds to FGF19 in humans) was found to be dramatically up-regulated by Fex. In addition to established FXR target genes such as Lpl, other genes exhibiting regulation by FXR were identified including Perl (FIG. 7A).

Figure 7F:
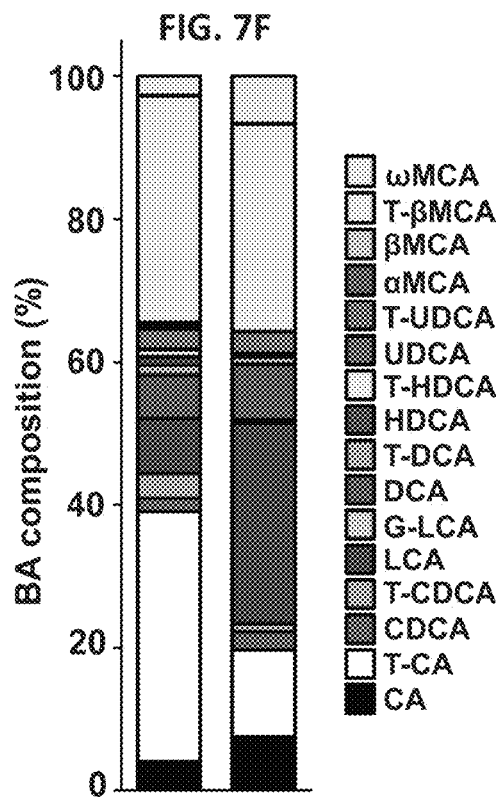
Figure 8:
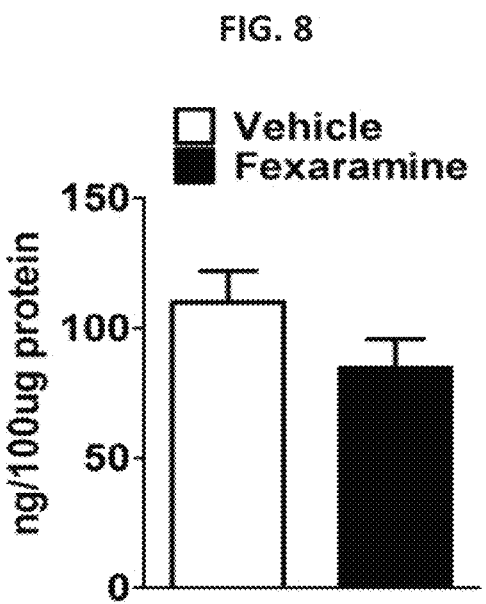
FIG. 8 is a bar graph showing hepatic Cyp7a1 levels determined by ELISA. Data represent the mean±SD. Statistical analysis was performed with the Student's t test. *p<0.05, **p<0.01.
Figure 10D:
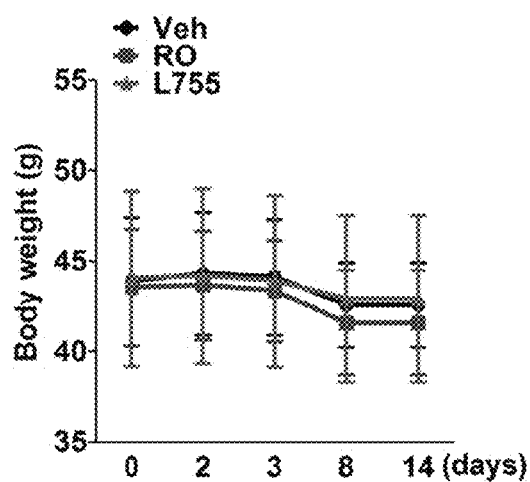
Figure 10E:
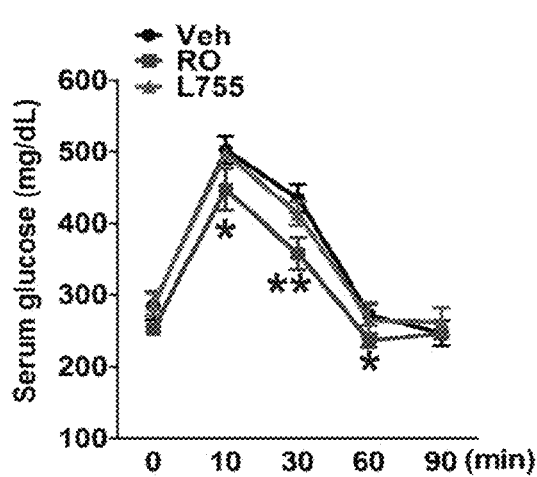
Figure 10F:
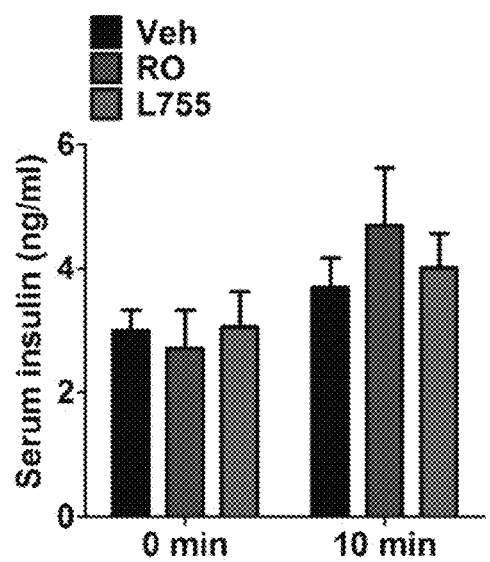

As an intestinal endocrine hormone, FGF15 induction is of interest since it activates the thermogenic program in BAT, as well as negatively regulate BA synthesis through suppression of hepatic CYP7A1, the rate-limiting enzyme for BA synthesis. An increase in circulating FGF15 accompanied the increase in mRNA expression in ileum (FIGS. 7B and 7C) (such as an increase of at least 100%, at least 125%, or at least 150%). Consistent with an increase in serum FGF15, hepatic CYP7A1 expression was significantly repressed at both the mRNA and protein level after chronic Fex treatment, while the expression of CYP8B1 and CYP27A1 (enzymes not regulated by FGF15) were not affected (FIG. 7D and FIG. 8). In addition, expression of established liver FXR target genes SHP and BSEP were not altered, further demonstrating the absence of hepatic FXR activation after chronic Fex treatment (FIG. 7D) and indicating that other pathways, such as FGF15, mediate changes in hepatic gene expression.

Genetic activation of intestinal FXR has been previously shown to alter bile acid composition. This is relevant as dietary, microbial or hepatic stress can alter the pool and enhance the production of toxic and cholestatic BAs such as taurine-conjugated chenodeoxycholic acid (T-CDCA) and taurine-conjugated cholic acid (T-CA). Despite the apparent absence of hepatic FXR activation, Fex treatment produced striking changes in the composition of the BA pool In addition to reducing the bile acid pool size, Fex treatment changed the relative proportions of circulating bile acids, most notably decreasing the fraction of taurocholic acid and increasing the fraction of the secondary bile acid, lithocholic acid (FIGS. 7E and 7F, Table 4). These changes are in keeping with increased intestinal FXR activation, including the effects of increased circulating FGF15 on bile acid synthesis in the liver. Indeed, decreased serum taurocholic acid has been previously reported in mice expressing a constitutively activated FXR transgene in intestine, as well as after injection of FGF19, the human analogue of FGF15 (Wu et al. *PloS one* 6, e17868, 2011). Furthermore, changes in bile acid synthesis away from cholic acid towards chenodeoxycholic acid and its derivatives, which includes lithocholic acid, were observed upon FGF19 treatment, consistent with a reduction in hepatic CYP7A1 and an increase in CYP7B1 expression.

TABLE 4

| Fexaramine alters the serum bile acid composition | | |
|---|---|---|
| | Bile Acid Composition (%) | |
| | Vehicle | Fexaramine |
| CA | 4.08 | 7.51 |
| TCA | 34.96 | 12.23 |
| CDCA | 1.86 | 2.51 |
| TCDCA | 3.52 | 1.13 |
| LCA | 7.67 | 28.13 |
| GLCA | N.D. | 0.51 |
| DCA | 6.03 | 7.67 |
| TDCA | 1.42 | 1.02 |
| HDCA | 1.20 | 0.36 |
| T-HDCA | 0.99 | N.D |
| UDCA | 0.01 | 0.05 |
| T-UDCA | 2.85 | 3.07 |
| alpha MCA | 0.33 | N.D |
| beta MCA | 0.55 | N.D |
| T-beta MCA | 31.78 | 29.16 |
| omega MCA | 2.74 | 6.65 |

Mice fed a HFD for 14 weeks were maintained on a HFD and treated with vehicle or fexaramine (100 mg/kg/day per os for 5 week). Serum bile acid composition was determined by mass spectrometry. N.D not determined.

Figure 7G:
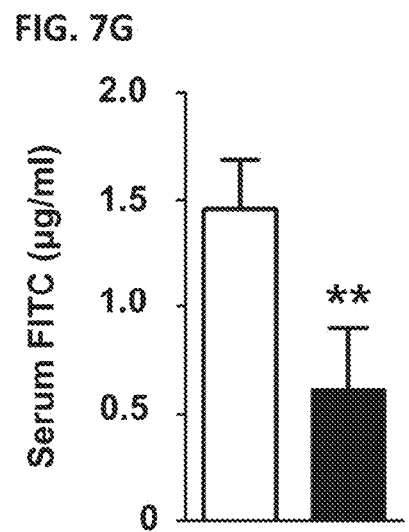
Figure 7H:
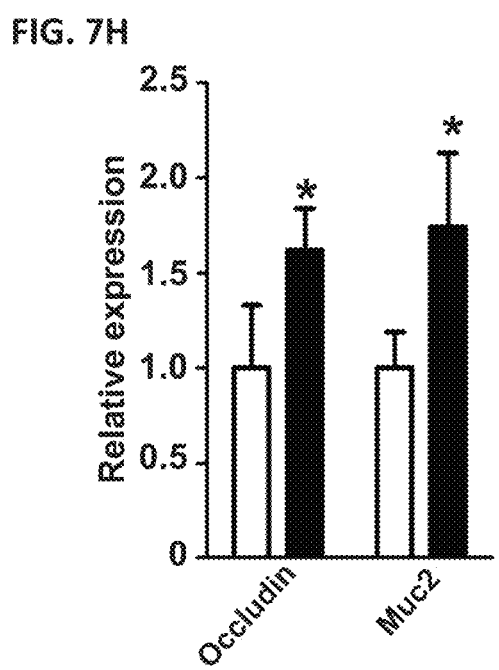

FXR activation has been reported to enhance mucosal defense gene expression and intestinal barrier function (Inagaki et al., *Proc Natl Acad Sci USA* 103:3920-3925, 2006; Gadaleta., et al. *Gut* 60:463-472, 2011). Consistent with these reports, mice showed reduced intestinal permeability, as measured by FITC-dextran leakage into the serum, and increased expression of mucosal defense genes Occludin and Muc2, after chronic Fex-treatment (FIGS. 7G and 7H).

While Fex does not activate the G protein-coupled bile acid receptor, TGR5 (FIG. 9), the pronounced changes in BAs indicated that this pathway may contribute to the observed physiologic effects. Notably, treatment of HFD-fed mice with the intestinally-restricted TGR5 agonist, L7550379, failed to induce metabolic changes, while treatment with the systemic TGR5 agonist, RO5527239 improved glucose homeostasis, as measured by GTT and insulin secretion (FIGS. 10A-10F). These results indicated that TGR5 activation outside of the intestine may contribute to the beneficial effects of Fex treatment (FIGS. 10B, 10D, 10E and 10F).

To address this possibility, HFD-fed TGR5 null mice were chronically treated with Fex (100 mg/kg/day PO for 5 weeks). As seen in wild type mice, Fex treatment induced multiple FXR target genes in the ileum of TGR5 null mice including FGF15, resulting in lowered serum BA levels (FIGS. 11A, 11B). In this TGR5 null background, Fex treatment induced moderate improvements in fasting glucose levels and glucose tolerance (FIGS. 11C, 11D). In addition, somewhat blunted increases in core body temperature and metabolic rate, correlating with the induction of thermogenic genes in BAT, were observed (FIGS. 11E-11H), indicating that these effects do not require TGR5 activation. In contrast to wild type mice, no significant changes in weight gain or insulin sensitivity were observed in Fex treated TGR5 null mice, and altered gene expression patterns were seen in the liver and muscle, indicating involvement of the TGR5 pathway (FIGS. 11I-11N). In particular, the anti-lipogenic effects of Fex in the liver appear to require TGR5 activation, as key hepatic lipogenic genes and liver triglyceride content were not affected by Fex treatment (FIGS. 11L, 11M).

Example 5

Fexaramine Induces Browning of White Adipose Tissue

During obesity, adipose tissue expands by hyperplastic and/or hypertrophic growth, is chronically inflamed, and produces inflammatory cytokines that ultimately contribute to systemic metabolic dysregulation. After chronic Fex-treatment, the cross-sectional area of adipocytes in visceral depots including gonadal and mesenteric was markedly reduced (FIG. 12A). Investigation of signaling pathways implicated in diet-induced inflammation identified reduced levels of IKK-ε and TANK-binding kinase 1 (TBK1) in Fex-treated DIO mice (FIGS. 12B, 13). These noncanonical IκB kinases were recently shown to play crucial roles in energy expenditure as a consequence of adipose tissue inflammation upon diet-induced obesity (Reilly et al., *Nat Med* 19:313-321, 2013). In addition, activation of the mammalian target of rapamycin complexi (mTORC1) pathway, a key lipogenic pathway activated by high fat diet (HFD), was reduced in Fex-treated gonadal WAT, as evidenced by reduced S6K phosphorylation (FIG. 12B). Consistent with reduced adiposity, expression of the inflammatory cytokines TNFα, MCP-1 and IL-1α, as well as the macrophage marker F4/80, were reduced in visceral and brown adipose depots of Fex-treated mice (FIGS. 12C and 14).

Brown adipose-driven adaptive thermogenesis is fueled by mitochondrial oxidation of free fatty acids (FFAs) released from triglyceride stores into the circulation predominantly by the action of hormone-sensitive lipase (HSL). Low levels of HSL phosphorylation were seen in visceral and subcutaneous adipose depots from control mice, as expected, due to desensitization of the β-adrenergic pathway in WAT during obesity (Carmen & Victor, *Cell Signal* 18:401-408, 2006; Song et al. *Nature* 468:933-9, 2010). In contrast, a pronounced increase in HSL phosphorylation and serum levels of free fatty acids (FIGS. 12D and 12G), accompanied by increased serum catecholamine levels and β3-adrenergic receptor expression (FIGS. 12C, 12E and 12F), was observed after chronic Fex treatment. As β-adrenergic receptor activation has been shown to induce "brown fat-like" cells in inguinal adipose tissue, and these cells have been associated with resistance to diet-induced obesity and improved glucose metabolism (Tsukiyama-Kohara et al., *Nat Med* 7:1128-1132, 2001; Fisher et al., *Genes Dev* 26:271-281, 2012; Hansen et al., *Proc Natl Acad Sci USA* 101:4112-4117, 2004; Wang et al., *Mol Cell Biol* 28:2187-2200, 2008), UCP-1 expression was examined in inguinal adipose tissue. Immunohistochemistry revealed a substantial increase in the abundance of multi-locular, UCP1-expressing adipocytes in Fex-treated animals (FIG. 12H). Furthermore, Fex-treatment increased the expression of "brown fat-like" signature genes, as well as increased respiratory capacity in the stromal vascular fraction from inguinal adipose tissue (FIGS. 12I and 12J). These results indicate that Fexaramine, unlike systemic FXR ligands, induces a distinct coordinated metabolic response, enhancing β-adrenergic signaling to promote lipolysis, mobilizing fatty acids for oxidation in BAT and the "browning" of cells in white adipose tissue.

Example 6

Fexaramine Improves Insulin Sensitivity and Glucose Tolerance

To probe the mechanism through which chronic Fex treatment improved glucose homeostasis, hyperinsulinemic-euglycemic clamp studies were performed. No differences in basal hepatic glucose production (HGP), glucose disposal rate (GDR), insulin-stimulated GDR (IS-GDR), free fatty acid (FFA) suppression, and fasting insulin levels were observed between weight-matched cohorts (generated by treating initially heavier mice (2-3 grams) with Fex (FIGS. 15A-15C, FIGS. 15I and 15K)). However, Fex-treated mice displayed a marked increase in insulin-mediated suppression of HGP compared to control DIO mice (FIG. 15D). Thus, while the attenuated weight gain can contribute to improved glucose clearance in Fex-treated mice, this improvement in hepatic glucose suppression indicates enhanced liver insulin sensitivity after Fex treatment.

Liver insulin resistance has been linked to obesity-induced hepatic steatosis (Cohen et al., *Science* 332:1519-1523, 2011). Histological examination of liver tissue from Fex-treated DIO mice revealed a reduction in lipid droplets compared to controls indicating amelioration of hepatic steatosis (FIG. 15E). Consistent with this histology, a marked decrease in hepatic triglycerides (such as a reduction of at least 10%, or at least 20%) and reduced hepatic expression of gluconeogenic and lipogenic genes (such as a reduction of at least 20%, or at least 30%, or at least 50%)

were seen after chronic Fex treatment (FIGS. 15F and 15G). Furthermore, decreased serum alanine aminotransferase (ALT) levels were measured in Fex-treated mice, indicating reduced HFD-induced liver damage (FIG. 15H). Thus, in DIO mice Fex promotes hepatic insulin sensitization, reduced steatosis, improved metabolic markers, decreased ALT and enhanced BAT activity.

Example 7

FXR Activity Screen for Determining $EC_{50}$ Determination

Cell Culture and Transfection:

CV-1 cells were grown in DMEM+10% charcoal stripped FCS. Cells were seeded into 384-well plates the day before transfection to give a confluency of 50-80% at transfection. A total of 0.8 grams DNA containing 0.32 micrograms pCMX-hFXRf1, 0.32 micrograms pCMX-hRXRf1, 0.1 micrograms pCMX.beta.Gal, 0.08 micrograms pGLFXRE reporter and 0.02 micrograms pCMX empty vector was transfected per well using FuGene transfection reagent according to the manufacturer's instructions (Roche). Cells were allowed to express protein for 48 hours followed by addition of compound.

Plasmids:

Human FXR full length and RXR full length was obtained from Ronald Evans' laboratory and PCR amplification of the hFXR cDNA and the hRXR cDNA was performed. The amplified cDNAs was cloned into the vector pCMX generating the plasmids pCMX-hFXRf1 and pCMX-hRXRf1. Ensuing fusions were verified by sequencing. The pCMXMH2004 luciferase reporter contains multiple copies of the GAL4 DNA response element under a minimal eukaryotic promoter (Hollenberg and Evans, 1988). pCMX.beta.Gal was generated in the Evans laboratory, Salk Institute.

Compounds:

All compounds were dissolved in DMSO and diluted 1:1000 upon addition to the cells. Compounds were tested in quadruple in concentrations ranging from 0.001 to 100 µM. Cells were treated with compound for 24 hours followed by luciferase assay. Each compound was tested in at least two separate experiments.

Luciferase Assay:

Medium including test compound was aspirated and washed with PBS. 50 µL PBS including 1 mM $Mg^{2+}$ and $Ca^{2+}$ were then added to each well. The luciferase assay was performed using the LucLite kit according to the manufacturer's instructions (Packard Instruments). Light emission was quantified by counting on a Perkin Elmer Envision reader. To measure 3-galactosidase activity 25 µL supernatant from each transfection lysate was transferred to a new 384 microplate. Beta-galactosidase assays were performed in the microwell plates using a kit from Promega and read in a Perkin Elmer Envision reader. The beta-galactosidase data were used to normalize (transfection efficiency, cell growth etc.) the luciferase data.

Statistical Methods:

The activity of a compound is calculated as fold induction compared to an untreated sample. For each compound the efficacy (maximal activity) is given as a relative activity compared to Fexaramine, a FXR agonist. The $EC_{50}$ is the concentration giving 50% of maximal observed activity. $EC_{50}$ values were calculated via non-linear regression using GraphPad PRISM (GraphPad Software, San Diego, Calif.).

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:
1. A compound selected from
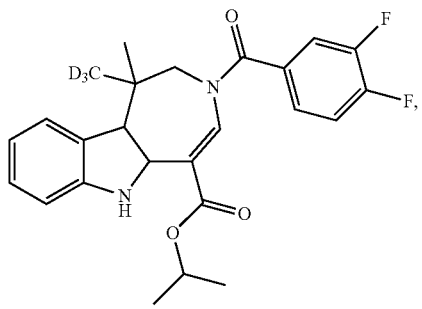
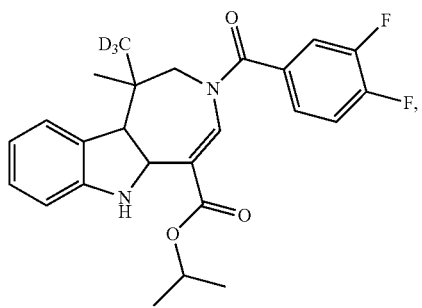
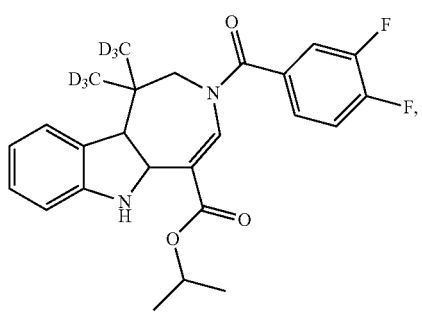
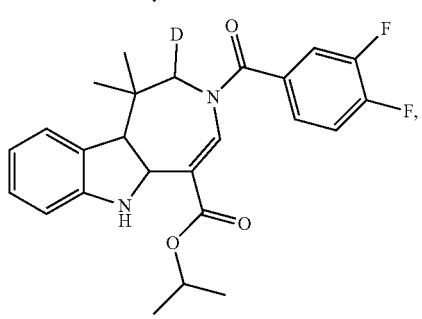
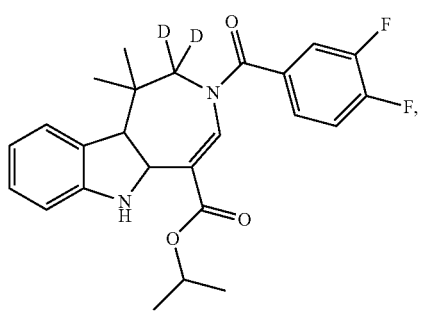
-continued
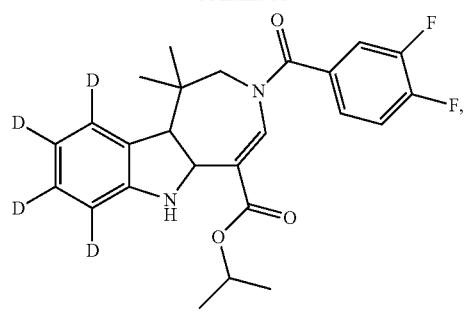
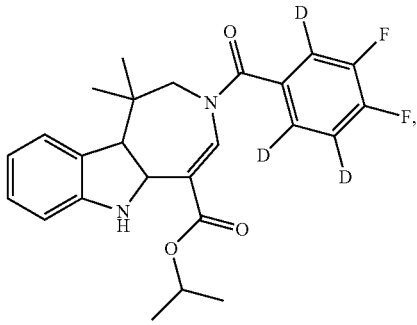
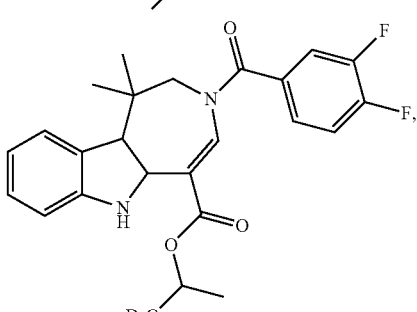
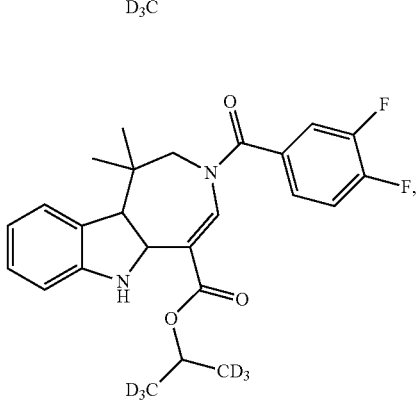
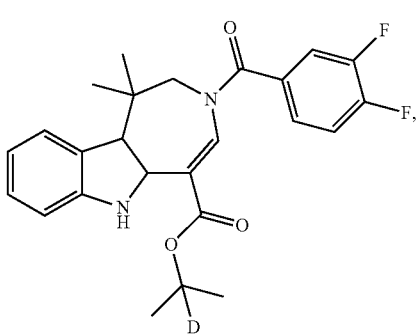

115
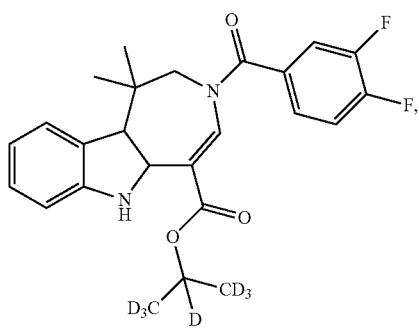
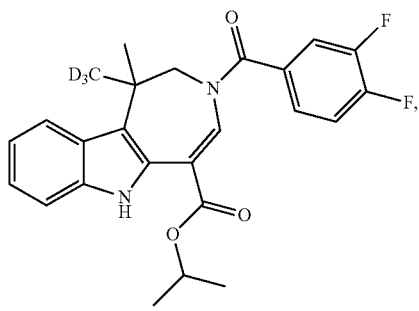
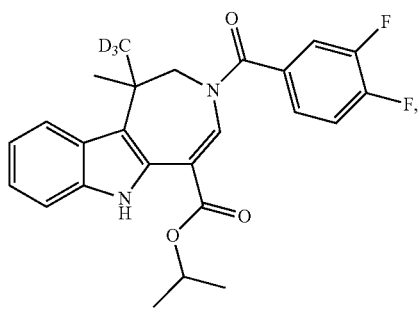
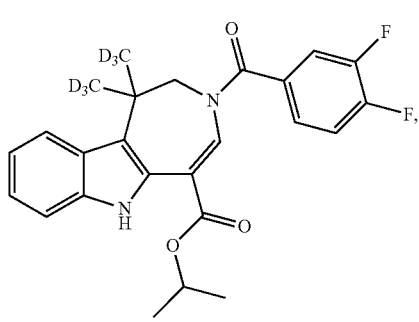
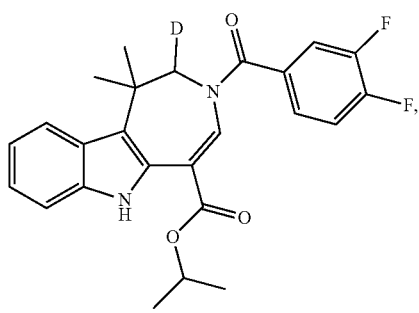
116
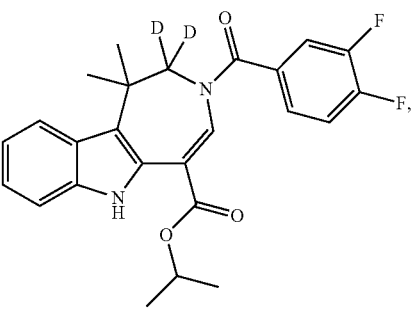
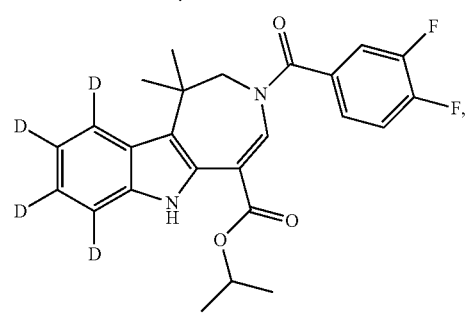
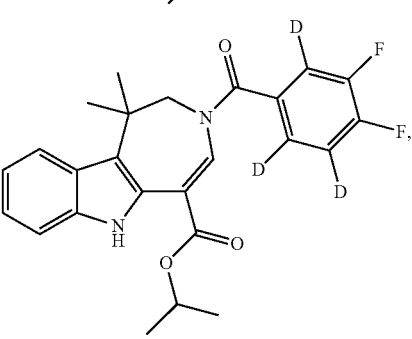
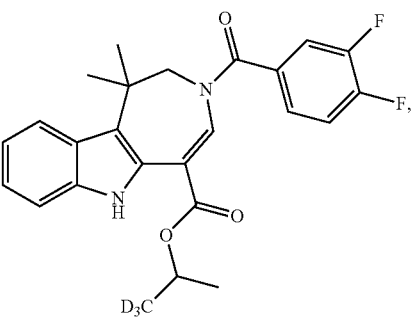
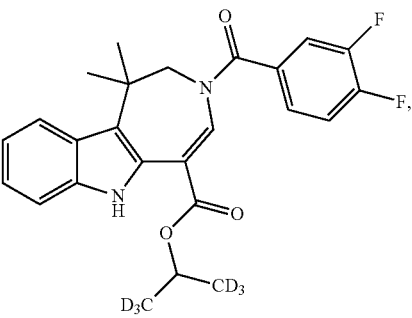

117
-continued
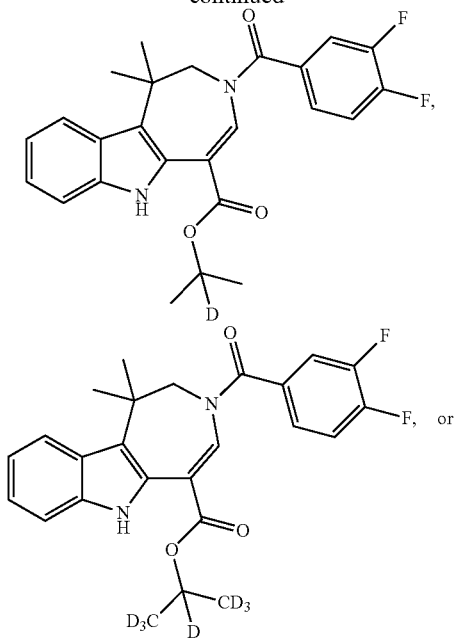
118
-continued
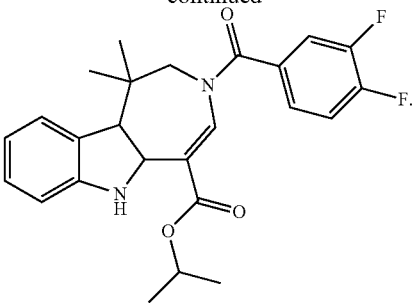
2. A composition, comprising:
at least a first compound of claim 1; and
a pharmaceutically acceptable excipient.
* * * * *

SEQUENCE LISTING

<160> NUMBER OF SEQ ID NOS: 2

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 33
<212> TYPE: PRT
<213> ORGANISM: Homo sapiens

<400> SEQUENCE: 2

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp